United States Patent
East et al.

(10) Patent No.: US 9,744,338 B2
(45) Date of Patent: Aug. 29, 2017

(54) SYSTEMS AND METHODS FOR SHUNTING FLUID

(71) Applicant: Alcyone Lifesciences, Inc., Lowell, MA (US)

(72) Inventors: Andrew East, Arlington, MA (US); Morgan Brophy, Somerville, MA (US); Deep Arjun Singh, Cambridge, MA (US); P J Anand, Lowell, MA (US); Robert Degon, Bellingham, MA (US); Timothy Fallon, Dover, MA (US); Allison Waller, Blackstrone, MA (US); Matthew Attar, Seekonk, MA (US)

(73) Assignee: Alcyone Lifesciences, Inc., Lowell, MA (US)

( * ) Notice: Subject to any disclaimer, the term of this patent is extended or adjusted under 35 U.S.C. 154(b) by 0 days.

(21) Appl. No.: 14/690,389

(22) Filed: Apr. 18, 2015

(65) Prior Publication Data

US 2015/0297874 A1 Oct. 22, 2015

Related U.S. Application Data

(60) Provisional application No. 61/981,699, filed on Apr. 18, 2014.

(51) Int. Cl.
*A61M 5/00* (2006.01)
*A61M 27/00* (2006.01)
(Continued)

(52) U.S. Cl.
CPC ........ *A61M 27/006* (2013.01); *A61M 39/225* (2013.01); *A61M 2027/004* (2013.01); *A61M 2039/0018* (2013.01)

(58) Field of Classification Search
CPC ...... A61M 27/006; A61M 27/00; A61M 1/00; A61M 39/225; A61M 2205/75;
(Continued)

(56) References Cited

U.S. PATENT DOCUMENTS

| 3,111,125 A | 11/1963 | Schulte |
| 3,452,757 A | 7/1969 | Ames |

(Continued)

FOREIGN PATENT DOCUMENTS

| WO | 83/01387 A1 | 4/1983 |
| WO | 91/17779 A1 | 11/1991 |

(Continued)

OTHER PUBLICATIONS

U.S. Appl. No. 14/160,695, filed Jan. 22, 2014, Systems and Methods for Shunting Fluid.
(Continued)

*Primary Examiner* — Philip R Wiest
(74) *Attorney, Agent, or Firm* — Nutter McClennen & Fish LLP

(57) ABSTRACT

Systems and methods are provided herein that generally involve shunting fluid, e.g., shunting cerebrospinal fluid in the treatment of hydrocephalus. Self-cleaning catheters are provided which include split tips configured such that pulsatile flow of fluid in a cavity in which the catheter is inserted can cause the tips to strike one another and thereby clear obstructions. Catheters with built-in flow indicators are also provided. Exemplary flow indicators include projections that extend radially inward from the interior surface of the catheter and which include imageable portions (e.g., portions which are visible under magnetic resonance imaging (MRI)). Movement of the flow indicators caused by fluid flowing through the catheter can be detected using MRI, thereby providing a reliable indication as to whether the
(Continued)

catheter is partially or completely blocked. Systems and methods for flushing a shunt system are also disclosed herein, as are various systems and methods for opening auxiliary fluid pathways through a shunt system.

12 Claims, 44 Drawing Sheets

(51) Int. Cl.
*A61M 39/22* (2006.01)
*A61M 39/00* (2006.01)

(58) Field of Classification Search
CPC .. A61M 2205/7545; A61M 2205/7563; A61M 2027/004; A61M 2039/0018
USPC ................................................ 604/8–10, 151
See application file for complete search history.

(56) References Cited

U.S. PATENT DOCUMENTS

| | | | |
|---|---|---|---|
| 3,492,996 | A | 2/1970 | Fountain |
| 3,595,240 | A | 7/1971 | Mishler |
| 3,827,439 | A | 8/1974 | Schulte et al. |
| 3,886,948 | A | 6/1975 | Hakim |
| 4,464,168 | A | 8/1984 | Redmond et al. |
| 4,474,569 | A | 10/1984 | Newkirk |
| 4,560,375 | A | 12/1985 | Schulte et al. |
| 4,698,058 | A | 10/1987 | Greenfeld et al. |
| 4,741,730 | A | 5/1988 | Dormandy |
| 4,850,955 | A | 7/1989 | Newkirk |
| 4,861,331 | A | 8/1989 | East et al. |
| 4,867,741 | A | 9/1989 | Portnoy |
| 5,106,368 | A | 4/1992 | Uldall et al. |
| 5,154,693 | A | 10/1992 | East et al. |
| 5,167,615 | A | 12/1992 | East et al. |
| 5,304,114 | A | 4/1994 | Cosman |
| 5,387,188 | A | 2/1995 | Watson |
| 5,637,083 | A | 6/1997 | Bertrand et al. |
| 5,843,013 | A | 12/1998 | Lecuyer et al. |
| 6,193,682 | B1 | 2/2001 | Ahmed |
| 6,383,159 | B1 | 5/2002 | Saul |
| 6,453,185 | B1 | 9/2002 | O'Keefe |
| 6,875,192 | B1 | 4/2005 | Saul et al. |
| 6,916,313 | B2 | 7/2005 | Cunningham |
| 7,189,221 | B2 | 3/2007 | Silverberg et al. |
| 7,235,060 | B2 | 6/2007 | Kraus |
| 7,842,002 | B2 | 11/2010 | Mantle |
| 9,433,764 | B2 | 9/2016 | East et al. |
| 2002/0128588 | A1 | 9/2002 | Borgesen |
| 2004/0147871 | A1 | 7/2004 | Burnett |
| 2004/0260249 | A1 | 12/2004 | Kulessa |
| 2005/0277862 | A1 | 12/2005 | Anand |
| 2010/0121250 | A1 | 5/2010 | Pizzi |
| 2012/0095485 | A1 | 4/2012 | Cully et al. |
| 2012/0232461 | A1 | 9/2012 | Seaver et al. |
| 2012/0232462 | A1 | 9/2012 | Miethke |
| 2012/0302938 | A1 | 11/2012 | Browd et al. |
| 2014/0094735 | A1 | 4/2014 | Wilson et al. |
| 2014/0207043 | A1 | 7/2014 | Anand et al. |
| 2014/0207045 | A1 | 7/2014 | Anand et al. |
| 2015/0367110 | A1 | 12/2015 | East et al. |
| 2016/0038724 | A1* | 2/2016 | Madsen .............. A61M 27/006 604/9 |

FOREIGN PATENT DOCUMENTS

| | | |
|---|---|---|
| WO | 2007/092875 A2 | 8/2007 |
| WO | 2008/027322 A1 | 3/2008 |
| WO | 2011/104712 A1 | 9/2011 |
| WO | 2011/146757 A2 | 11/2011 |
| WO | 2012/055048 A1 | 5/2012 |
| WO | 2014/116640 A1 | 7/2014 |
| WO | 2014/149648 A1 | 9/2014 |

OTHER PUBLICATIONS

U.S. Appl. No. 14/160,768, filed Jan. 22, 2014, Systems and Methods for Shunting Fluid.
U.S. Appl. No. 14/740,478, filed Jun. 16, 2015, Systems and Methods for Shunting Fluid.
[No Author Listed] Integra Neurosciences™, "Integra™ Flow Regulating Valve, Mini," 2010 (12 pages).
[No Author Listed] Integra Neurosciences™ "Ventricular Drainage System," 2002 (20 pages).
Garton et al., "Hydrocephalus," Ped. Clin. N. Am., 51, pp. 305-325, 2004 (21 pages).
International Invitation to Pay Additional Fees for Application No. PCT/US2014/12449 mailed Mar. 27, 2014 (2 Pages).
International Search Report and Written Opinion for PCT/US2014/012449, mailed May 27, 2014 (24 pages).
International Search Report and Written Opinion for PCT/US2015/026555, mailed Jul. 13, 2015. (11 pages).
Extended European Search Report for Application No. 14770962.0, issued Aug. 18, 2016 (7 pages).
International Search Report and Written Opinion for Application No. PCT/US2014/020082, mailed Jun. 6, 2014 (9 pages).
International Preliminary Report on Patentability for Application No. PCT/US2014/020082, mailed Sep. 24, 2015 (9 Pages).
Extended European Search Report for Application No. 14743442.7, issued Jun. 1, 2016 (10 pages).

* cited by examiner

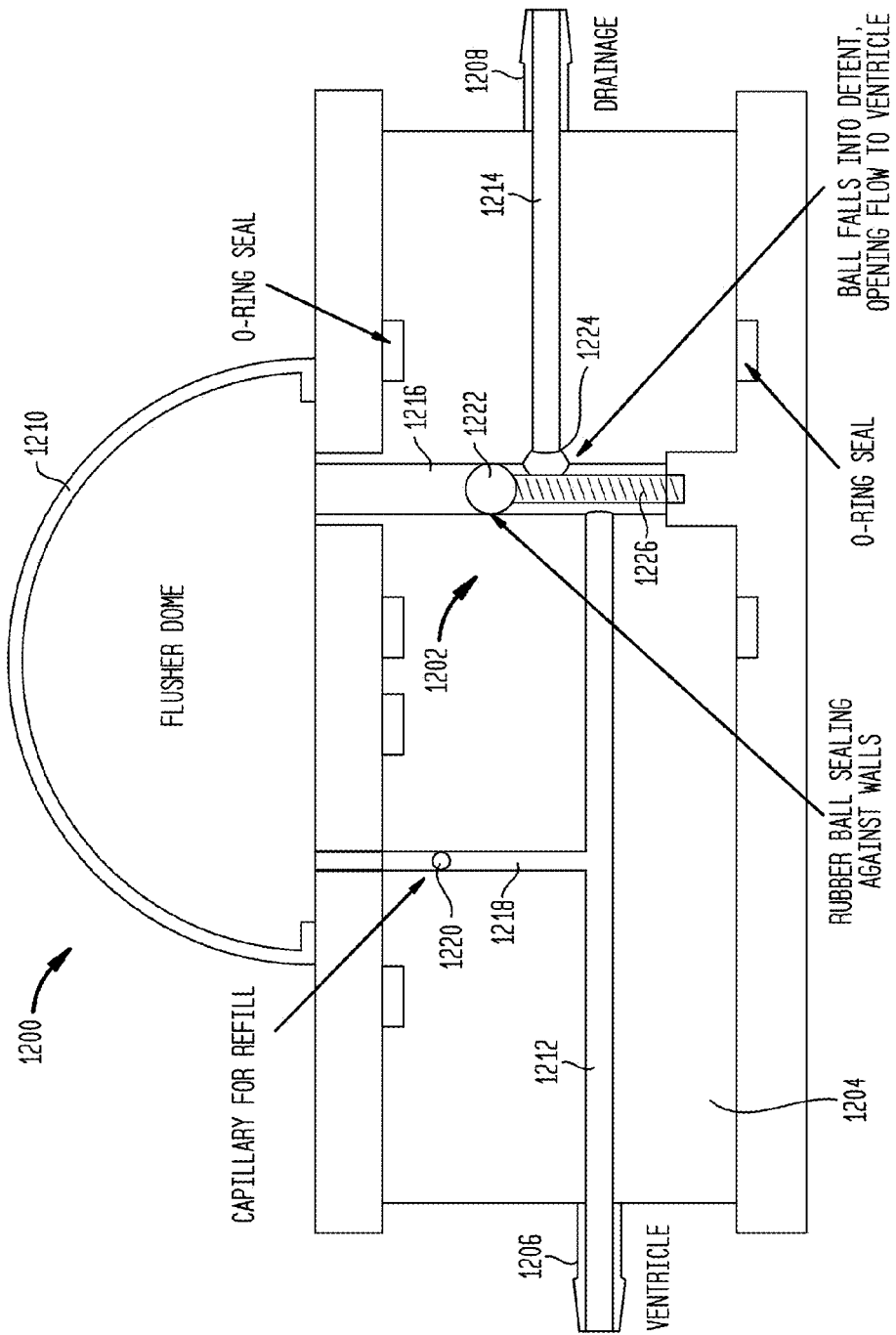

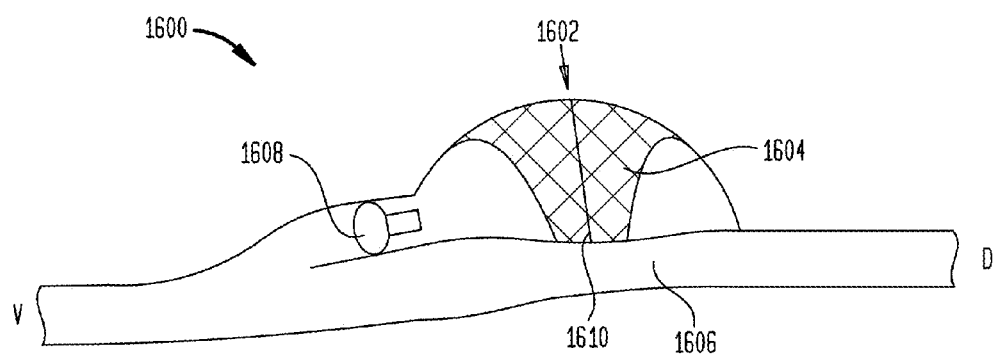
FIG. 16
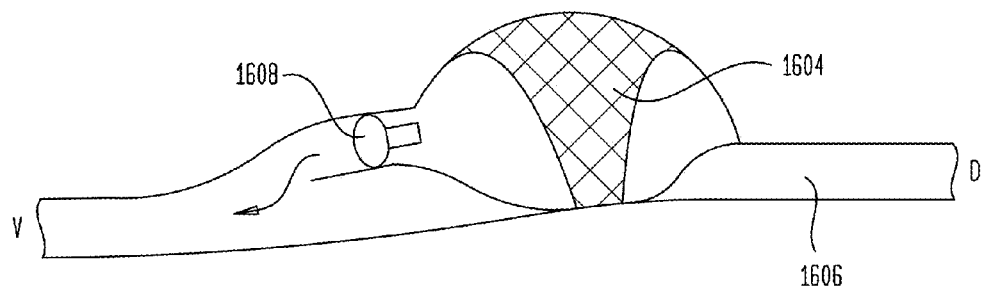
FIG. 17
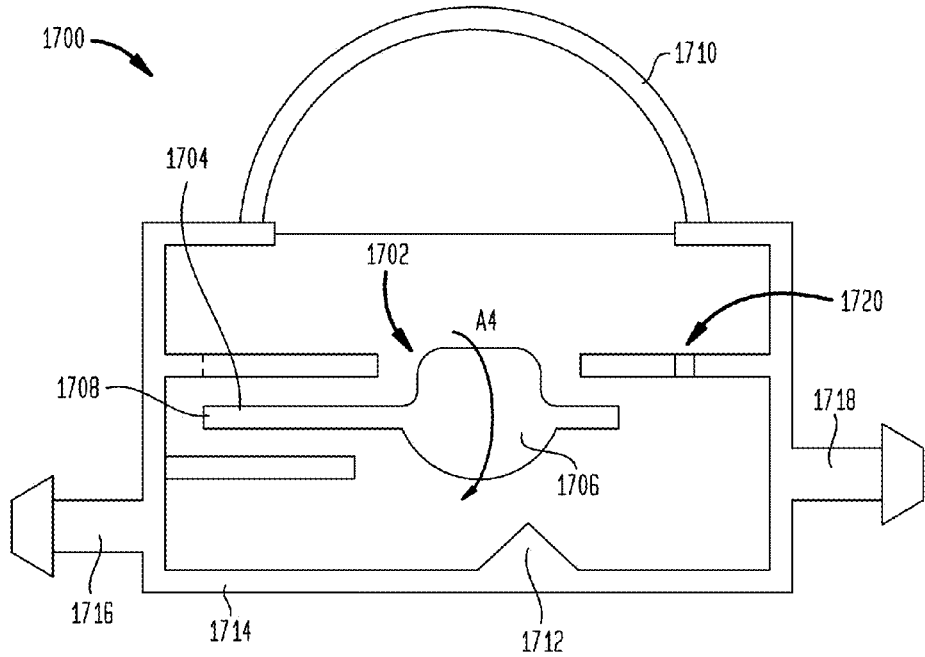

INACTIVE

ACTIVE

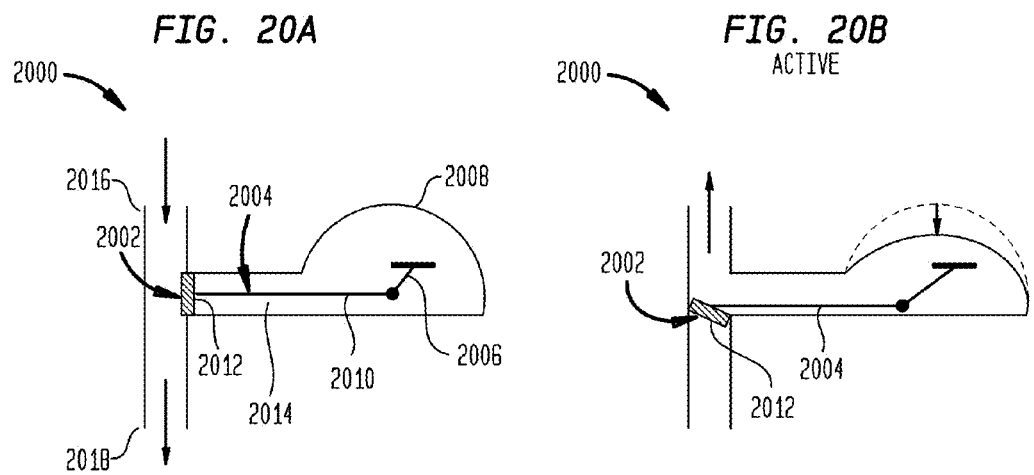
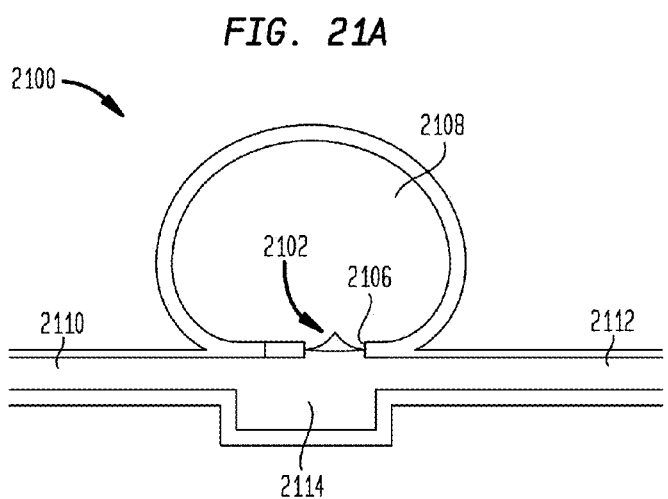

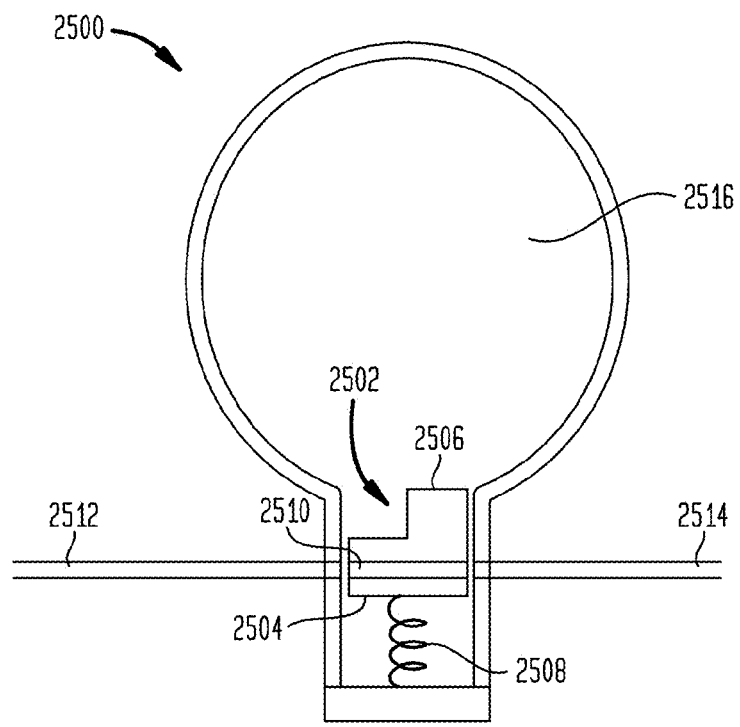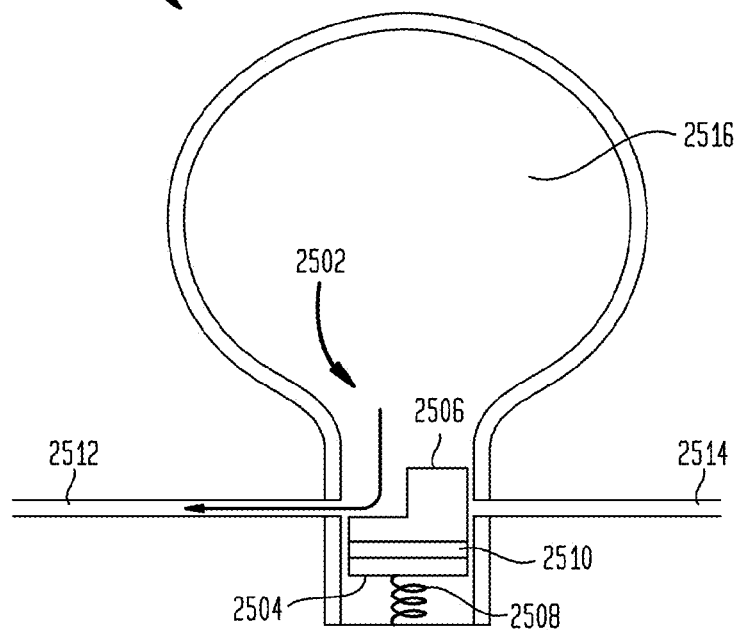

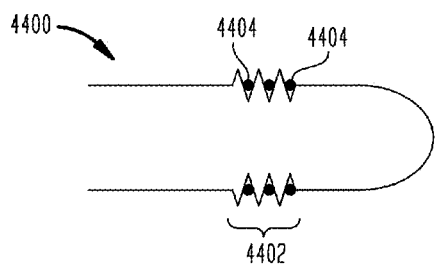
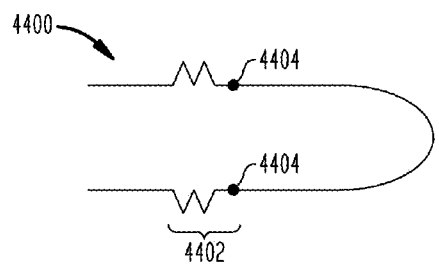
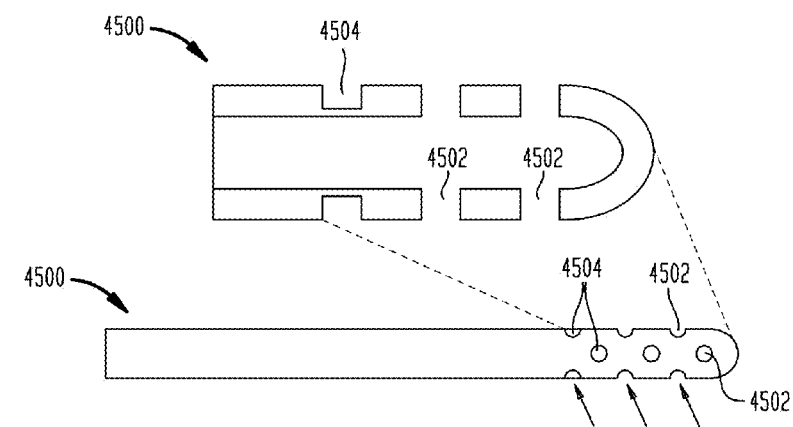
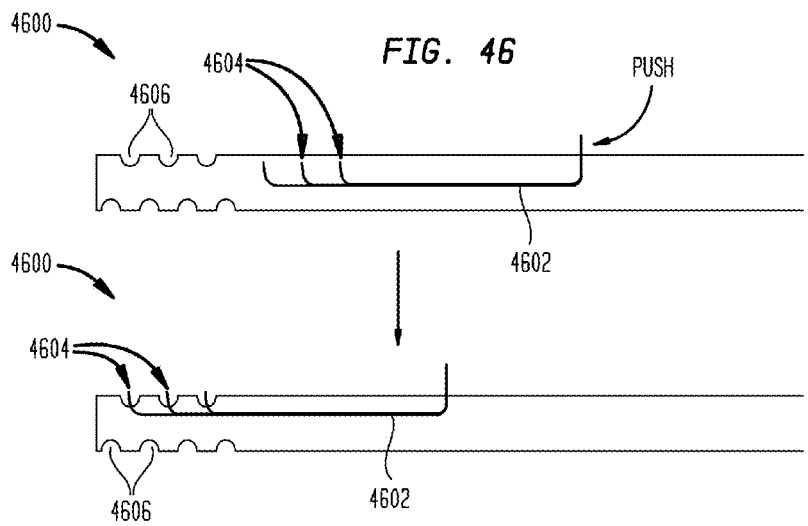

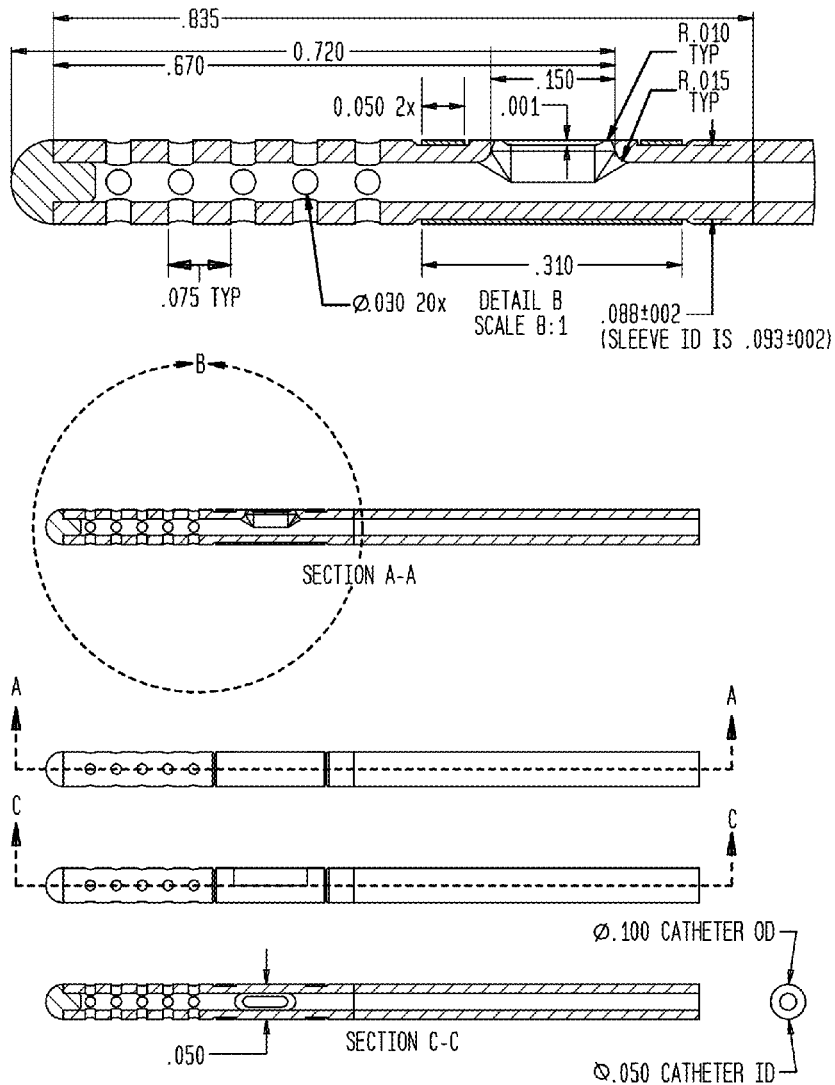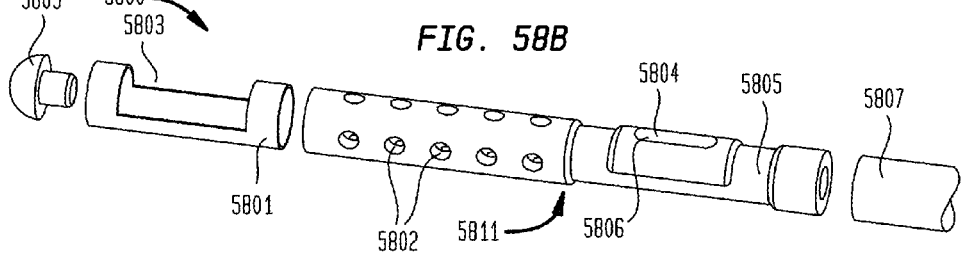

SYSTEMS AND METHODS FOR SHUNTING FLUID

CROSS-REFERENCE TO RELATED APPLICATIONS

This application claims priority to U.S. Provisional Application No. 61/981,699 filed on Apr. 18, 2014, which is hereby incorporated herein by reference in its entirety.

FIELD

The present invention relates to systems and methods for shunting fluid, e.g., shunting cerebrospinal fluid in the treatment of hydrocephalus.

BACKGROUND

Shunt systems for transport of body fluids from one region of the body to another region are generally known. For example, shunt systems are often used in the treatment of hydrocephalus to drain excess cerebrospinal fluid (CSF) from the ventricles of the brain. A typical shunt system includes a one-directional, pressure-controlled valve that is implanted beneath the skin. A ventricular catheter extends from one side of the valve to the ventricle. A drain catheter extends from the other side of the valve to a drain site, such as the abdominal cavity.

After implantation and use over extended time periods, shunt systems tend to become clogged in certain individuals. Clogging can occur due to foreign materials which collect in the narrow tubular passageways of the shunt system and in the inlet and outlet openings of such passageways. Consequently, it is often necessary to perform follow-on operations on an individual to remove the clog or replace the entire system. The inconvenience, cost, and risk of complications associated with these follow-on procedures are considerable and undesirable. Accordingly, a need exists for improved systems and methods for shunting fluid.

SUMMARY

Systems and methods are provided herein that generally involve shunting fluid, e.g., shunting cerebrospinal fluid in the treatment of hydrocephalus. Self-cleaning catheters are provided which include split tips configured such that pulsatile flow of fluid in a cavity in which the catheter is inserted can cause the tips to strike one another and thereby clear obstructions. Catheters with built-in flow indicators are also provided. Exemplary flow indicators include projections that extend radially inward from the interior surface of the catheter and which include imageable portions (e.g., portions which are visible under magnetic resonance imaging (MRI)). Movement of the flow indicators caused by fluid flowing through the catheter can be detected using MRI, thereby providing a reliable indication as to whether the catheter is partially or completely blocked. Systems and methods for flushing a shunt system are also disclosed herein, as are various systems and methods for opening auxiliary fluid pathways through a shunt system.

In some embodiments, a flusher includes a body that defines a collapsible flush dome; a passive flow path that extends between an upstream port and a downstream port, at least a portion of the flow path being defined by a pinch tube that extends across an exterior surface of the flush dome; and a valve having a first position in which the flush dome is not in fluid communication with the upstream port or the passive flow path and a second position in which the flush dome is in fluid communication with the upstream port and the passive flow path; wherein application of a force to the pinch tube is effective to collapse the pinch tube to block the passive flow path and to collapse the dome to move the valve to the second position and flush fluid through the upstream port.

The valve can include a valve body that is compressed against a valve seat by an adjustment disc such that rotation of the adjustment disc is effective to change a threshold opening pressure of the valve. The adjustment disc can be threadably mounted in a valve cartridge in which the valve body is disposed. At least a portion of the flush dome can be defined by a refill plate having a refill valve mounted therein. The refill valve can have a first position in which the passive flow path is not in fluid communication with the flush dome and a second position in which the passive flow path is in fluid communication with the flush dome. Collapsing the flush dome can be effective to hold the refill valve in the first position. The refill plate can mechanically interlock with the body. The refill plate can define an outer lip that is received within a recess formed in the body such that the lip is surrounded on at least four sides by the body. A longitudinal axis of the body can be substantially perpendicular to a longitudinal axis of the upstream port and a longitudinal axis of the downstream port. A flush channel extending between the flush dome and the valve can include a connection formed by a barbed fitting. The flusher can include a ventricle catheter in fluid communication with the upstream port. The catheter can include a primary fluid inlet port through which fluid external to the catheter can flow into an inner lumen of the catheter; an auxiliary fluid inlet port covered by a membrane such that fluid external to the catheter cannot flow through the auxiliary inlet port; and the membrane can be configured to rupture when a predetermined threshold force is applied to the membrane by fluid in the inner lumen of the catheter to open the auxiliary fluid inlet port and allow fluid to flow therethrough. The auxiliary fluid inlet port can include a rectangular slot with rounded corners. The flusher can include a stiffening sleeve disposed over the membrane. The stiffening sleeve can include a window that is aligned with the auxiliary fluid inlet port of the catheter. The stiffening sleeve can be mounted in a recess formed in the catheter such that the outer surface of the stiffening sleeve sits flush with the outer surface of the catheter.

In some embodiments, a flusher includes a body that defines a collapsible flush dome; a passive flow path that extends between an upstream port and a downstream port; and a valve comprising a valve body compressed against a valve seat by a threaded adjustment disc, the valve having a closed position in which the flush dome is not in fluid communication with the upstream port via the valve and an open position in which the flush dome is in fluid communication with the upstream port via the valve; wherein a threshold pressure required to transition the valve from the closed position to the open position is adjustable by rotating the threaded adjustment disc with respect to the body.

In some embodiments, a method of flushing a shunt system includes, in a single motion, applying a force to a flusher at a single contiguous contact area to collapse a flush dome of the flusher and to close off a connection to a downstream portion of the shunt system; wherein collapsing the flush dome is effective to release a cough of pressurized fluid through an upstream portion of the shunt system. The cough of fluid can clear an obstruction from a catheter in fluid communication with the flusher. The cough of fluid can open an auxiliary flow path through a catheter in fluid communication with the flusher.

In some embodiments, a catheter for shunting fluid built up within a skull of a patient is provided that includes an elongate tubular body having proximal and distal ends, first and second flexible tips extending from the distal end of the elongate body and having one or more fluid passageways extending therethrough, a plurality of fluid ports formed in the first and second tips, and a coupling member configured to hold the first and second tips in a position adjacent to one another.

The first and second flexible tips can be sized and configured for placement in a brain ventricle. The coupling member can be or can include a peelable sheath disposed around the first and second tips. The coupling member can be or can include a seamlessly removable insertion sheath disposed around the first and second tips. The coupling member can be or can include a bioabsorbable adhesive disposed between the first and second tips. The coupling member can be or can include a stylet or cannula disposed around the first and second tips. The first and second tips can each have a D-shaped cross-section. The first and second tips can together form a circular cross-section when coupled to one another by the coupling member. The first and second tips can each have a circular cross-section. The plurality of fluid ports can be formed in a helical pattern through sidewalls of the first and second tips. Pulsatile flow of fluid in which the first and second tips are disposed can be effective to cause the first and second tips to strike one another, thereby dislodging obstructions from the first and second tips. The catheter can include a plurality of shrouds, each shroud being disposed over a respective one of the plurality of fluid ports. The plurality of shrouds can be formed as hollow quarter spheres.

At least one of the first and second tips can include an embedded microsensor. The embedded microsensor can be or can include at least one of an interrogatable sensor, a pressure sensor, a flow sensor, a tilt sensor, an accelerometer sensor, a glutamate sensor, a pH sensor, a temperature sensor, an ion concentration sensor, a carbon dioxide sensor, an oxygen sensor, and a lactate sensor. The embedded microsensor can be or can include a pressure sensor that supplies an output indicative of a pressure in the environment surrounding the first and second tips to a valve to control a fluid flow rate through the valve. At least one of the first and second tips can contain a quantity of a drug, can be coated with a drug, or can be impregnated with a drug. The drug can be or can include at least one of an antibacterial agent, an anti-inflammatory agent, a corticosteroid, and dexamethasone. The first and second tips can be formed from a polymeric composition.

In some embodiments, a shunt for draining fluid built up within a skull of a patient is provided that includes a catheter having an elongate tubular body having proximal and distal ends, first and second flexible tips extending from the distal end of the elongate body and having one or more fluid passageways extending therethrough, a plurality of fluid ports formed in the first and second tips, and a coupling member configured to hold the first and second tips in a position adjacent to one another. The shunt can further include a skull anchor coupled to the proximal end of the elongate tubular body, the skull anchor including an injection port through which fluid can be supplied to or withdrawn from the elongate tubular body. The shunt can further include a drain catheter extending from the skull anchor, and a one-directional, pressure controlled valve disposed in line with at least one of the catheter and the drain catheter.

In some embodiments, a method of shunting body fluid is provided that includes inserting a catheter having first and second flexible tips extending from a distal end thereof and coupled to one another into a fluid-containing cavity such that fluid can flow out of the cavity through the catheter, and decoupling the first and second tips such that pulsatile flow of fluid within the cavity causes the first and second tips to strike one another, thereby dislodging obstructions from the first and second tips.

Decoupling the first and second tips can include at least one of removing a sheath disposed around the first and second tips, removing a stylet or cannula disposed around the first and second tips, and exposing a bioabsorbable adhesive disposed between the first and second tips to the fluid. The method can include adjusting a fluid flow rate through a valve in response to an output of a pressure sensor disposed on at least one of the first and second tips.

In some embodiments, a catheter is provided that includes an elongate tubular body having proximal and distal ends and a fluid lumen extending therethrough, and a plurality of flow-indicating projections extending radially inward from an interior surface of the fluid lumen, each of the projections having an imageable portion. At least the imageable portions of the projections can be configured to move relative to the fluid lumen when fluid is flowing through the fluid lumen and to remain stationary relative to the fluid lumen when fluid is not flowing through the fluid lumen.

The projections can each include a first end fixed to the interior surface of the fluid lumen and a second end free to move relative to the interior surface of the fluid lumen. The imageable portions can be disposed at the second free ends of the projections. The projections can be formed by advancing the projections through openings pierced through a sidewall of the elongate tubular body and then sealing the openings. The imageable portions can be formed from a radiopaque material. The imageable portions can be formed from a metallic material. The imageable portions can be formed from a material that is visible under magnetic resonance imaging (MRI). The projections can be flexible. The projections can be disposed throughout the length of the elongate tubular body. The projections can be grouped in one or more clusters formed at discrete locations within the elongate tubular body.

In some embodiments, a method of determining whether fluid is flowing through a fluid lumen of an implanted catheter is provided. The method can include capturing one or more images of the catheter and a plurality of flow-indicating projections extending radially inward from an interior surface of the fluid lumen, each of the projections having an imageable portion. The method can also include determining that fluid is flowing through the fluid lumen when the images indicate that the imageable portions are moving relative to the fluid lumen, and determining that fluid is not flowing through the fluid lumen when the images indicate that the imageable portions are stationary relative to the fluid lumen. The images can be at least one of magnetic resonance images, computed tomography images, positron emission tomography images, and fluoroscopic images.

In some embodiments, a catheter is provided that includes an elongate body having proximal and distal ends and a plurality of independent fluid lumens extending through at least a portion thereof, and a plurality of fluid openings formed in a sidewall of the elongate body, each fluid opening being in fluid communication with one of the plurality of fluid lumens. The fluid openings can be formed such that fluid openings that are in fluid communication with different ones of the plurality of independent fluid lumens face in different directions. The catheter can include a conical tip formed at the distal end of the elongate body, the conical tip having a plurality of fluid openings formed therein, each of the fluid openings being in fluid communication with one or more of the plurality of fluid lumens.

In some embodiments, a flusher is provided that includes a body having an upstream port and a downstream port, and a flush channel extending from a ventricle channel and a drain channel to a dome, the ventricle channel extending from the upstream port to the flush channel and the drain channel extending from the downstream port to the flush channel. The flusher also includes a valve disposed in the flush channel having a first position in which the ventricle channel and the drain channel are in fluid communication with one another and the dome is not in fluid communication with the ventricle channel or the drain channel via the flush channel, and a second position in which the dome is in fluid communication with the ventricle channel via the flush channel and the drain channel is not in fluid communication with the dome or the ventricle channel. The dome is collapsible to move the valve to the second position and flush fluid through the ventricle channel.

In some embodiments, a flushing system is provided that includes a flush component having a collapsible dome, a valve component coupled to the flush component by a first catheter and having a flush valve and a flapper valve disposed therein, and a Y adapter coupled to the valve component by a second catheter and coupled to the flush component by a third catheter. The flush valve is configured to open when a pressure differential across the flush valve exceeds a predetermined threshold, the flapper valve is configured to open when the flush valve opens to block fluid flow from the valve component to the Y adapter, and the dome is collapsible to create a pressure differential across the flush valve.

In some embodiments, a flusher is provided that includes a body having an upstream port and a downstream port, a ventricle channel that extends from the upstream port to a flush valve chamber, a drain channel that extends from the downstream port to a refill valve chamber, a flush channel that extends from the flush valve chamber to a dome, a refill channel that extends from the refill valve chamber to the dome, a bypass channel that extends from the flush valve chamber to the refill valve chamber, a flush valve disposed in the flush valve chamber and configured to allow fluid communication between the flush channel and the ventricle channel when a pressure differential cross the flush valve exceeds a predetermined threshold, a refill valve disposed in the refill valve chamber and configured to allow fluid to flow from the bypass channel into the refill channel and prevent fluid from flowing from the refill channel into the bypass channel, and a bypass valve disposed in the bypass channel configured to prevent fluid flow through the bypass channel when the fluid pressure in the bypass channel exceeds a predetermined threshold. The dome is collapsible to force fluid through the flush valve and the ventricle channel while causing the bypass valve to close to prevent fluid from being forced through the drain channel. The flusher can include a spring configured to bias the dome to an un-collapsed configuration.

In some embodiments, a catheter is provided that includes a primary fluid inlet port through which fluid external to the catheter can flow into an inner lumen of the catheter, and an auxiliary fluid inlet port covered by a membrane such that fluid external to the catheter cannot flow through the auxiliary inlet port. The membrane is configured to rupture when a predetermined threshold force is applied to the membrane by fluid in the inner lumen of the catheter to open the auxiliary fluid inlet port and allow fluid to flow therethrough. The auxiliary fluid inlet port can be or can include a rectangular slot with rounded corners. The primary fluid inlet port can include at least one slit extending therethrough such that the periphery of the inlet port is configured to deform outwards when the catheter is flushed.

The present invention further provides devices, systems, and methods as claimed.

BRIEF DESCRIPTION OF THE DRAWINGS

The invention will be more fully understood from the following detailed description taken in conjunction with the accompanying drawings, in which:

FIG. 12 is a sectional view of a flusher with a ball and spring valve;

FIG. 16 is a sectional view of a flusher with a stem;

FIG. 17 is a sectional view of a flusher with a bulb and wedge flapper valve;

FIG. 20A is a sectional view of a flusher with a lever and linkage valve, shown with the valve in a first position;

FIG. 20B is a sectional view of the flusher of FIG. 20A, shown with the valve in a second position;

FIG. 21A is a sectional view of a flusher with a flapper and recess valve, shown with the valve in a first position;

FIG. 21B is a sectional view of the flusher of FIG. 21A, shown with the valve in a second position;

FIG. 25A is a sectional view of a flusher with a piston and spring valve, shown with the valve in a first position;

FIG. 25B is a sectional view of the flusher of FIG. 25A, shown with the valve in a second position;

FIG. 44A is a sectional view of a catheter having a bellows portion before a flushing operation;

FIG. 44B is a sectional view of the catheter of FIG. 44A after a flushing operation;

FIG. 45 is a sectional view of a catheter having one or more blind bores formed in a distal sidewall thereof;

FIG. 46 is a sectional view of a catheter with an arm and finger mechanism;

FIG. 58A is a sectional view of a catheter;

FIG. 58B is an exploded view of the catheter of FIG. 58A;

DETAILED DESCRIPTION

Systems and methods are provided herein that generally involve shunting fluid, e.g., shunting cerebrospinal fluid in the treatment of hydrocephalus. Self-cleaning catheters are provided which include split tips configured such that pulsatile flow of fluid in a cavity in which the catheter is inserted can cause the tips to strike one another and thereby clear obstructions. Catheters with built-in flow indicators are also provided. Exemplary flow indicators include projections that extend radially inward from the interior surface of the catheter and which include imageable portions (e.g., portions which are visible under magnetic resonance imaging (MRI)). Movement of the flow indicators caused by fluid flowing through the catheter can be detected using MRI, thereby providing a reliable indication as to whether the catheter is partially or completely blocked. Systems and methods for flushing a shunt system are also disclosed herein, as are various systems and methods for opening auxiliary fluid pathways through a shunt system.

Certain exemplary embodiments will now be described to provide an overall understanding of the principles of the structure, function, manufacture, and use of the methods, systems, and devices disclosed herein. One or more examples of these embodiments are illustrated in the accompanying drawings. Those skilled in the art will understand that the methods, systems, and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Shunt Systems

Figure 1:
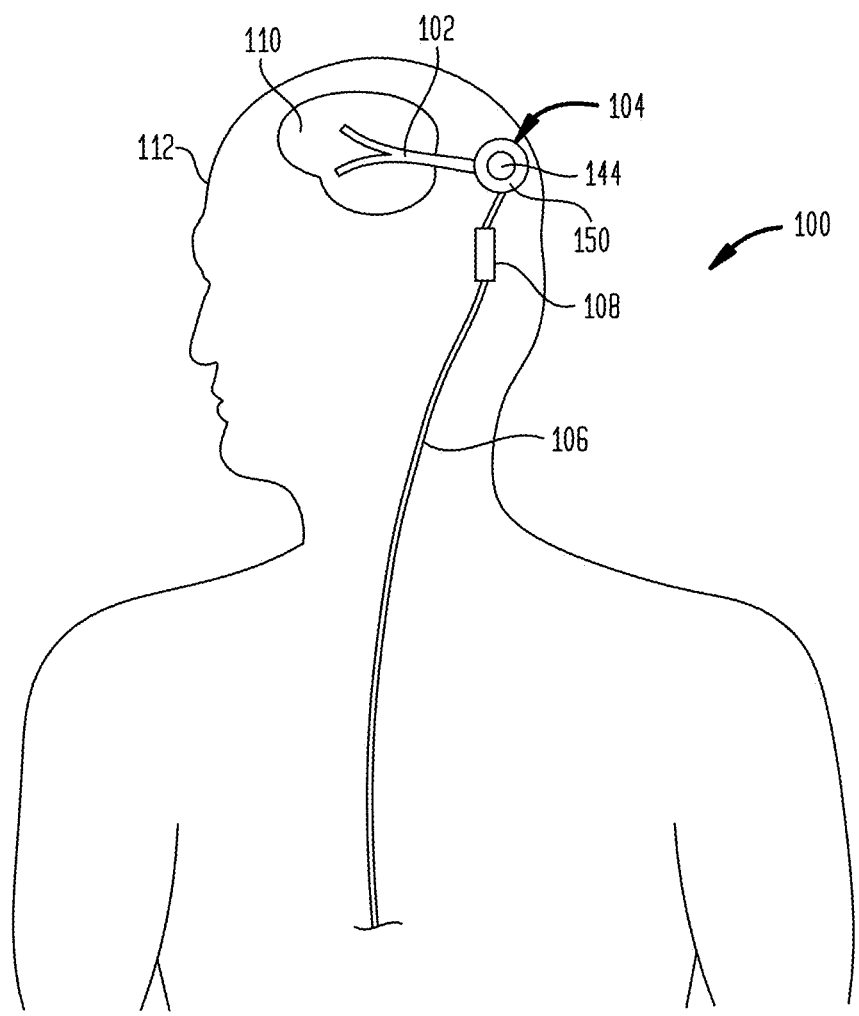
FIG. 1 is a schematic view of a shunt system implanted in a patient.

FIG. 1 illustrates one exemplary embodiment of a shunt system 100. The system generally includes a ventricular catheter 102, an anchor 104, and a drain catheter 106 with an inline valve 108. In some embodiments, the shunt system 100 can be used to treat hydrocephalus by implanting the ventricular catheter 102 such that a distal end of the catheter is disposed within a brain ventricle 110 of a patient 112. The anchor 104 can be mounted to the patient's skull, beneath the skin surface, and the drain catheter 106 can be implanted such that the proximal end of the drain catheter is disposed within a drain site, such as the abdominal cavity. The valve 108 can be configured to regulate the flow of fluid from the ventricle 110 to the drain site. For example, when fluid pressure in the ventricle exceeds the opening pressure of the valve 108, the valve can be configured to open to allow excess fluid to drain out of the ventricle 110. When the fluid pressure drops to an acceptable level, the valve 108 can be configured to close, thereby stopping further draining of fluid.

It will be appreciated that the arrangement and features of the system 100 shown in FIG. 1 is merely exemplary, and that several other variations are possible. For example, the valve 108 can be disposed distal to the anchor 104 instead of proximal thereto as shown. In other embodiments, the valve 108 can be integral to the anchor 104 or the anchor can be omitted altogether.

Figure 2:
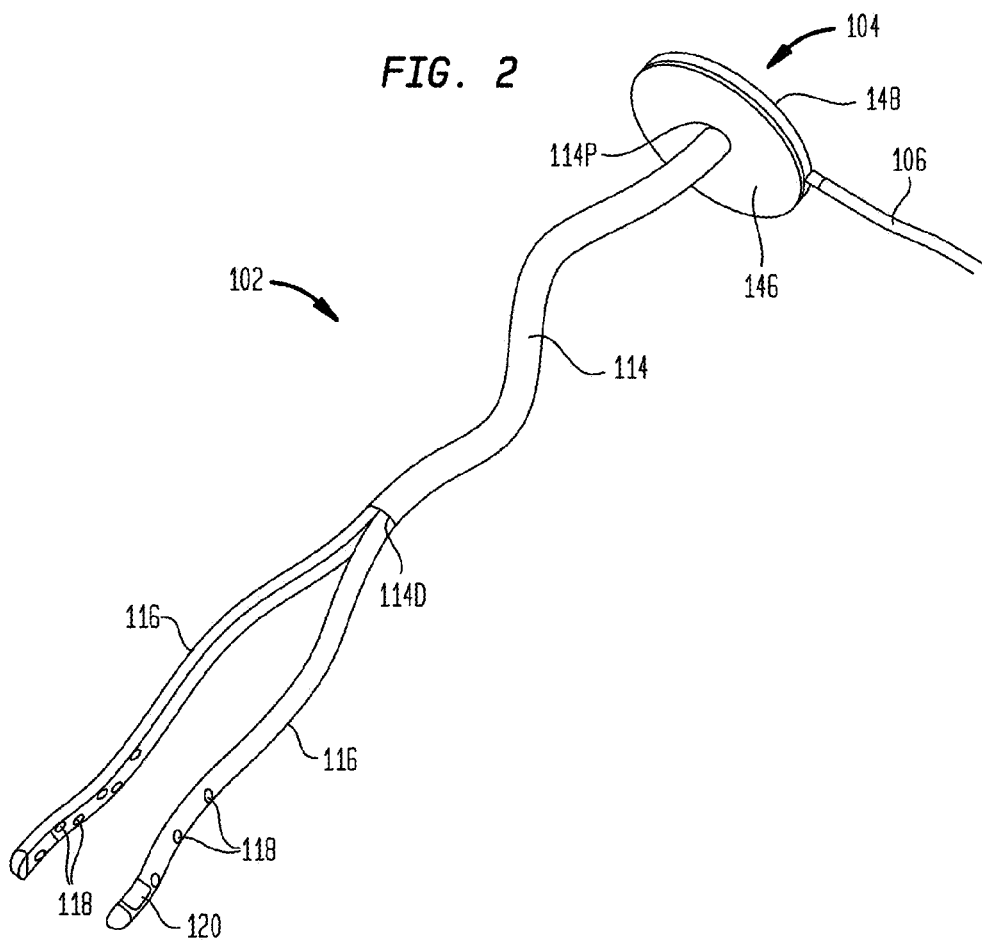
FIG. 2 is a perspective view of a ventricular catheter and skull anchor.

The shunt system 100 can include any of a variety of catheters, including single lumen catheters, multi-lumen catheters, and split-tip catheters. As shown in FIG. 2, the illustrated split-tip ventricular catheter 102 includes an elongate tubular body 114 having proximal and distal ends 114P, 114D. The catheter 102 also includes first and second flexible tips 116 extending from the distal end 114D of the body 114. While two tips 116 are illustrated, it will be appreciated that the catheter 102 can include any number of tips (e.g., three, four, five, six, and so forth). Each of the first and second tips 116 can have one or more discrete or independent fluid passageways extending therethrough. The fluid passageways can remain separate from one another throughout the entire length of the catheter 102, or one or more of the fluid passageways can merge, e.g., at the junction between the first and second tips 116 and the elongate body 114.

A plurality of fluid ports 118 can be formed in each of the first and second tips 116. The ports 118 can be arranged in any of a variety of configurations. For example, the fluid ports 118 can be arranged in a helical pattern through the sidewalls of the first and second tips 116. Alternatively, or in addition, some or all of the fluid ports 118 can be arranged in a linear pattern, in a circular pattern, and/or as open terminal distal ends of the first and second tips 116. In an exemplary embodiment, each of the first and second tips can include one to twelve fluid ports. The diameter of the fluid ports can be between about 0.1 mm and about 2.5 mm. The cross-sectional area of the fluid ports can be between about 1 $mm^2$ and about 3 $mm^2$. In some embodiments, the fluid ports can be progressively larger in diameter towards the distal end of the catheter to equalize or balance the flow through the ports. Sizing the ports in this manner can prevent localized areas of high or low flow that might otherwise occur with equally-sized ports, and thereby reduce the likelihood of a clog developing.

One or more of the tips 116 can include an embedded sensor 120. The sensor 120 can include temperature sensors, flow sensors, pH sensors, pressure sensors, oxygen sensors, tension sensors, interrogatable sensors, tilt sensors, accelerometer sensors, glutamate sensors, ion concentration sensors, carbon dioxide sensors, lactate sensors, neurotransmitter sensors, or any of a variety of other sensor types, and can provide feedback to a control circuit which can in turn regulate the drainage of fluid through the system 100 based on one or more sensed parameters. A sensor wire (not shown) can extend from the sensor 120 to an implantable control unit, and/or the sensor can wirelessly communicate the sensor output to an extracorporeal control unit. The embedded microsensor 120 can be a pressure sensor that supplies an output indicative of a pressure in the environment surrounding the first and second tips 116 to the valve 108 to control a fluid flow rate through the valve.

At least a portion of the ventricular catheter 102 (e.g., the first and second tips 116) or any other component of the system 100 can contain or can be impregnated with a quantity of a drug. Alternatively, or in addition, a surface of said portion can be coated with a drug. Exemplary drugs include anti-inflammatory components, anti-bacterial components, drug permeability-increasing components, delayed-release coatings, and the like. In some embodiments, one or more portions of the system 100 can be coated or impregnated with a corticosteroid such as dexamethasone which can prevent swelling around the implantation site and disruptions to the fluid drainage function that can result from such swelling.

Figure 3:
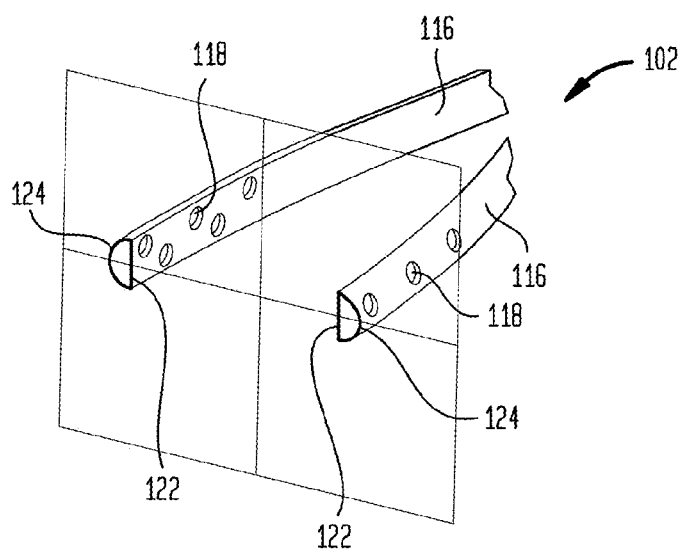
FIG. 3 is a sectional perspective view of the ventricular catheter of FIG. 2.
Figure 4:
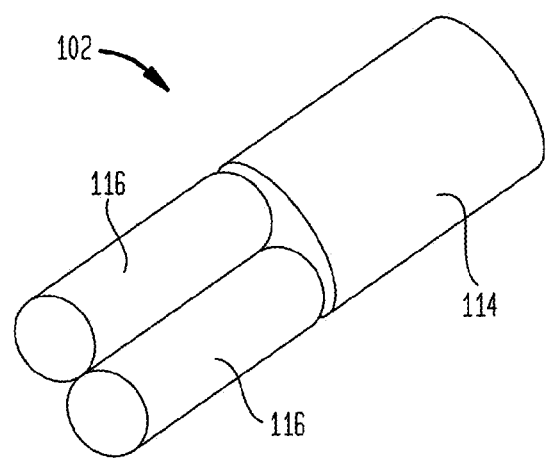
FIG. 4 is a perspective view of a ventricular catheter having flexible tips with circular cross-sections.

As shown in FIG. 3, the first and second tips 116 can each have a D-shaped cross-section. In other words, the first and second tips 116 can each have a substantially planar sidewall 122 and a substantially hemi-cylindrical sidewall 124. The orientation of the D-shape of the first tip can be opposite to that of the second tip, such that the first and second tips 116 together form a circular cross-section when they are coupled to one another or when they longitudinally abut one another. The first and second tips 116 can also have other cross-section shapes. For example, as shown in FIG. 4, the first and second tips 116 can each have a circular cross-section.

The ventricular catheter 102, and in particular the first and second flexible tips 116, can be sized and configured for placement in a brain ventricle. For example, in some embodiments, the body 114 of the ventricular catheter 102 can have a length between about 2 cm and about 15 cm and an outside diameter between about 1 mm and about 5 mm. In some embodiments, the first and second tips 116 can have a length between about 3 cm and about 15 cm and/or a cross-sectional area between about 1 mm$^2$ and about 7 mm$^2$.

Figure 5:
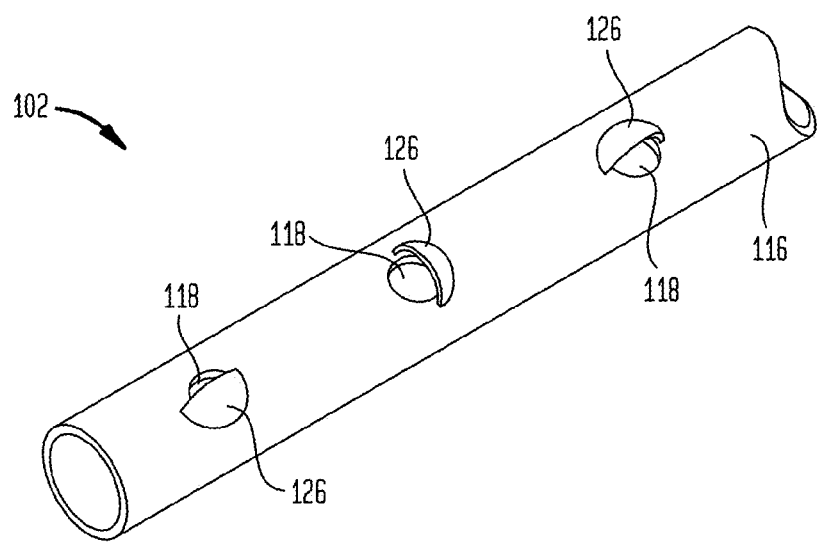
FIG. 5 is a perspective view of a ventricular catheter with clog-preventing shrouds.

One or more of the fluid ports 118 in the ventricular catheter 102 can include shrouds or covers 126 to reduce the tendency for the port to become clogged. For example, as shown in FIG. 5, the catheter 102 can include shrouds 126 that extend at least partially over the fluid ports 118 formed in each tip 116. In some embodiments, the shrouds 126 can be formed as sections of a hollow sphere, e.g., hollow quarter spheres as shown. The shrouds 126 can have a variety of other shapes, including sections of a cylinder, sections of a cube, and so forth. The shrouds 126 can be placed in any of a variety of orientations. For example, the shrouds 126 can be placed in random orientations, in alternating orientations, in a repetitive sequence of orientations, and so forth. In operation, the shrouds 126 can prevent ingrowth of choroid plexus into the fluid ports 118 and/or accumulation of other tissue, debris, or material that might block the fluid ports.

Figure 6:
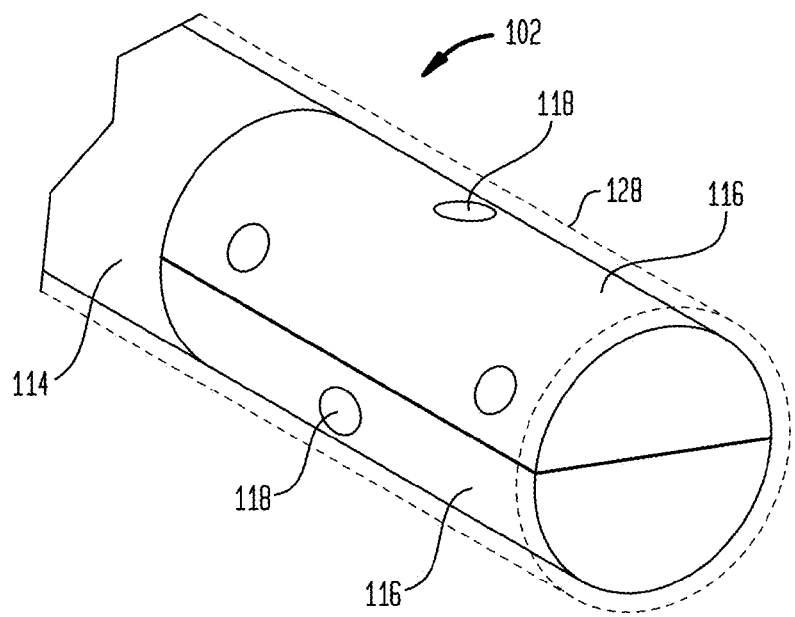
FIG. 6 is a perspective view of a ventricular catheter with a coupling member shown in phantom.

As shown in FIG. 6, the ventricular catheter 102 can include a coupling member 128 configured to hold the first and second tips 116 in a position adjacent to one another, e.g., in longitudinal abutment with one another. The coupling member 128 can be disposed around the first and second tips 116 as shown, and thereby configured to retain the tips in a position proximate to one another. Exemplary coupling members 128 can include a seamlessly removable insertion sheath, a peelable sheath, a stylet, or a cannula disposed around the first and second tips 116 and accessible for removal from a proximal end of the catheter 102. The coupling member can also be in the form of an adhesive disposed between the first and second tips 116. For example, in the case of D-shaped tips 116, the planar sidewalls 122 of the first and second tips can be adhered to one another. The adhesive or at least the adhesive strength thereof can be configured to degrade when the adhesive is exposed to conditions within the body of a patient (e.g., certain temperatures, pHs, chemical compositions, and so forth). In exemplary embodiments, the adhesive is biocompatible and bioabsorbable and configured to rapidly degrade when exposed to cerebrospinal fluid in a patient's ventricle. Exemplary adhesives include, e.g., polylactides, polyglycolides, polylactones, polyorthoesters, polyanhydrides, proteins, starches, sugars and copolymers and/or combinations thereof.

Figure 7:
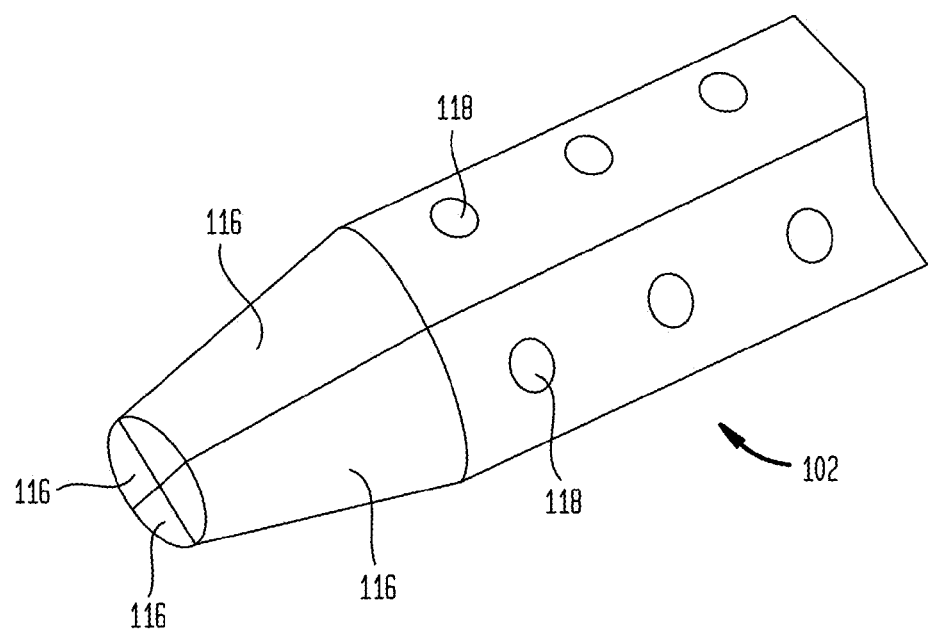
FIG. 7 is a perspective view of a ventricular catheter with a conical tip.

The distal-most tip of the catheter 102 can have a variety of shapes and configurations. For example, the distal ends of the first and second tips 116 can be open or closed, or can be primarily closed with one or more openings formed therein. By way of further example, the distal ends of the first and second tips 116 can together form a section of a sphere (e.g., as shown in FIG. 2), can be straight cut to form a blunt end (e.g., as shown in FIG. 6), can be slash cut, or can form a section of a cone (e.g., as shown in FIG. 7).

Figure 8:
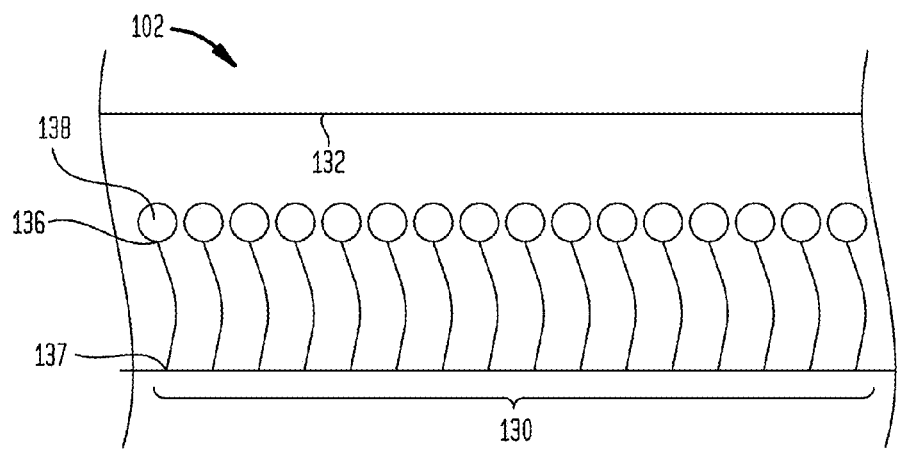
FIG. 8 is a sectional side view of a ventricular catheter with flow-indicating projections disposed therein.

The ventricular catheter 102 can include various features for indicating whether or to what degree fluid is flowing through the catheter. Such features can advantageously allow for accurate detection or confirmation of blockages or reduced flow conditions within the catheter 102, without requiring removal of the catheter. For example, as shown in FIG. 8, the catheter 102 can include a plurality of flow-indicating projections 130 disposed therein. The projections can be formed from any of a variety of flexible materials to allow them to flex or bend. The projections can extend radially inward from an interior surface 132 of a fluid lumen of the catheter 102, such that a first end 134 of each projection 130 is fixed to the interior surface 132 and a second end 136 of each projection is free to move relative to the interior surface when the projection flexes or bends.

Figure 9:
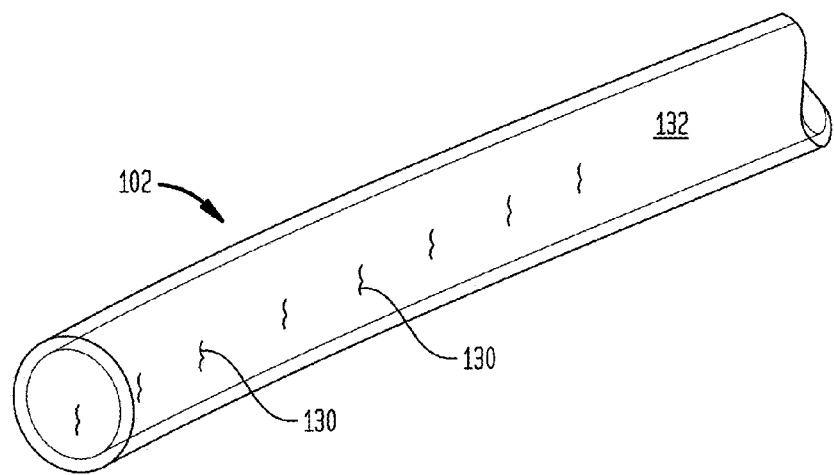
FIG. 9 is a sectional perspective view of a ventricular catheter having flow-indicating projections disposed therein.

The projections 130 can be imageable or can include one or more imageable portions. For example, the projections 130 can include imageable portions 138 disposed at the second free ends 136 of the projections. The imageable portions 138 can be visible under one or more imaging techniques, such as magnetic resonance imaging (MRI), computed tomography (CT) imaging, positron emission tomography (PET) imaging, and fluoroscopic imaging. The imageable portions 138 can thus be formed from a radiopaque material, a metallic material, a material that is visible under magnetic resonance imaging, or any of a variety of other materials visible under the imaging techniques listed above. As shown in FIG. 9, in some embodiments, the entirety of each projection 130 can be imageable.

The projections 130 can be coupled to the catheter 102 by piercing the projections through a sidewall of the catheter and advancing the projections through the pierced opening. The opening can then be sealed using any of a variety of sealing compounds, including silicone glue or other adhesives. It will be appreciated that this is only one of many ways of fixing the projections 130 to the catheter 102, and therefore that various other techniques can be used instead or in addition.

The projections 130 can be disposed throughout the length of the catheter 102 (e.g., in the elongate tubular body 114 and/or the distal tips 116 of the catheter), or can be grouped in one or more clusters formed at discrete locations within the catheter. The density of the projections 130 (e.g., the number of projections disposed in a given surface area of the interior of the catheter) can be selected based on the size of the fluid lumen in which the projections are disposed.

In use, at least the imageable portions 138 of the projections 130 can be configured to move relative to the fluid lumen when fluid is flowing through the fluid lumen and to remain stationary relative to the fluid lumen when fluid is not flowing through the fluid lumen. The projections 130 can thus act as reef or thread-like structures that sway back and forth as fluid flows through the catheter 102. This movement of the projections 130 can be observed using the imaging techniques listed above to assess whether and to what degree fluid is flowing through the shunt system 100.

Figure 10:
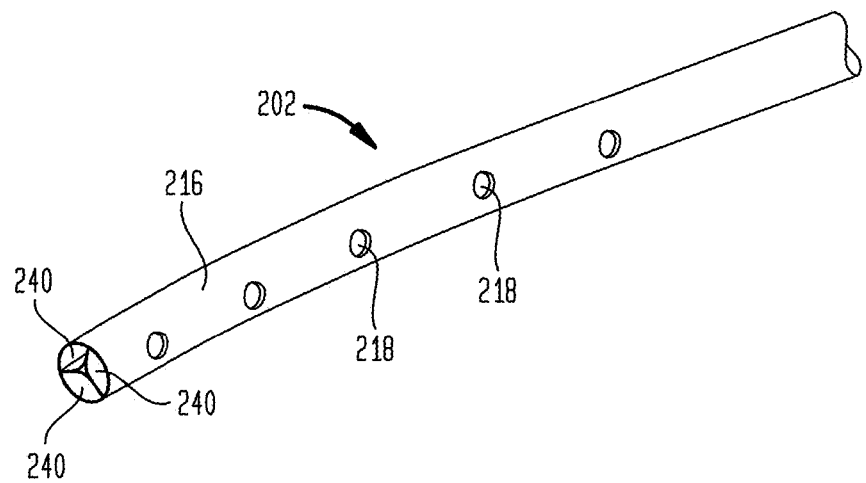
FIG. 10 is a perspective view of a ventricular catheter having multiple independent fluid lumens.
Figure 11:
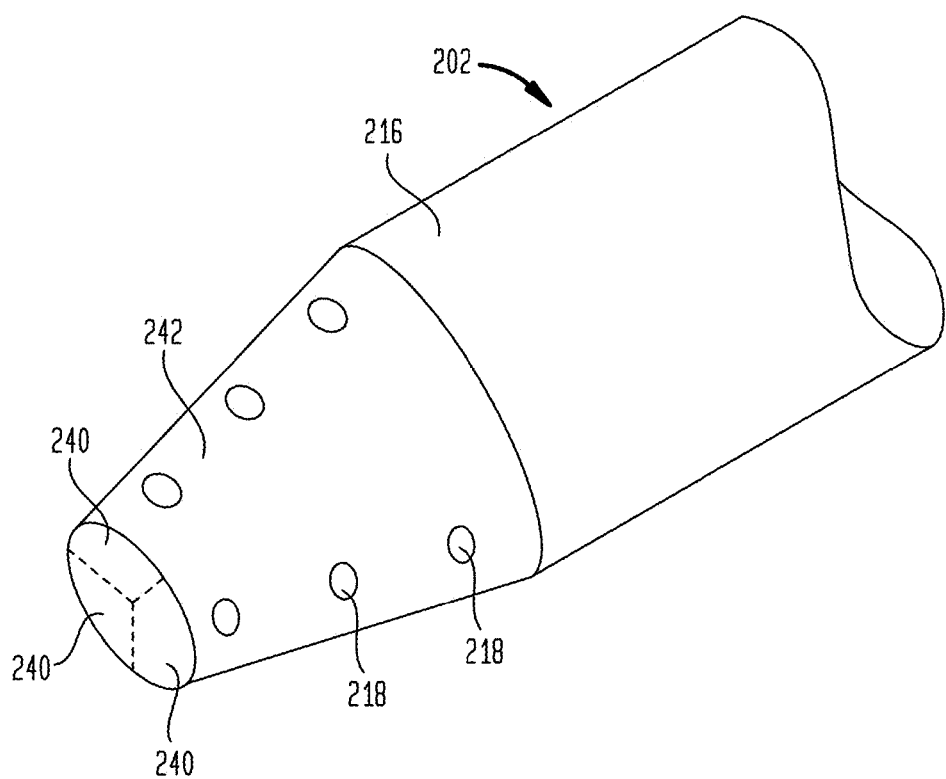
FIG. 11 is a perspective view of a ventricular catheter having a conical tip.

FIG. 10 illustrates another exemplary embodiment of a ventricular catheter 202. Except as indicated below, the structure and operation of the catheter 202 is identical to that of the catheter 102 described above, and therefore a detailed description thereof is omitted here for the sake of brevity. Instead of multiple flexible tips, the multi-lumen catheter 202 includes a single tip 216 with a plurality of independent fluid lumens 240 extending therethrough. The fluid lumens 240 can remain independent throughout the length of the catheter 202, or can merge into one or more common fluid lumens at a location spaced a distance from the distal end of the catheter. While three fluid lumens 240 are shown, it will be appreciated that virtually any number of fluid lumens can be included. For example, the catheter 202 can include between two and five fluid lumens 240. Each of the independent fluid lumens 240 can include one or more fluid openings 218 formed in a sidewall thereof through which fluid to be shunted can flow into the fluid lumens. The distal ends of the fluid lumens 240 can be open as shown, or can be fully or partially closed. In some embodiments, the distal end of the catheter 202 can form a section of a sphere or cone 242, e.g., as shown in FIG. 11, which can have one or more fluid openings 218 formed therein. Provision of multiple independent fluid lumens 240 can advantageously provide redundancy in the event that one or more of the fluid lumens becomes clogged. Further, if the source of clogging is directional, i.e., the source arrives at the catheter in predominately one direction, then it is more likely that if one lumen becomes clogged, the other lumens will continue to operate as the openings leading into those lumens will be facing in different directions from the lumen that became clogged. Also, providing multiple fluid lumens 240 allows for a flow rate comparable to that of a single lumen catheter while permitting the cross-sectional area of each fluid lumen 240 to be made small as compared to a single lumen catheter. The smaller dimensions of the multiple lumens 240 can prevent foreign material or choroid plexus ingrowth from entering the lumen and thereby reduce the potential for clogging.

The catheters 102, 106, 202 and the coupling member 128 can be formed from any of a variety of materials, including polymeric compositions, parylene compositions, silastic compositions, polyurethane compositions, PTFE compositions, silicone compositions, and so forth.

Referring again to FIGS. 1 and 2, the system 100 can include an anchor 104 to which the ventricular catheter 102 can be coupled. The anchor 104 can be secured to the patient's skull, beneath the skin, to secure the proximal end of the ventricular catheter 102 and to provide access to the system 100. For example, the anchor 104 can include a reservoir in fluid communication with the ventricular catheter 102 and covered by a septum 144. A needle can be used to pierce the skin and the septum 144 and supply fluid to the reservoir and to extract fluid from the reservoir. Fluid communication between the reservoir and the patient's ventricle 110 via the ventricular catheter 102 can be used to inject one or more drugs, therapeutic agents, etc. into the ventricle. In embodiments in which the catheter 102 includes multiple independent lumens, one or more lumens can be dedicated for drug delivery to the ventricle 110 while one or more other lumens can be dedicated for fluid drainage from the ventricle.

In the illustrated embodiment, the anchor 104 is substantially disk-shaped and includes a concave distal surface 146 configured to substantially conform to the contour of the patient's skull. The proximal surface 148 of the anchor 104 can include a retaining ring 150 that extends around the circumference of the anchor and holds the septum 144 in place. The ventricular catheter 102 can couple to a center point of the distal surface 146. A drain catheter 106 can extend laterally out from the anchor 104 to the downstream valve 108 and, ultimately, to the drain site. The anchor 104 can thus provide a rigid coupling between one or more implanted catheters 102, 106 and facilitate a 90 degree turn in the fluid path out of the ventricle 110.

The drain catheter 106 extending out of the anchor 104 can be coupled to a valve 108 configured to selectively open to release fluid from the ventricle 110. In general, the valve 108 can include an inlet port, an outlet port, and a biased flapper disposed therebetween. When pressure exceeds the bias strength of the flapper, the flapper can open to allow fluid communication between the inlet port and the outlet port. The valve 108 can also be adjustable, e.g., via an externally-applied magnetic field. Shunt valves with adjustable pressure settings are well known in the art, and are disclosed for example in U.S. Pat. No. 3,886,948, issued on Jun. 3, 1975 and entitled "VENTRICULAR SHUNT HAVING A VARIABLE PRESSURE VALVE," the entire contents of which are incorporated herein by reference.

The valve 108 can be disposed inline relative to the drain catheter 106, e.g., such that a first portion of the drain catheter 106 is fluidly coupled to the inlet port of the valve 108 and a second portion of the drain catheter 106 is fluidly coupled to the outlet port of the valve 108. The drain catheter 106 can thus be conceptualized as two separate catheters, one extending between the anchor 104 and the valve 108 and another extending between the valve and the drain site. The drain catheter 106 can extend such that its proximal end is disposed within a drain site in the patient's body, e.g., the abdominal cavity. The drain catheter 106 can be a traditional cylindrical catheter having a single fluid lumen extending therethrough. Alternatively, the drain catheter 106 can include a plurality of discrete fluid lumens extending along at least a portion of its length. The proximal end of the drain catheter 106 can have a split-tip design and/or can otherwise be configured in the same manner as the distal end of the ventricular catheters 102, 202 described above.

In use, the shunt system 100 can be used to transfer fluid from one location to another location. When used in a patient's body, the shunt system 100 can be used to treat any of a variety of diseases, conditions, or ailments. For example, the system 100 can be used to treat hydrocephalus and/or to shunt fluid built up within a patient's skull by implanting the ventricular catheter 102 such that a distal end of the catheter is disposed within a brain ventricle 110 of the patient 112. The anchor 104 can be mounted to the patient's skull, beneath the skin surface, and the drain catheter 106 can be implanted such that the proximal end of the drain catheter is disposed within a drain site, such as the abdominal cavity.

Once the distal end of the ventricular catheter 102 is disposed within the ventricle 110, the coupling member 128 can be removed (or permitted to degrade in the case of an adhesive) to decouple the first and second tips 116 from one another and allow the tips to separate. As noted above, the coupling member 128 can be or can include a peelable sheath, a stylet, or a cannula which can be accessible for removal from a proximal end of the catheter 102. In other words, the coupling member 128 can be pulled proximally by a surgeon or other user to remove the coupling member once the distal tip of the catheter 102 is placed in the desired location.

Once decoupled, pulsatile flow of fluid within the ventricle 110 can be effective to cause the first and second tips 116 to strike one another. The forces applied to the tips 116 as a result of such striking can dislodge obstructions from the first and second tips or the fluid ports 118 or passageways thereof, thereby preventing, reducing, or alleviating clogs. It will be appreciated that the relatively continuous pulsatile flow of fluid can persist throughout the term of treatment, providing an automatic self-cleaning and anti-clogging functionality.

As in a typical shunt system, when fluid pressure in the ventricle 110 exceeds the opening pressure of the valve 108, the valve can be configured to open to allow excess fluid to drain out of the ventricle. When the fluid pressure drops to an acceptable level, the valve 108 can be configured to close, thereby stopping further draining of fluid. In some embodiments, the output of a sensor 120 (e.g., a pressure sensor) disposed in or on one of the first and second tips 116 can be used to control operation of the valve 108. For example, an opening pressure, fluid flow rate, or other property of the valve 108 can be adjusted in response to the output of a pressure sensor 120.

In embodiments which include flow indicating features 130, a determination can be made as to whether or to what degree fluid is flowing through the fluid lumen. For example, one or more images (e.g., MRI, CT, PET, or the like) of a catheter 102 and a plurality of flow-indicating projections 130 disposed therein can be captured. An observer can then view the images and determine whether and to what degree the projections 130 are moving. For example, when the images indicate that the imageable portions 138 of the projections 130 are moving relative to the fluid lumen, it can be determined that fluid is flowing through the fluid lumen. Likewise, when the images indicate that the imageable portions 138 are stationary relative to the fluid lumen, it can be determined that fluid is not flowing through the fluid lumen and that there may be a blockage or obstruction in the shunt system.

Flushers

In some embodiments, the shunt system 100 can include a flusher for clearing obstructions from the shunt system or for opening auxiliary fluid paths through the shunt system. The flusher can be disposed between the ventricular catheter 102 and the anchor 104, between the anchor 104 and the valve 108, or between the valve 108 and the drain catheter 106. The flusher can also be formed integrally with any of the ventricular catheter 102, the anchor 104, the valve 108, and the drain catheter 106. FIGS. 12-27 and 49A-57 illustrate various exemplary flusher embodiments that can be used with a shunt system (e.g., with the shunt system 100 described above).

FIG. 12 illustrates an exemplary embodiment of a flusher 1200 with a ball and spring valve 1202. The flusher includes a body 1204 with an upstream port 1206 configured to be coupled to or placed in fluid communication with a ventricular catheter and a downstream port 1208 configured to be coupled to or placed in fluid communication with a drain catheter. The flusher 1200 also includes a dome 1210 that can be actuated, e.g., by exerting downward finger pressure on the dome through a patient's skin, to collapse or compress the dome and expel fluid therefrom. A network of fluid channels is formed in the body of the flusher, and includes a ventricle channel 1212, a drain channel 1214, a flush channel 1216, and a refill channel 1218. The ventricle channel 1212 extends from the upstream port 1206 to the flush channel 1216. The drain channel 1214 extends from the downstream port 1208 to the flush channel 1216. The flush channel 1216 extends from the ventricle and drain channels 1212, 1214 to the dome 1210. The refill channel 1218 extends from the ventricle channel 1212 to the dome 1210. It will be appreciated, however, that in other embodiments the refill channel 1218 can extend from the drain channel 1214 to the dome 1210. A one-way or check valve 1220 is disposed in the refill channel 1218. The valve 1220 is configured to prevent fluid from flowing from the dome 1210 to the ventricle channel 1212 through the refill channel, but allows fluid to flow from the ventricle channel to the dome through the refill channel.

The ball and spring valve 1202 is disposed in the flush channel 1216 to control fluid flow through the flusher 1200. The valve 1202 has at least a first position in which the ball portion of the valve 1222 seals the flush channel 1216 between the dome 1210 and the ventricle and drain channels 1212, 1214, such that the dome is not in fluid communication with the ventricle and drain channels through the flush channel. The ball 1222 can be formed from rubber, silicone, polyurethane, or other materials that can provide a seal between the ball and the flush channel 1216. The ball 1222 can also be sized to fit within the flush channel 1216 in an interference fit to enhance the seal and control the amount of force required to move the ball. In the first position, the ventricle and drain channels 1212, 1214 are in fluid communication with one another such that fluid can flow freely from the upstream port 1206 to the downstream port 1208.

The valve 1202 also has at least a second position in which the ball portion of the valve 1222 seals the drain channel 1214 and in which the dome 1210 is placed in fluid communication with the ventricle channel 1212 via the flush channel 1216. In particular, the ball portion of the valve 1222 can be seated in a spherical valve seat 1224 formed at the junction of the drain channel 1214 and the flush channel 1216. When the ball 1222 is seated in the valve seat 1224, fluid communication between the drain channel 1214 and the flush channel 1216 and between the drain channel 1214 and the ventricle channel 1212 is cut off. In addition, a clearance space is formed between the ball 1222 and the sidewall of the flush channel 1216 when the ball moves into the valve seat 1224, unsealing the flush channel and placing the dome 1210 in fluid communication with the ventricle channel 1212. The spring portion 1226 of the valve biases the ball 1222 towards the first position.

In use, the flusher 1200 generally has two operating modes. In a normal operating mode, the ball 1222 is disposed in the first position due to the bias of the spring 1226, and fluid is allowed to flow freely from the upstream port 1206 to the downstream port 1208. When the flusher 1200 is implanted in a patient as part of a shunt system, fluid is free to flow from the ventricle and through the flusher to a valve or drain catheter disposed downstream from the flusher. In the normal operating mode, the dome 1210 remains filled with fluid previously supplied to the dome through the refill channel 1218.

In a flush operating mode, a force is exerted on the dome 1210 to collapse the dome and displace fluid therefrom into the flush channel 1216. This causes the pressure above the ball 1222 to increase until the force of fluid acting on the top of the ball exceeds the spring force exerted on the bottom of the ball by the bias spring 1226 and the interference fit between the ball and the flusher channel 1216, at which point the ball moves from the first position to the second position. In some embodiments, the pressure required to move the ball 1222 from the first position to the second position is about 40 psig. When the ball moves to the second position, the pressurized fluid is suddenly released, resulting in an upstream "cough" or flush of fluid back through the ventricle channel 1212, which can be effective to clear obstructions from a ventricle catheter or other upstream component of the shunt system, or to open auxiliary flow paths as described further below. After the cough of fluid is released, the spring 1226 biases the ball 1222 back to the first position and the force applied to the dome 1210 is removed. Fluid flow through the flusher 1200 in the downstream direction then resumes, with a portion of the fluid flow diverting through the refill channel 1218 to refill the dome 1210 with fluid and return the dome to a non-collapsed configuration. The size of the refill channel 1218 can be selected to control the rate at which the dome 1210 is refilled. For example, the cross-sectional area of the refill channel 1218 can be made small to choke the flow of fluid into the dome 1210. In embodiments in which the dome 1210 has resilient properties, this can advantageously prevent the dome from quickly springing back to the non-collapsed configuration and generating a reflux action in which debris or obstructions cleared by a flushing operation are sucked back into the shunt system.

The flusher 1200 thus facilitates generation and application of a high pressure cough of fluid which flushes the ventricle side of the shunt system only. The ball and spring valve 1202 prevents the cough of fluid from travelling through the drain side of the shunt system. In other embodiments, however, the flusher 1200 can be configured to flush the drain side of the system instead or in addition.

Figure 13A:
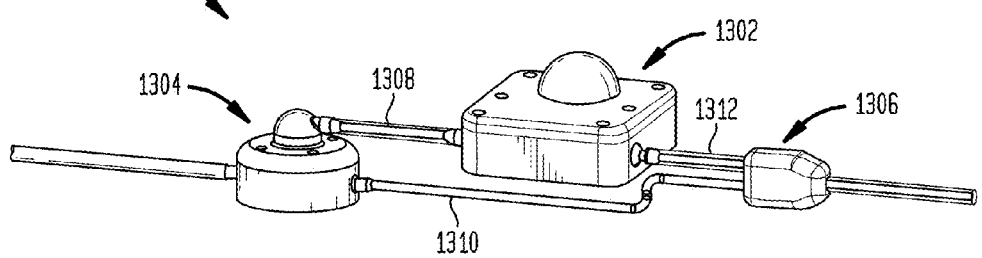
FIG. 13A is a perspective view of a flush system with a series of valves and fluid pathways.
Figure 13B:
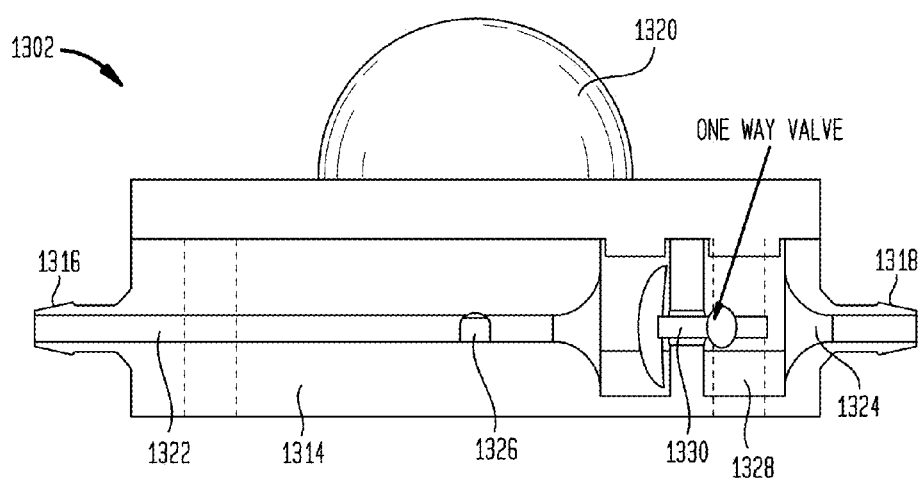
FIG. 13B is a sectional view of the flush component of the flush system of FIG. 13A.
Figure 13C:
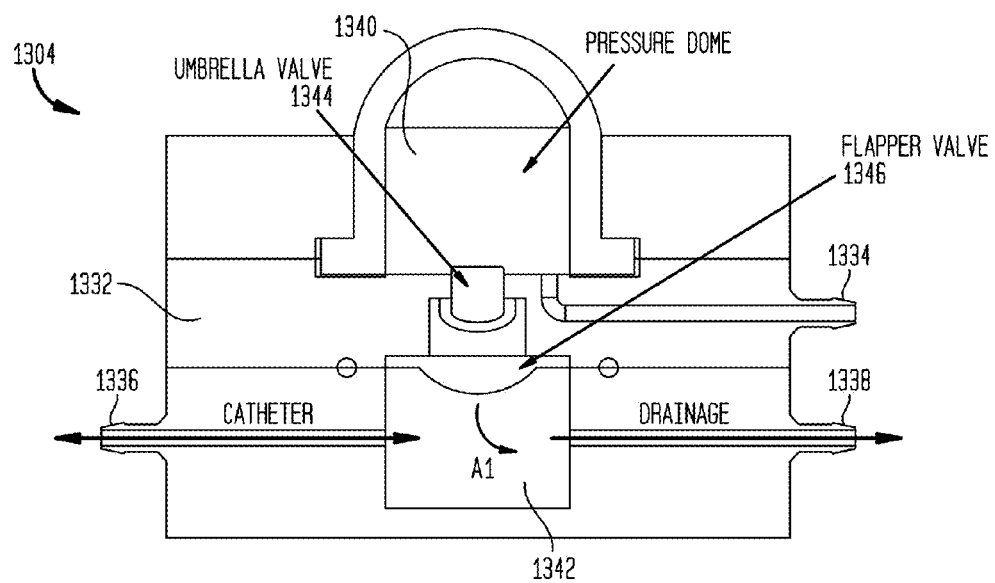
FIG. 13C is a sectional view of the valve component of the flush system of FIG. 13A.

FIGS. 13A-13C illustrate an exemplary embodiment of a dual lumen flush system 1300. The system 1300 includes a flush component 1302, a valve component 1304, and a Y adapter 1306. The system 1300 also includes a first catheter 1308 that extends from the valve component to the flush component, a second catheter 1310 that extends from the valve component to the Y adapter, and a third catheter 1312 that extends from the flush component to the Y adapter. While three separate components interconnected by catheters are shown and described, it will be appreciated that any two or more of the components can be integrated in a single package with the catheters that would ordinarily extend between said components also being integrated into the package as built-in fluid channels.

As shown in FIG. 13B, the flush component 1302 includes a body 1314 with a valve component port 1316 configured to be coupled to the valve component 1304 via the first catheter 1308 and a refill port 1318 configured to be coupled to the Y adapter 1306 via the third catheter 1312. The flush component 1302 also includes a dome 1320 that can be actuated, e.g., by exerting downward finger pressure on the dome through a patient's skin, to expel fluid from the dome. A network of fluid channels is formed in the body 1314 of the flush component 1302, and includes a valve component channel 1322, a refill channel 1324, and a flush channel 1326. The valve component channel 1322 extends from the valve component port 1316 to a cavity 1328 in which an umbrella-type one-way valve 1330 is disposed. The refill channel 1324 extends from the cavity 1328 to the refill port 1318. The flush channel 1326 extends from the dome 1320 to the valve component channel 1322. The one-way valve 1330 prevents fluid from flowing from the valve component channel 1322 to the refill channel 1324 through the cavity 1328, and allows fluid to flow from the refill channel to the valve component channel through the cavity.

As shown in FIG. 13C, the valve component 1304 includes a body 1332 with a flush component port 1334 configured to be coupled to the flush component 1302 via the first catheter 1308, an upstream port 1336 configured to be coupled to or placed in fluid communication with a ventricular catheter, and a downstream port 1338 configured to be coupled to the Y adapter 1306 via the second catheter 1310. The flush component port 1334 is coupled to an upper chamber 1340 defined by a pressure dome. The upper chamber 1340 is separated from a lower chamber 1342 by an umbrella valve 1344 and a flapper valve 1346 to control fluid flow through the flush system 1300. The flapper valve 1346 can have various configurations. In some embodiments, the flapper valve 1346 includes an integral living hinge about which the flapper valve pivots to open and close. In other embodiments, the flapper valve 1346 is coupled to the valve component body 1332 by a pivot pin about which the flapper valve pivots to open and close.

The valve component 1304 has a first configuration in which the umbrella valve 1344 and the flapper valve 1346 are both closed and the upstream port 1336 of the valve component is in fluid communication with the downstream port 1338. In the first configuration, fluid can flow freely from the upstream port 1336 to the downstream port 1338 and through the Y adapter 1306 (e.g., to a drain catheter).

The valve component 1304 also has a second configuration in which the umbrella valve 1344 opens to place the upper chamber 1340 in fluid communication with the lower chamber 1342 and the flapper valve 1346 hinges open to block fluid communication between the lower chamber 1342 and the downstream port 1338.

In use, the flush system 1300 generally has two operating modes. In a normal operating mode, the valve component 1304 is in the first configuration and fluid is allowed to flow freely from the upstream port 1336 to the downstream port 1338 and through the Y adapter 1306. When the flush system 1300 is implanted in a patient as part of a shunt system, fluid is free to flow from the ventricle through the flush system to a valve or drain catheter disposed downstream from the flush system. In the normal operating mode, the dome 1320 remains filled with fluid previously supplied to the dome through the refill channel 1324.

In a flush operating mode, a force is exerted on the dome 1320 to collapse the dome and displace fluid therefrom into the flush channel 1326 and the valve component channel 1322. The one-way valve 1330 prevents fluid from being displaced from the dome into the refill channel 1324. The pressure in the upper chamber 1340 of the valve component 1304 increases until the force of fluid acting on the top of the umbrella valve 1344 exceeds the popping threshold of the valve, at which point the valve component 1304 transitions to the second configuration. In some embodiments, the pressure required to open the umbrella valve 1344 is about 40 psig, meaning that the pressure above the valve must exceed the pressure below the valve by at least 40 psig for the valve to open. When the umbrella valve 1344 opens, the pressure is applied to the top of the flapper valve 1346, causing it to hinge open and rotate counterclockwise about a hinge axis (indicated by the arrow A1), until a domed portion of the flapper valve 1346 contacts the entrance to the downstream port 1338 and blocks fluid communication between the lower chamber 1342 and the downstream port. The pressurized fluid is also suddenly released into the lower chamber 1342, resulting in an upstream "cough" or flush of fluid back through the upstream port 1336, which can be effective to clear obstructions from a ventricle catheter or other upstream component of the shunt system. After the cough of fluid is released, a biasing force (e.g., generated by a bias spring, resilient materials, or hydraulic action) causes the flapper valve 1346 and the umbrella valve 1344 to close. As a result, fluid communication is restored between the upstream and downstream ports 1336, 1338 of the valve component. Fluid flow through the flush system 1300 in the downstream direction then resumes, with a portion of the fluid flow through the Y adapter 1306 diverting through the third catheter 1312 and into the refill channel 1324 of the flush component 1302 to refill the dome 1320 through the one-way valve 1330.

In some embodiments, the third catheter 1312 can be larger in cross-sectional area than the catheter extending from a downstream port of the Y adapter 1306, such that fluid preferentially flows through the third catheter to refill the dome 1320 before flowing out of the Y adapter to downstream components of the shunt system. For example, the downstream catheter can have an inside diameter of about 0.050 inches and the third catheter 1312 can have an inside diameter of about 0.100 inches to about 0.150 inches.

The size of the flush channel 1326, or downstream channels such as the third catheter 1312, the refill port 1318, or the refill channel 1324, can be selected to control the rate at which the dome 1320 is refilled. For example, the cross-sectional area of the flush channel 1326 can be made small to choke the flow of fluid into the dome 1320. In embodiments in which the dome 1320 has resilient properties, this can advantageously prevent the dome from quickly springing back to the non-collapsed configuration and generating a reflux action in which debris or obstructions cleared by a flushing operation are sucked back into the shunt system.

The flush system 1300 thus facilitates generation and application of a high pressure cough of fluid which flushes the ventricle side of the shunt system only. The flapper valve 1346 prevents the cough of fluid from travelling through the drain side of the shunt system.

Figure 14A:
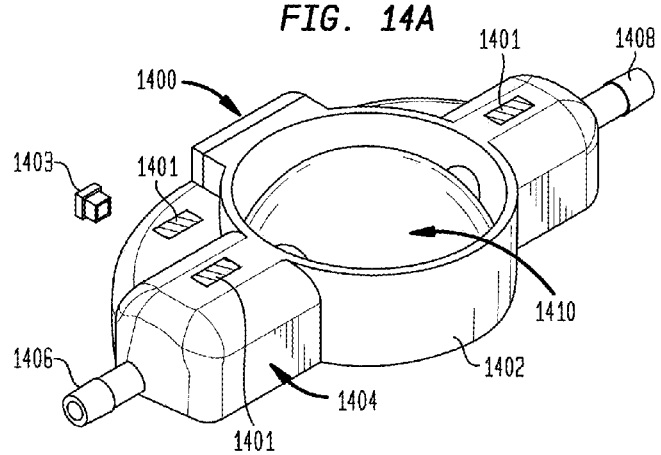
FIG. 14A is a perspective view of a compact flusher.
Figure 14B:
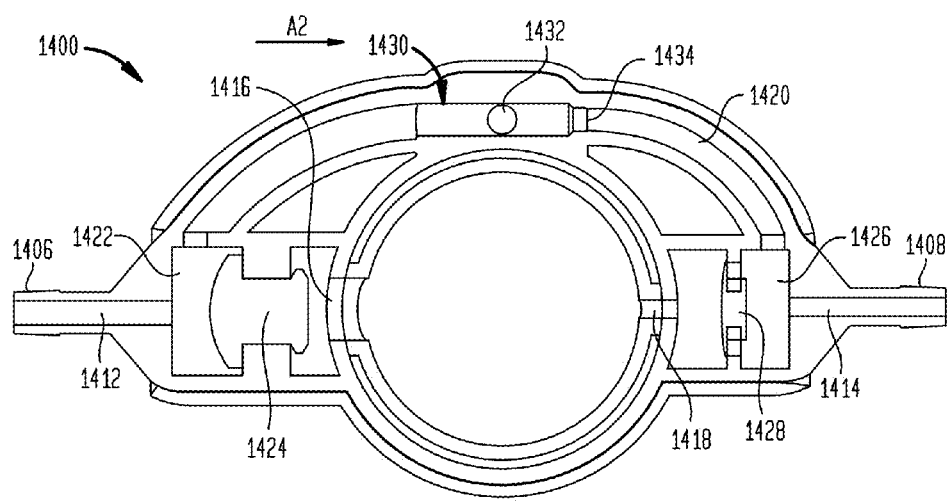
FIG. 14B is a sectional plan view of the flusher of FIG. 14A.
Figure 14C:
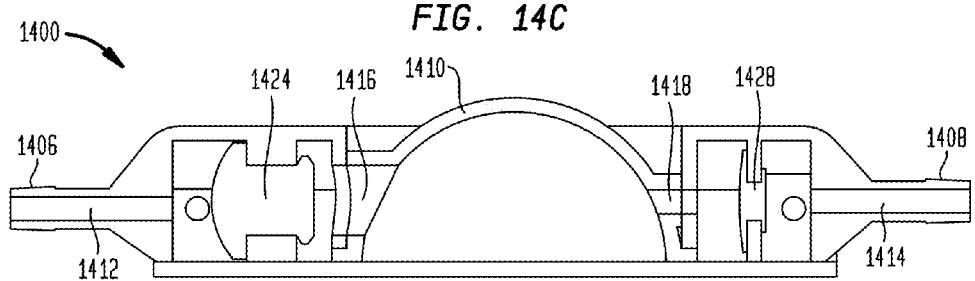
FIG. 14C is a sectional profile view of the flusher of FIG. 14A.
Figure 14D:
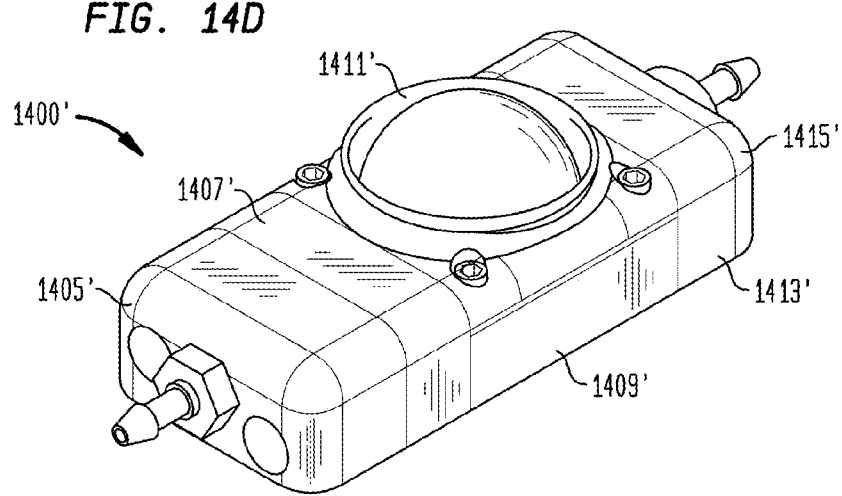
FIG. 14D is a perspective view of a modular flusher.
Figure 14E:
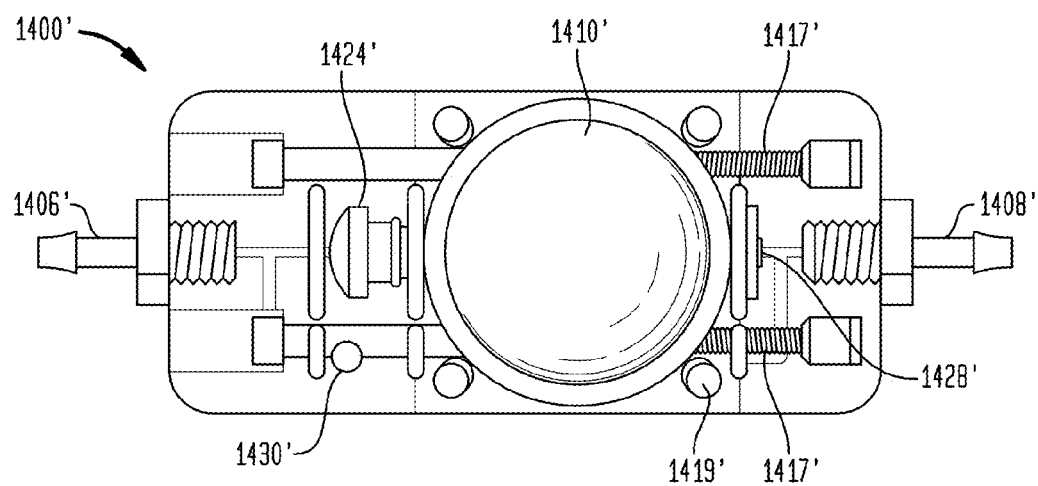
FIG. 14E is a plan view of the flusher of FIG. 14D with portions shown in phantom.
Figure 14F:
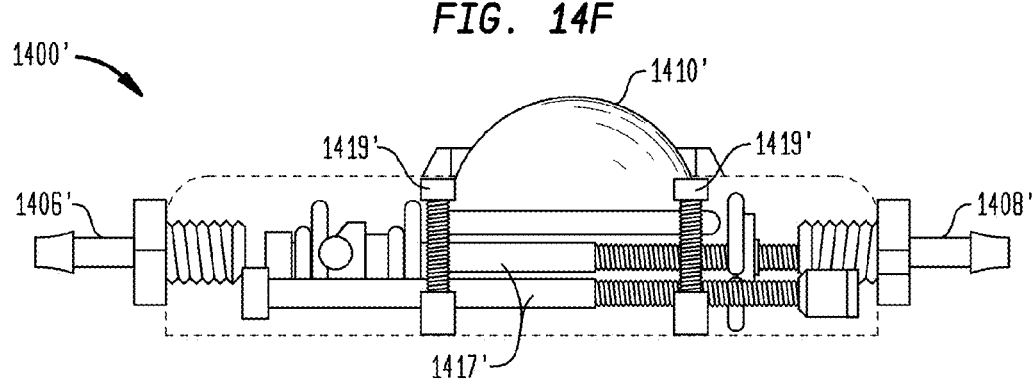
FIG. 14F is a profile view of the flusher of FIG. 14D with portions shown in phantom.
Figure 14G:
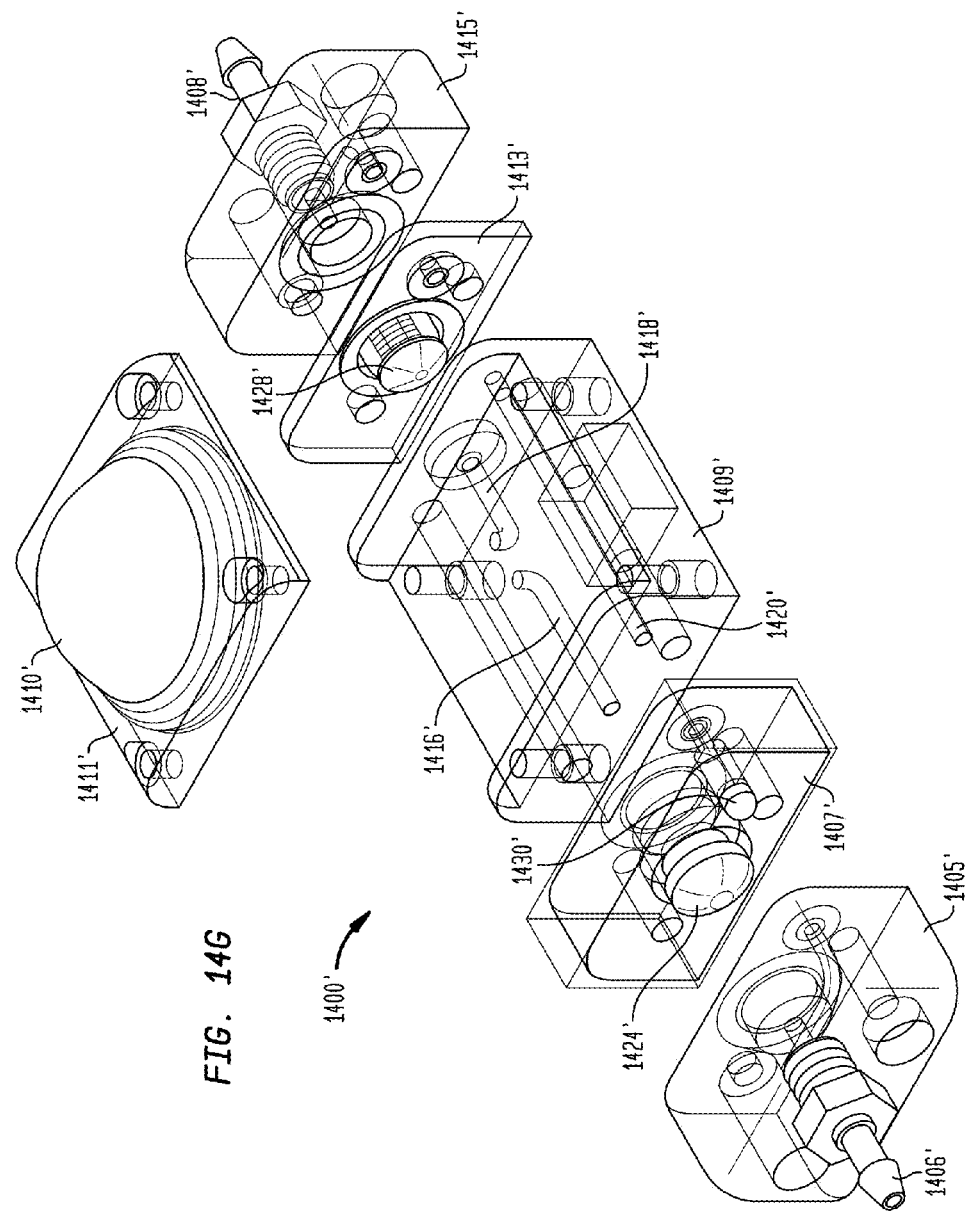
FIG. 14G is an exploded perspective view of the flusher of FIG. 14D with portions shown in phantom.

FIGS. 14A-14C illustrate another exemplary embodiment of a flusher 1400. The flusher 1400 includes a body 1404 with an upstream port 1406 configured to be coupled to or placed in fluid communication with a ventricular catheter and a downstream port 1408 configured to be coupled to or placed in fluid communication with a drain catheter. The flusher also includes a dome 1410 that can be actuated, e.g., by exerting downward finger pressure on the dome through a patient's skin, to expel fluid from the dome. The flusher body 1404 also includes a cylindrical sidewall 1402 that extends around the circumference of the dome base and has a height that is approximately equal to the maximum height of the dome 1410. The sidewall 1402 can protect the dome 1410 from inadvertent actuation (e.g., when a patient with the flusher 1400 implanted beneath their scalp lies down, pressing the flusher against a surface). A network of fluid channels is formed in the body 1404 of the flusher, and includes a ventricle channel 1412, a drain channel 1414, a flush channel 1416, a refill channel 1418, and a bypass channel 1420.

The ventricle channel 1412 extends from the upstream port 1406 to a flush valve chamber 1422 in which a flush valve 1424 configured to selectively place the flush channel 1416 in fluid communication with the ventricle channel is disposed. The drain channel 1414 extends from the downstream port 1408 to a refill valve chamber 1426 in which a refill valve 1428 configured to selectively place the drain channel in fluid communication with the refill channel 1418 is disposed. The bypass channel 1420 extends from the refill valve chamber 1426 to the flush valve chamber 1422 and includes an inline bypass valve 1430 configured to control fluid communication through the bypass channel. The refill channel 1418 and the flush channel 1416 are in fluid communication with the interior of the dome 1410.

The illustrated refill valve 1428 is an umbrella-type check valve, though other one-way valves can be used instead or in addition. The refill valve 1428 is configured to allow fluid flow from the drain channel 1414 into the refill channel 1418 and to prevent fluid flow from the refill channel into the drain channel.

The illustrated flush valve 1424 is an umbrella-type check valve, though other one-way valves can be used instead or in addition. The flush valve 1424 is configured to allow fluid flow from the flush channel 1416 into the ventricle channel 1412 and to prevent fluid flow from the ventricle channel into the flush channel. The flush valve 1424 is configured to open only when a predetermined differential pressure threshold is reached across the valve. For example, the flush valve 1424 can be configured such that the valve only opens when the pressure in the flush channel 1416 is at least 40 psig greater than the pressure in the ventricle channel 1412.

The illustrated bypass valve 1430 is a ball and socket valve, though other valve types can be used instead or in addition. The bypass valve 1430 is configured to automatically control fluid communication through the bypass channel 1420. When low pressure fluid flow in the direction of the arrow A2 exists in the bypass channel 1420 (e.g., when normal ventricular draining is taking place), the ball 1432 moves away from a seat 1434, and fluid is free to flow from the ventricle channel 1412 to the drain channel 1414, around the ball. When high pressure fluid flow in the direction of the arrow A2 exists in the bypass channel 1420 (e.g., when the pressure in the ventricle channel 1412 spikes as a flushing cough is emitted through the flush valve 1424), the ball 1432 moves into engagement with the seat 1434, sealing off the bypass channel 1420 and preventing fluid flow from the ventricle channel to the drain channel 1414. The bypass valve 1430 thus has a first position in which the ventricle channel 1412 is in fluid communication with the drain channel 1414 and a second position in which the ventricle channel is not in fluid communication with the drain channel. The bypass valve 1430 is configured to automatically move from the first position to the second position in response to a flushing cough emitted through the flush valve 1424.

The flusher 1400 can include one or more septa 1401 which can be used to prime the dome 1410 and/or the various fluid channels of the flusher with a fluid such as saline, or to inject drugs or therapeutic agents for delivery to the patient. In use, the septum 1401 can be pierced with a needle and fluid can be injected through the septum and into the flusher 1400, e.g., to clear any air bubbles from the interior of the flusher. Each septum 1401 can be formed from a self-sealing material such as silicone such that the septum reseals itself after the needle is withdrawn. The flusher 1400 can be primed before or after implantation in the patient. In some embodiments, the dome 1410 itself can act as a self-sealing septum which can be pierced with a needle to prime the flusher 1400. Each septum 1401 can be mounted sub-flush in a bore hole configured to receive a plug 1403 to provide a seal over the septum. The plug 1403 can be configured to couple to the flusher body (e.g., via a snap fit, interference fit, threaded fit, or the like) after the flusher 1400 is primed via the septum 1401. Septa can be included to provide fluid paths into any of the channels or chambers of the flusher 1400.

In use, the flusher 1400 generally has two operating modes. In a normal operating mode, the bypass valve 1430 is open and fluid is allowed to flow freely from the upstream port 1406 to the downstream port 1408. When the flusher 1400 is implanted in a patient as part of a shunt system, fluid is free to flow from the ventricle and through the flusher to a valve or drain catheter disposed downstream from the flusher. In the normal operating mode, the dome 1410 remains filled with fluid previously supplied to the dome through the refill channel 1418.

In a flush operating mode, a force is exerted on the dome 1410 to collapse the dome and displace fluid therefrom into the flush channel 1416. This causes the differential pressure across the flush valve 1424 to increase until the popping pressure of the valve is reached, at which point the valve opens and the pressurized fluid is suddenly released. The sudden release results in an upstream "cough" or flush of fluid back through the ventricle channel 1412, which can be effective to clear obstructions from a ventricle catheter or other upstream component of the shunt system, or to open auxiliary flow paths as described further below. The cough of fluid causes the bypass valve 1430 to close, preventing the cough from travelling to the downstream port 1408. The refill valve 1428 also remains closed when the dome 1410 is actuated, preventing fluid from escaping through the refill channel 1418. After the cough of fluid is released, the low-pressure drainage flow through the bypass channel 1420 resumes and the ball 1432 naturally floats away from the seat 1434. The ball 1432 can also be actively urged away from the seat 1434 by a spring or other biasing mechanism. The flush valve 1424 closes once the pressure subsides, and the refill valve 1428 opens to allow the dome 1410 to be refilled through the refill channel 1418.

In some embodiments, the refill valve 1428 orifice can be larger in cross-sectional area than the drain channel 1414, such that fluid preferentially flows through the refill valve to refill the dome 1410 before flowing through the drain channel to downstream components of the shunt system 100. The dome 1410 can have ribs or resilient material properties such that the dome is self-righting. As the dome 1410 returns to its un-collapsed configuration, it can provide a suction force to draw fluid into the dome, allowing the dome to be preferentially refilled.

The size of the refill channel 1418 can be selected to control the rate at which the dome 1410 is refilled. For example, the cross-sectional area of the refill channel 1418 can be made small to choke the flow of fluid into the dome 1410. In embodiments in which the dome 1410 has resilient properties, this can advantageously prevent the dome from quickly springing back to the non-collapsed configuration and generating a reflux action in which debris or obstructions cleared by a flushing operation are sucked back into the shunt system.

The flusher 1400 thus facilitates generation and application of a high pressure cough of fluid which flushes the ventricle side of the shunt system only. The bypass valve 1430 prevents the cough of fluid from travelling through the drain side of the shunt system.

The illustrated flusher 1400 is packaged in a compact form factor that is amenable to implantation beneath the scalp of a patient. In an exemplary embodiment, the flusher 1400 can be about 1.0 inches long, about 0.25 inches wide, and about 0.25 inches tall.

FIGS. 14D-14G illustrate a flusher 1400' having a plurality of modular components which can be coupled to one another, for example using bolts or screws. The modular nature of the flusher 1400' can advantageously allow for easy customization of the device, for example by combining different valve modules with different dome modules and/or different channel modules. The valve modules can be selected from a group of valve modules having different valve sizes, shapes, opening pressures, etc. The dome module can be selected from a group of dome modules having different volumes, material properties, etc. The channel module can be selected from a group of channel modules having different diameters, relative lengths, etc.

In the illustrated embodiment, the flusher 1400' includes an upstream port module 1405', a flush valve module 1407', a channel module 1409', a dome module 1411', a refill valve module 1413', and a downstream port module 1415'. Except as indicated and as will be apparent to one of ordinary skill, the structure and function of the flusher 1400' is substantially identical to that of the flusher 1400. The upstream port module 1405' includes the upstream port 1406'. The flush valve module 1407' includes the flush valve 1424' and the bypass valve 1430'. The channel module 1409' includes the flush channel 1416', the refill channel 1418', and a portion of the bypass channel 1420'. The dome module 1411' includes the dome 1410'. The refill valve module 1413' includes the refill valve 1428'. The downstream port module 1415' includes the downstream port 1408'. First and second coupling screws or bolts 1417' extend longitudinally through the various modules of the flusher, coupling the modules to one another. The dome module 1411' is coupled to the channel module 1409' by a plurality of screws or bolts 1419'.

Figure 15A:
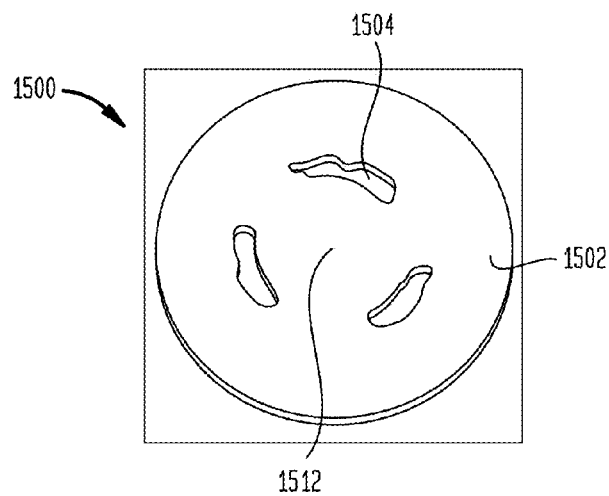
FIG. 15A is a plan view of a diaphragm valve disc.
Figure 15B:
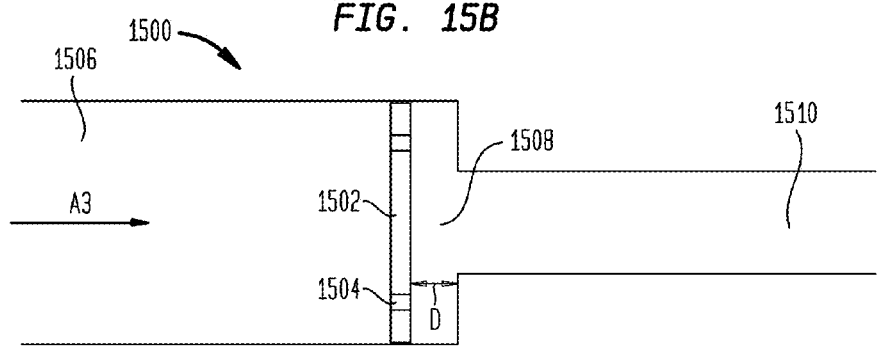
FIG. 15B is a sectional view of a diaphragm valve in an open position.
Figure 15C:
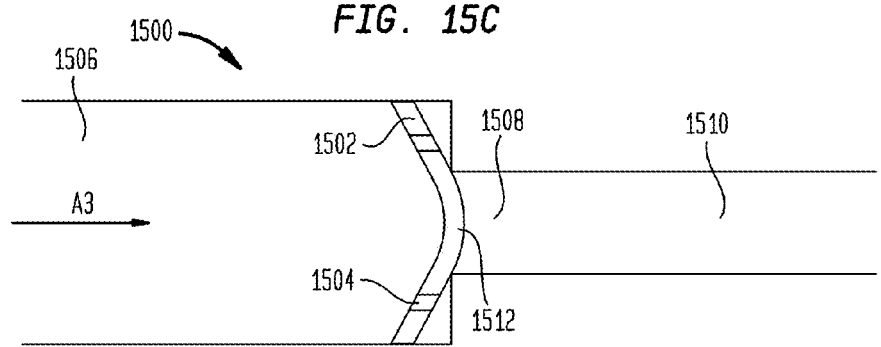
FIG. 15C is a sectional view of a diaphragm valve in a closed position.

The valves 1202, 1346, and 1430 disclosed above can be used interchangeably in any of the flushers 1200, 1300, 1400, 1400'. In addition, other valve types can be used, such as the diaphragm valve 1500 shown in FIGS. 15A-15C. For example, the diaphragm valve 1500 can be used in place of the bypass valve 1430 of the flusher 1400 and/or in place of the flapper valve 1346 of the flush system 1300. The diaphragm valve 1500 includes a flat elastomeric disc 1502 with one or more openings 1504 formed therethrough. The disc 1502 is positioned in a first fluid lumen 1506 adjacent to a port 1508 of a second lumen 1510 that is to be opened and closed by the diaphragm valve 1500, e.g., with a small separation distance D between the disc 1502 and the mouth of the port 1508. In operation, when low pressure flow in the direction of the arrow A3 exists in the fluid lumen 1506, the disc 1502 remains in a planar configuration as shown in FIG. 15B and fluid flows through the openings 1504 of the disc, such that the first lumen 1506 is in fluid communication with the second lumen 1510. When the differential pressure across the disc 1502 increases (e.g., when a flushing cough is emitted in the first lumen 1506), the disc deforms to a convex configuration as shown in FIG. 15C and a center portion 1512 of the disc presses against the port 1508 to seal off the port. The openings 1504 in the disc 1502 are formed in the periphery of the disc, outside of the center portion 1512, such that fluid communication between the first lumen 1506 and the second lumen 1510 is cut off when the disc is deformed into the convex configuration. When the pressure differential subsides, resilient properties of the disc 1502 cause it to regain its planar configuration, restoring fluid communication between the first lumen 1506 and the second lumen 1510.

Figure 15D:
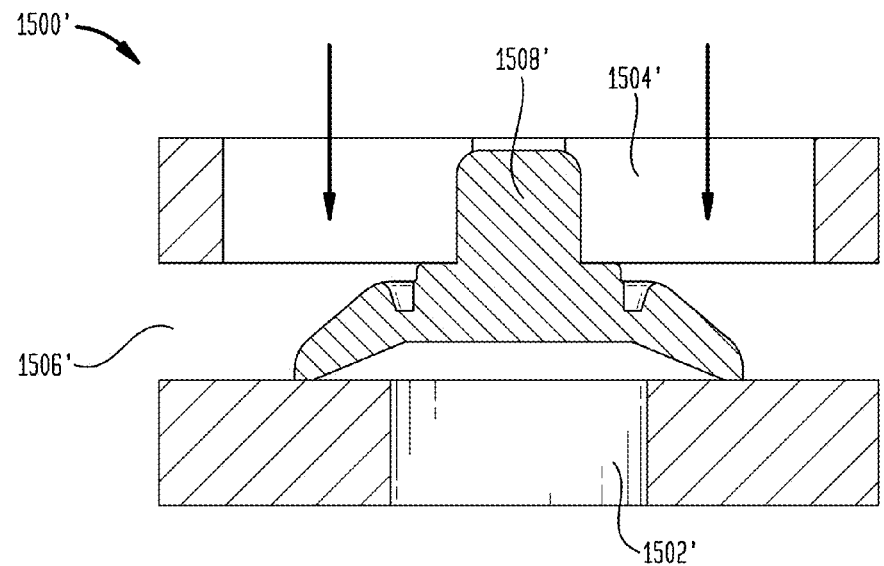
FIG. 15D is a sectional view of another exemplary valve in a closed position.
Figure 15E:
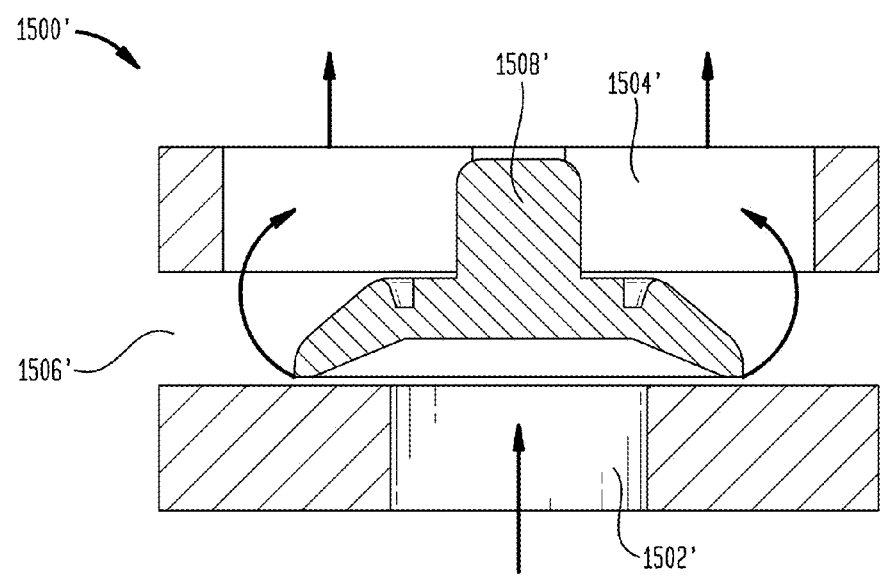
FIG. 15E is a sectional view of the valve of FIG. 15D in an open position.

Other valves which can be used with the flushers 1200, 1300, 1400, 1400' include Belleville type valves 1500' of the type shown in FIGS. 15D-15E, available from MINI-VALVE, INC. of Cleveland, Ohio. Specifically, the valve 1500' can be positioned such that the dome of the flusher is in fluid communication with the valve inlet 1502'. When a flush operation is performed, pressure generated in the dome lifts the valve body 1508' off of its seat, forming a fluid path between the valve inlet 1502' and the valve outlet 1504' as shown by the arrows in FIG. 15E. In the open position, a flush of fluid can flow from the dome, through the valve 1500', and out of the ventricle catheter. The sides 1506' of the valve chamber can be open to form part of the valve outlet 1504', or can be closed such that the valve outlet 1504' is only at the top of the valve chamber.

In some embodiments, the flushers disclosed herein can be configured to generate a flushing cough of fluid at a pressure of between about 20 psig to about 40 psig or more. In some embodiments, the volume of the flush can be between about 0 mL and about 1 mL or more. It will be appreciated that the flushers 1200, 1300, 1400, 1400' disclosed above are merely exemplary, and that any of a variety of flushers can be used with a shunt system in accordance with the teachings herein. A variety of exemplary flusher embodiments are disclosed in the description that follows. Except as indicated below or as will be readily appreciated by one having ordinary skill in the art given the context, the structure and operation of these various embodiments is similar or identical to that of the embodiments described above. Accordingly, a detailed description of such structure and operation is omitted here for the sake of brevity.

FIG. 16 illustrates another exemplary embodiment of a flusher 1600. The dome 1602 of the flusher includes a stem 1604 that extends from an interior ceiling of the dome and that pinches off or occludes the bypass channel 1606 when the dome is actuated, cutting off fluid flow therethrough and eliminating the need for a dedicated bypass valve in the bypass channel. The flusher 1600 includes an umbrella valve 1608 configured to crack open to release a flush of fluid in the upstream direction when the differential pressure across the valve exceeds a threshold amount. The refill channel 1610 for the flusher dome can be disposed directly beneath the stem 1604 such that it too is blocked when the dome 1602 is depressed.

FIG. 17 illustrates another exemplary embodiment of a flusher 1700. The flusher 1700 includes a flapper valve 1702 having a stem 1704 and a bulb portion 1706. The flapper valve 1702 is configured to pivot in the direction of the arrow A4 about a hinge axis 1708 (e.g., a pivot pin to which the stem 1704 is coupled or a living hinge formed in the stem) when the flusher dome 1710 is depressed to perform a flushing operation. The flapper valve 1702 pivots until the bulb 1706 contacts a ramp or wedge portion 1712 of the flusher body 1714, sealing off the drain side 1716 of the shunt system until the flushing operation is completed. The flapper valve 1702 can be biased towards the open configuration in which the drain port 1716 is in fluid communication with the ventricle port 1718. A small refill orifice 1720 is provided to refill the dome 1710 when flow through the flusher resumes, and can be sized to restrict the rate at which the dome returns to its un-collapsed configuration.

Figure 18:
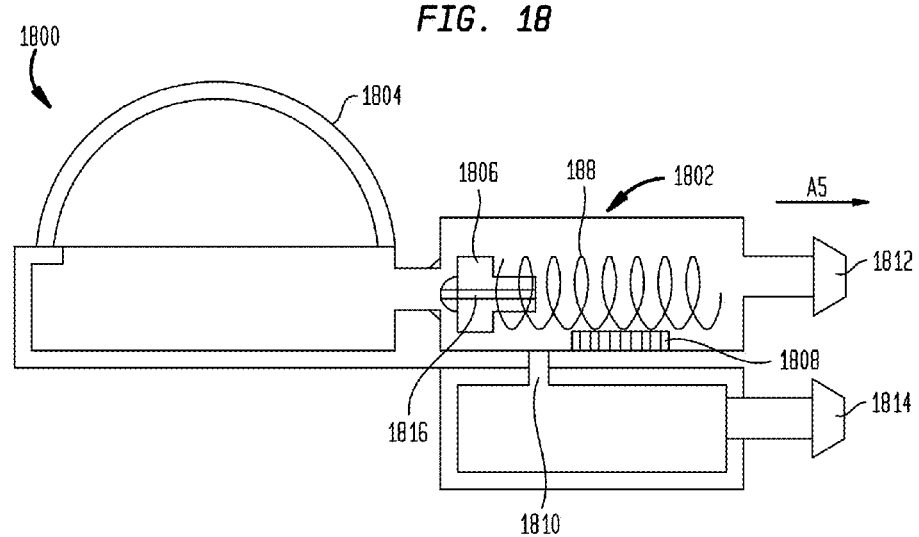
FIG. 18 is a sectional view of a flusher with a piston and spring valve.

FIG. 18 illustrates another exemplary embodiment of a flusher 1800. The flusher 1800 includes a piston and spring valve 1802 configured to move in the direction of the arrow A5 when the flush dome 1804 is depressed. The piston 1806 moves until it hits a stop 1808, which maintains the piston in a position that occludes a passageway 1810 between the ventricle port 1812 and the drain port 1814. Accordingly, the flush released through the piston and spring valve 1802 flows only to the ventricle port and not to the drain port. A small refill lumen 1816 is formed through the center of the piston 1806 such that, when the flushing operation is completed and the piston returns under the bias of the spring 1818 to its original position, fluid can flow through the refill lumen to refill the dome 1804.

Figure 19A:
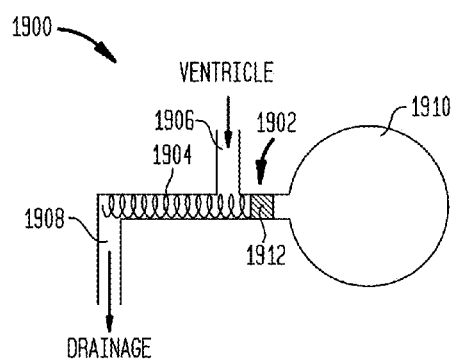
FIG. 19A is a sectional view of a flusher with a piston and spring valve, shown with the valve in a first position.
Figure 19B:
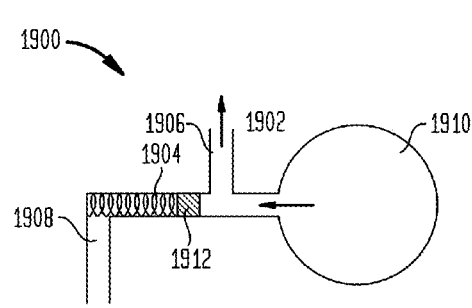
FIG. 19B is a sectional view of the flusher of FIG. 19A, shown with the valve in a second position.

FIGS. 19A-19B illustrate another exemplary embodiment of a flusher 1900. The flusher 1900 includes a piston and spring valve 1902 disposed in a flush lumen 1904 that extends between a ventricle lumen 1906, a drain lumen 1908, and a dome 1910. The piston 1912 is biased to a first position, shown in FIG. 19A, in which it is not disposed between the ventricle and drain lumens 1906, 1908 and in which fluid is free to flow from the ventricle lumen to the drain lumen. The piston 1912 also has a second position, shown in FIG. 19B, to which the piston is moved when the dome 1910 is actuated. In the second position, the piston 1912 is disposed between the ventricle and drain lumens 1906, 1908 and thereby cuts off fluid communication between the ventricle and drain lumens such that the flushing cough only flows to the ventricle lumen. The piston 1912 can include a refill lumen as described above with respect to the flusher 1800 of FIG. 18.

FIGS. 20A-20B illustrate another exemplary embodiment of a flusher 2000. The flusher 2000 includes a flapper valve 2002 actuated by a mechanical lever/linkage system 2004 to block the drain side of the system when a flushing operation is performed. The lever 2004 has a first arm 2006 disposed under the flush dome 2008 which pivots in a clockwise direction when the flush dome is depressed into contact with the first arm. This pivoting movement of the first arm 2006 causes longitudinal translation of a center link 2010 of the linkage, which in turn causes pivoting movement of a flapper 2012. As shown in FIG. 20A, during normal operation, the flapper 2012 seals the flush lumen 2014 and fluid is free to flow from the ventricle port 2016 to the drain port 2018. As shown in FIG. 20B, when a flushing operation is performed, the lever 2004 is actuated to move the flapper 2012 such that the drain port 2018 is sealed and a flush generated in the dome 2008 flows only through the ventricle port 2016. When the flush is completed, the lever 2004 returns to its original position, either naturally or under the bias of a spring or other biasing mechanism. A small refill port (not shown) can be formed in or around the flapper 2012 to allow the dome 2008 to be refilled after a flushing operation is completed and/or to limit the rate at which the dome is refilled.

FIGS. 21A-21B illustrate another exemplary embodiment of a flusher 2100. The flusher 2100 includes a flush valve 2102 formed by a pair of elastomeric lips 2104. While two lips 2104 are shown, it will be appreciated that any number of lips can be provided. Each lip is attached at one end to the sidewall of the flush lumen 2106. The other end of the lip is free to move towards or away from the dome 2108 in response to fluid pressure exerted thereon. As shown in FIG. 21A, during normal operation, the lips 2104 are directed inwardly towards the flushing dome 2108 and fluid is free to flow from the ventricle port 2110 to the drain port 2112. As shown in FIG. 21B, when a flushing operation is performed, the lips 2104 are urged outwardly away from the dome 2108 under the force of the flushing cough of fluid. The lips 2104 are sized and configured such that, when disposed as shown in FIG. 21B, the drain port 2112 is sealed by one of the lips while the ventricle port 2110 is placed in fluid communication with the dome 2108, such that a flush generated in the dome flows only through the ventricle port. A recess 2114 can be formed in the ventricle port 2110 to allow fluid to flow around the upstream lip when the lips are positioned as shown in FIG. 21B. When the flush is completed, the lips 2104 return to their original position, either naturally or under the bias of a spring or other biasing mechanism. A small refill port (not shown) can be formed in the lips 2104 to allow the dome 2108 to be refilled after a flushing operation is completed and/or to limit the rate at which the dome is refilled.

Figure 22:
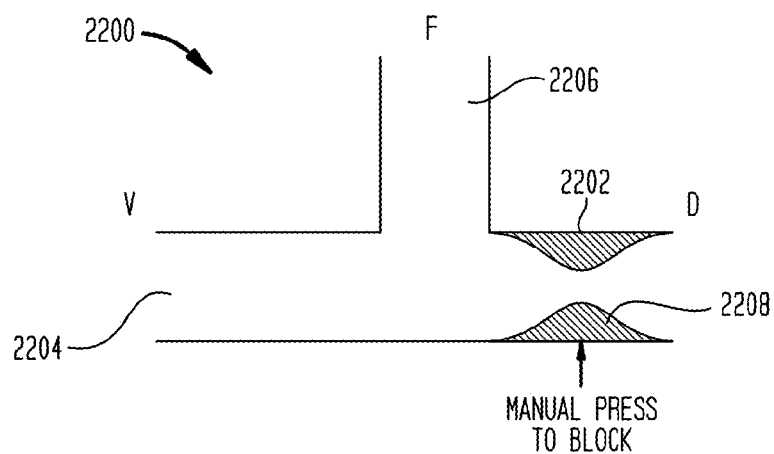
FIG. 22 is a sectional view of a flusher with a drain channel that can be manually occluded.

FIG. 22 illustrates another exemplary embodiment of a flusher 2200. The flusher 2200 includes a flexible or compliant drain lumen 2202 which can be compressed by an external force (e.g., finger pressure applied to the flusher through the patient's skin) to occlude the drain port. In use, the drain lumen 2202 is compressed to occlude the drain port while a flushing operation is performed, such that the flush is directed only through the ventricle port 2204. In other words, the drain lumen 2202 can be compressed to cut off fluid communication between the drain lumen and the ventricle port 2204 and between the drain lumen and the flushing lumen 2206. In some embodiments, the drain lumen 2202 can include internal protrusions or a section having a reduced cross-sectional area 2208 to more-reliably occlude the drain lumen when external pressure is applied thereto. The drain lumen 2202 can also include external features to facilitate location of the drain lumen through the skin. For example, a push-button, protrusion, dome, or other external feature can be provided to provide tactile feedback to a user.

Figure 23:
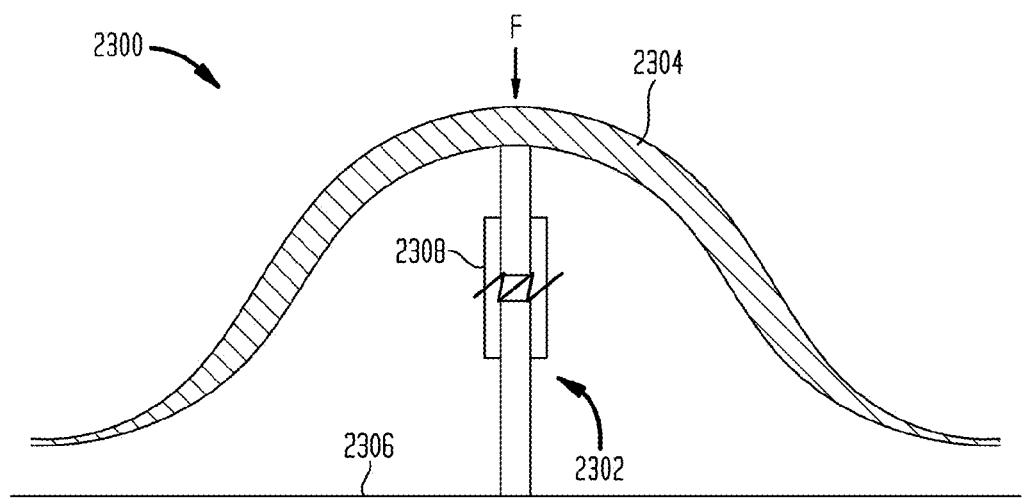
FIG. 23 is a sectional view of a flusher with a collapsible stem.

FIG. 23 illustrates another exemplary embodiment of a flusher 2300. The flusher 2300 includes a collapsible stem 2302 that extends from the interior ceiling of the dome 2304 to the base 2306 of the flusher body. The illustrated stem includes upper and lower portions that engage one another with opposed saw tooth bearing surfaces 2308. The surfaces 2308 are configured such that a predetermined threshold force applied to the stem 2302 in the longitudinal direction is required to deflect the teeth enough for the stem to collapse and allow the dome 2304 to be compressed. Accordingly, the dome 2304 can only be depressed when a predetermined threshold force is applied, which can prevent inadvertent flushing or compression of the dome. The stem 2302 can also be configured to emit or provide tactile feedback, e.g., in the form of a click or snap, to provide confirmation to the user that sufficient force was applied to initiate a flushing operation.

Figure 24:
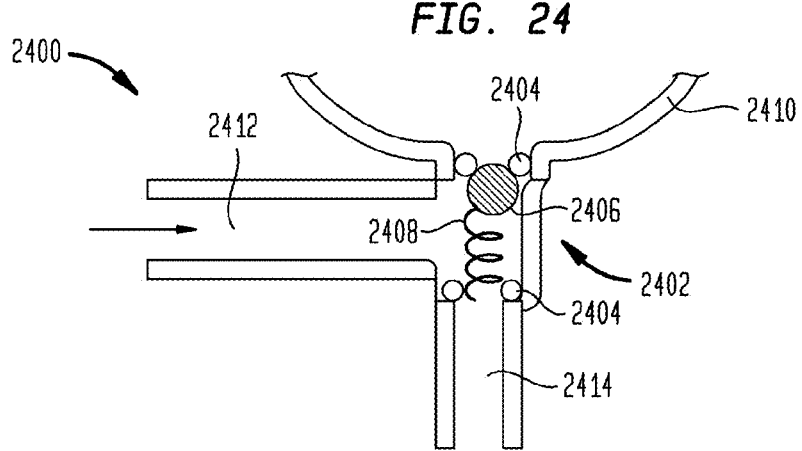
FIG. 24 is a sectional view of a flusher with a ball and spring valve.
Figure 26A:
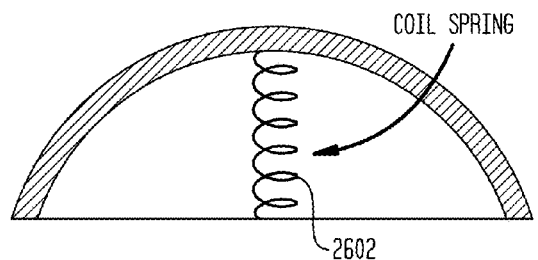
FIG. 26A is a sectional view of a flusher with a coil spring disposed within the flush dome.
Figure 26B:
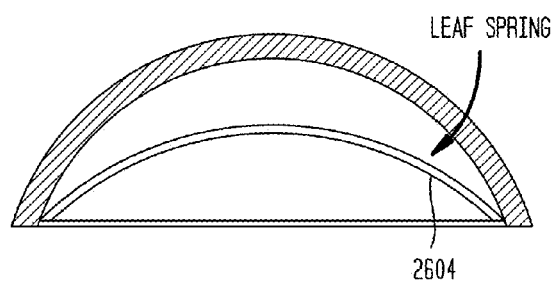
FIG. 26B is a sectional view of a flusher with a leaf spring disposed within the flush dome.

FIG. 24 illustrates another exemplary embodiment of a flusher 2400. The flusher 2400 includes a ball and spring valve 2402 with first and second O-rings 2404 that act as valve seats for the ball and spring valve. The ball 2406 is biased by the spring 2408 to a first position, shown in FIG. 24A, in which the ball is seated against the upper O-ring to cut off fluid communication between the dome 2410 and the ventricle and drain ports 2412, 2414. In this position, fluid is free to flow from the ventricle port 2412 to the drain port 2414. When a flushing operation is performed, the ball 2406 moves to a second position in which the ball is seated against the lower O-ring to cut off fluid communication between the drain port 2414 and the dome 2410 and between the drain port and the ventricle port 2412. Accordingly, the flushing cough only flows to the ventricle port 2412. The dimensions of the ball 2406 and the strength of the spring 2408 can be selected to control the opening pressure of the ball and spring valve, e.g., to ensure the valve only opens when a high-pressure cough is generated in the dome 2410. A refill lumen (not shown) can be formed between the ventricle port 2412 and the dome 2410 (e.g., through the ball) to allow the dome to be refilled after a flushing operation is performed.

FIGS. 25A and 25B illustrate another exemplary embodiment of a flusher 2500. The flusher 2500 includes an L-shaped piston valve 2502 having first and second legs 2504, 2506. During normal operation, the piston 2502 is biased by a spring 2508 to the position shown in FIG. 25A, such that a fluid lumen 2510 formed through the first leg 2504 of the piston 2502 provides fluid communication between the ventricle port 2512 and the drain port 2514 and such that the body of the piston blocks fluid communication between the dome 2516 and the ventricle and drain ports. When a flushing operation is performed, the force of the flush urges the piston 2502 down against the force of the bias spring 2508, such that both ends of the fluid lumen 2510 are occluded. In addition, a second leg 2506 of the piston 2502 is positioned such that it occludes the drain port 2514. The piston 2502 is displaced such that the ventricle port 2512 is not occluded, and therefore the ventricle port is placed in fluid communication with the flush dome 2516 as shown in FIG. 25B such that the flushing cough flows only through the ventricle port.

In any of the embodiments disclosed herein, the dome can include one or more features for biasing the dome towards a collapsed configuration or towards an un-collapsed configuration. For example, a coil spring 2602 (shown in FIG. 26A) or a leaf spring 2604 (shown in FIG. 26B) can be disposed within the dome and can extend from an interior ceiling of the dome to a base of the flusher body. In some embodiments, the spring can be biased to urge the dome towards a collapsed configuration, such that the spring controls the rate at which the dome expands when refill fluid is supplied thereto. In other embodiments, the spring can be biased to urge the dome towards an un-collapsed position, such that the spring helps return the dome to a starting position after a flushing operation is performed.

Figure 27:
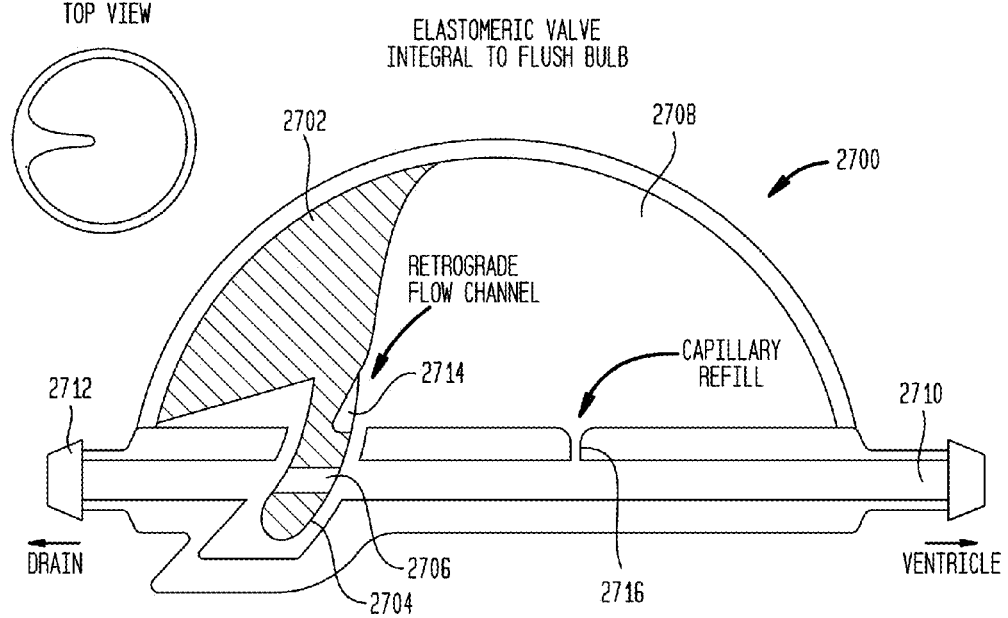
FIG. 27 is a sectional view of a flusher with a stem valve, the stem valve having a primary flow channel and a retrograde flush flow channel.

FIG. 27 illustrates another exemplary embodiment of a flusher 2700. The flusher 2700 includes a stem 2702 that extends from an interior ceiling of the dome and includes a tongue 2704 with a fluid lumen 2706 formed therethrough. During normal operation, the dome 2708 is in an un-collapsed configuration and the tongue 2704 is positioned as shown in FIG. 27 such that the fluid lumen 2706 formed therein provides fluid communication between the ventricle port 2710 and the drain port 2712. In this position, the tongue 2704 blocks fluid communication between the dome 2708 and the ventricle and drain ports 2710, 2712. When a flushing operation is performed, the dome 2708 is depressed or collapsed and the tongue 2704 is shifted down, such that the fluid lumen 2706 extending through the tongue is moved out of alignment with the ventricle and drain ports 2710, 2712 and the tongue occludes the drain port. A cut-out or flow channel 2714 is formed in the tongue 2704 such that when the tongue is shifted down to block the drain port 2712, the ventricle port 2710 is placed in fluid communication with the dome 2708 and the flushing cough flows only through the ventricle port. When the flushing operation is completed, a portion of the fluid flowing from the ventricle port 2710 to the drain port 2712 refills the dome 2708 through a refill capillary 2716, which can be sized to limit the rate at which the dome returns to its un-collapsed configuration.

FIGS. 49A-49G illustrate an exemplary embodiment of a flusher 4900. The flusher 4900 generally includes an outer shell or body 4902 that defines a flush dome 4904. The bottom surface of the body 4902 can be closed by a base plate 4906 to which the body is sealed. A flush valve assembly 4908 and a refill valve assembly 4910 can be disposed within the body 4902, and a pinch tube 4912 can extend over the top of the flush dome 4904.

The flush valve assembly 4908 includes a valve cartridge 4914, a valve body 4916, and an adjustment disc 4918. The valve cartridge 4914 includes an upstream port 4920 configured to be coupled to or placed in fluid communication with a ventricular catheter, a flush port 4922 configured to be placed in fluid communication with the flush dome 4904, and a passive flow port 4924 configured to be placed in fluid communication with a passive flow lumen 4926 defined by the body 4902. Each of the ports 4922, 4924, 4926 are in fluid communication with an interior chamber defined 4928 by the valve cartridge 4914. The upstream port 4920 and/or the flush port 4922 can be defined by male barbed fittings that extend radially outward from the valve cartridge 4914. The barbed fittings can advantageously facilitate coupling of the flush valve assembly 4908 with the body 4902 (in the case of the flush port 4922) or with a ventricular catheter or other shunt system component (in the case of the upstream port 4920). The passive flow port 4926 can be defined by an opening formed in a sidewall of the valve cartridge 4914. The valve cartridge 4914 and the barbed fittings can be formed as monolithic, one-piece component which can advantageously provide a high strength unit capable of withstanding high operating pressures and lateral stress on the upstream port fitting 4920. High interference barbed fittings can be used to allow high pressure operation without leakage, which allows the flushing pressure to be delivered only to the flush valve and facilitates more precise and repeatable opening pressure thresholds. In some embodiments, the barbed fittings can be configured to withstand up to 120 psi.

The valve body 4916 can be an umbrella-type valve, a Belleville-type valve, or the like. The valve body 4916 is sandwiched between the upper wall of the chamber 4928 and the adjustment disc 4918 in an interference fit such that the valve body is compressed. The valve body 4916 defines a substantially concave upper surface that forms a fluid-tight seal with the upper wall of the chamber 4928 to seal off the flush port 4922 from the upstream port 4920 and the passive flow port 4924 during normal operation. When sufficient pressure is applied to the upper surface of the valve body 4916, the valve body deforms away from the upper wall of the chamber 4928 to allow fluid communication between the flush port 4922 and the upstream port 4920 and between the flush port and the passive flow port 4924. The threshold pressure at which the valve body 4916 opens can be infinitely adjusted by adjusting the pressure exerted on the valve body by the adjustment disc 4918. In the illustrated embodiment, the adjustment disc 4918 is threadably mounted in the cartridge 4914 such that rotating the disc in a first direction increases the compression of the valve body 4916 to increase the threshold pressure, and such that rotating the disc in a second, opposite direction decreases the compression of the valve body to decrease the threshold pressure. It will be appreciated that other means of adjusting the compression of the valve body 4916 can be used instead or in addition. A driving interface 4930 can be formed in the bottom surface of the adjustment disc 4918 to facilitate rotation of the disc by a driving tool. In the illustrated embodiment, the driving interface 4930 comprises first and second opposed cylindrical recesses configured to receive corresponding first and second pins of a driving tool. The arrangement of the recesses can allow rotation of the disc 4918 to be easily visualized and to be performed in a repeatable and controlled manner. The adjustment disc 4918 can be adjusted in-process and locked in a desired position using an adhesive (e.g., medical grade cyanoacrylate or the like). Locking the disc 4918 in place, e.g., by freezing the threads using an adhesive, can advantageously allow for the threshold pressure of the valve to be securely maintained at the desired level.

When the valve body 4916 is sealed against the upper wall of the chamber 4928, fluid can flow from the upstream port 4920, into the chamber, around the outside of the closed valve body, and into the passive flow port 4924.

The flush valve assembly 4908 can be positioned within a cavity 4932 defined in the body 4902 of the flusher 4900 such that the upstream port 4920 protrudes through a sidewall of the body and such that the flush port 4922 extends into a passage 4934 that connects the cavity to the flush dome 4904. When the flush valve assembly 4908 is disposed in the body 4902, the passive flow port 4924 is aligned with the passive flow channel 4926 defined in the body.

The refill valve assembly 4910 includes a refill valve 4936 and a refill plate 4938. The refill plate 4938 is mounted in the body 4902 beneath the flush dome 4904. A passive flow channel 4940 extends through the refill plate 4938 and is in fluid communication with the passive flow channel 4926 of the body 4902 at one end and the pinch tube 4912 at the other end. The refill valve 4936 is operable to selectively place the passive flow channel 4940 in fluid communication with the interior of the flush dome 4904, for example to refill the flush dome after a flushing operation is performed. In the illustrated embodiment, the refill valve 4936 is an umbrella valve that includes a valve stem and a valve head. The stem is mounted within a valve guide formed in the refill plate 4938. A plurality of openings 4942 are formed in the plate 4938 around the circumference of the valve guide. When the refill valve 4936 is closed, the valve head covers the plurality of openings 4942 and prevents fluid communication between the passive flow channel 4940 and the flush dome 4904. When the refill valve 4936 is opened, the valve head is lifted off of the openings 4942 such that fluid can flow between the passive flow channel 4940 and the flush dome 4904.

Figure 49A:
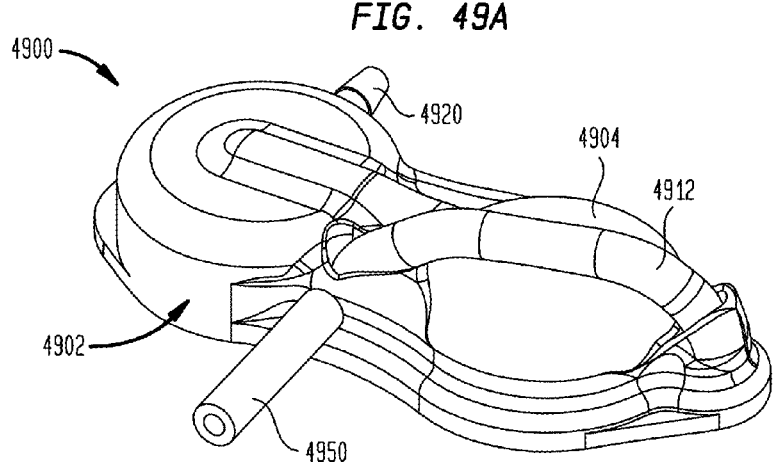
FIG. 49A is a perspective view of a flusher.
Figure 49B:
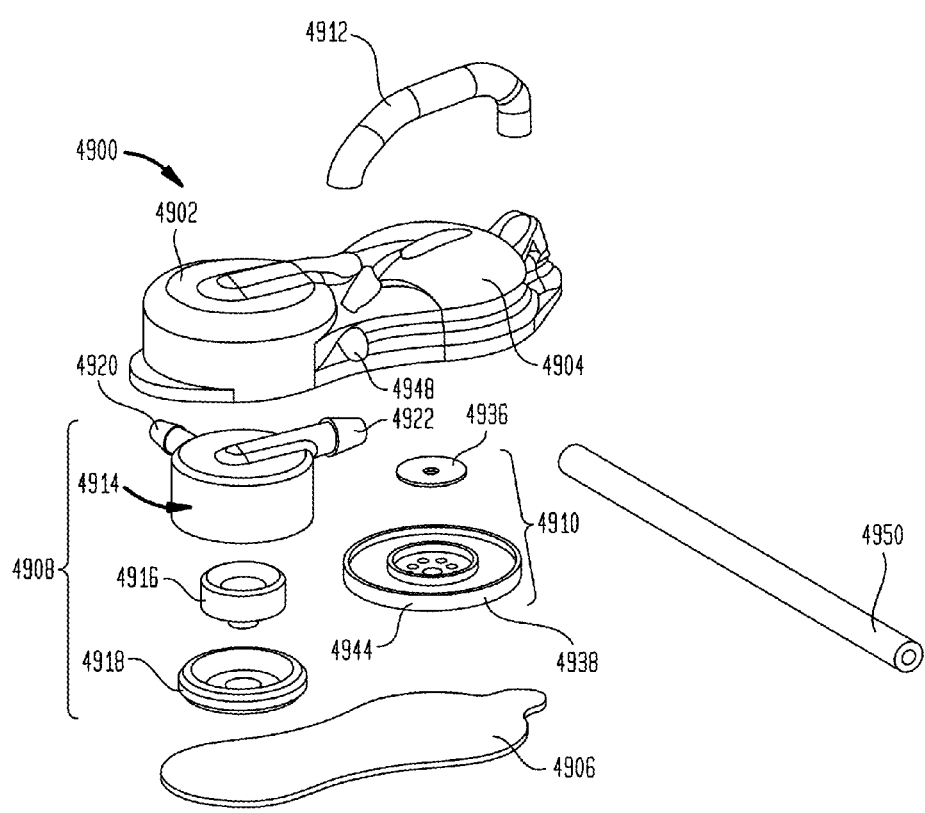
FIG. 49B is an exploded perspective view of the flusher of FIG. 49A.
Figure 49C:
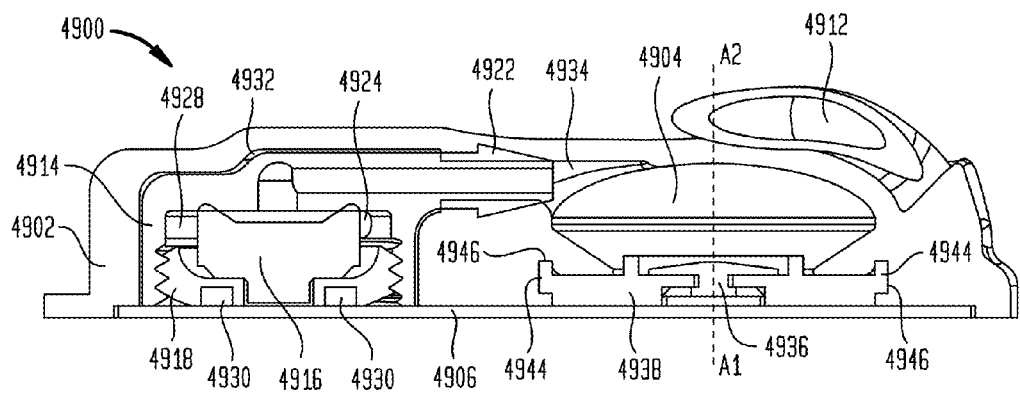
FIG. 49C is a longitudinal sectional view of the flusher of FIG. 49A.
Figure 49D:
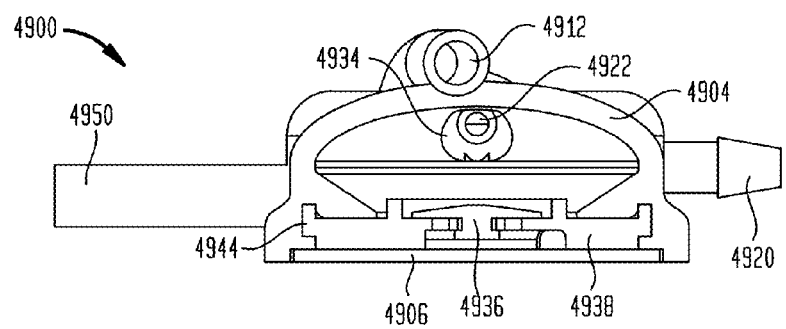
FIG. 49D is a lateral sectional view of the flusher of FIG. 49A.
Figure 49E:
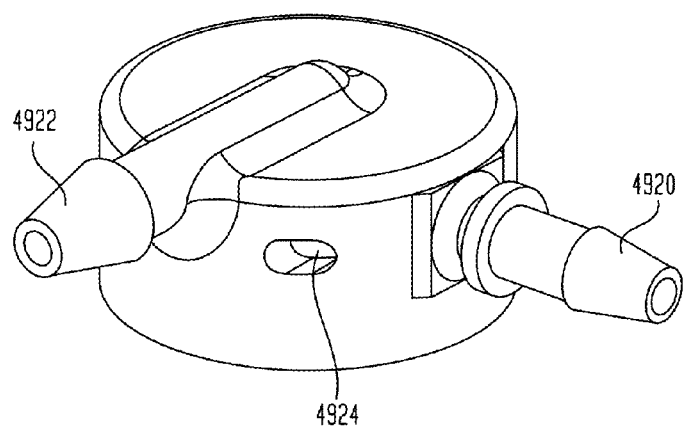
FIG. 49E is a perspective view of a valve cartridge of the flusher of FIG. 49A.

As perhaps best shown in FIG. 49C, the refill valve 4936 is disposed beneath the flush dome 4904 and oriented such that the axis A1 along which the valve opens and closes is substantially parallel to the axis A2 along which the flush dome is actuated. In other words, when an actuation force is applied to the flush dome 4904 during a flushing operation, the primary component of the actuation force acts in the same direction as the valve closing direction. Also, the stacked nature of the refill valve 4936 and flush dome 4904 allows pressure in the flush dome to act directly on the refill valve, helping ensure that the refill valve is closed when the flush dome is actuated. The stacked arrangement also reduces the overall length and profile of the flusher 4900.

The refill plate 4938 can be rigid, semi-rigid, or flexible. The refill plate 4938 can mechanically interlock with the body 4902 to provide a robust connection capable of withstanding high operating pressures. As shown, the refill plate 4938 can be disc-shaped and can include a sidewall that extends about a circumference of the plate and protrudes radially-outward and axially upward to define a lip 4944 that is received within a corresponding annular recess or undercut 4946 formed in the body 4902. The body 4902 can be formed from a flexible material to allow the body to be stretched over the lip 4944 of the refill plate 4938 during assembly. In some embodiments, the body 4902 is molded from silicone and bonded to the refill plate 4938 using silicone RTV or other adhesive. The base plate 4906 can likewise be bonded to the body 4902 and/or to the refill plate 4938 using silicone RTV or the like. The base plate 4906 can be formed from silicone and can include a polyester reinforcing mesh.

The pinch tube 4912 can be configured to provide a valve-less means of closing off the drain side of the shunt system during a flush operation. The pinch tube 4912 extends out of the body 4902, across the top of the flush dome 4904, and into a coupling where it is placed in fluid communication with a downstream port 4948 configured to be coupled to or placed in fluid communication with a drain catheter, shunt valve, or other downstream device (e.g., via a drain tube 4950 as shown). The pinch tube 4912 can be positioned such that it will naturally be compressed by a user when the user actuates the flush dome 4904. The flusher 4900 thus allows a single user motion, applied at a single contiguous contact area, to both seal off the drain side of the system and actuate the flush dome. In some embodiments, the pinch tube 4912 can be more easily deformable than the flush dome 4904 to increase the likelihood that the pinch tube is closed off when a flushing operation is performed. For example, the pinch tube 4912 can be formed from a material having a lower durometer than the material used to form the flush dome 4904. In an exemplary embodiment, the pinch tube 4912 is formed from 30 durometer silicone while the flush dome 4904 is formed from 70 durometer silicone.

Figure 49F:
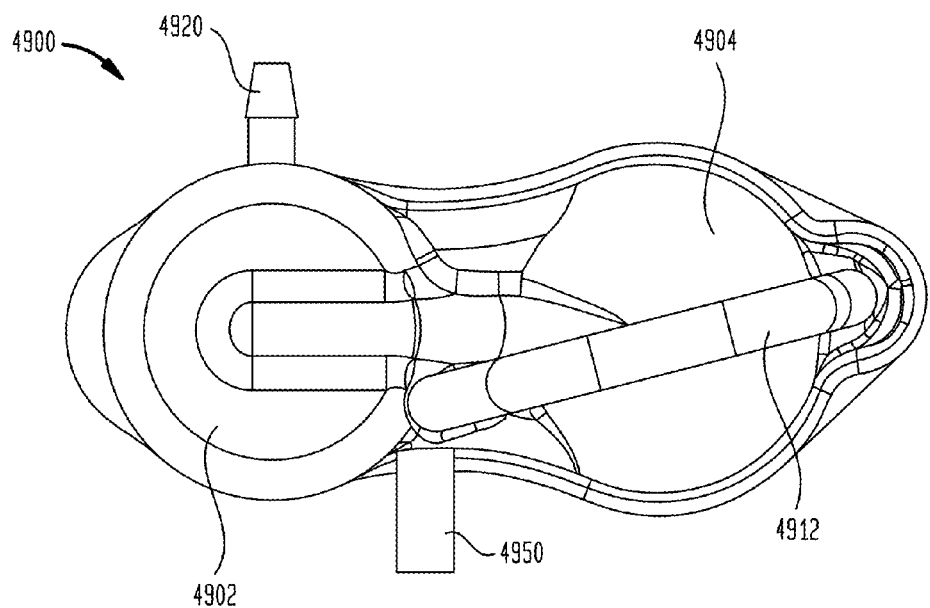
FIG. 49F is a top view of the flusher of FIG. 49A.
Figure 49G:
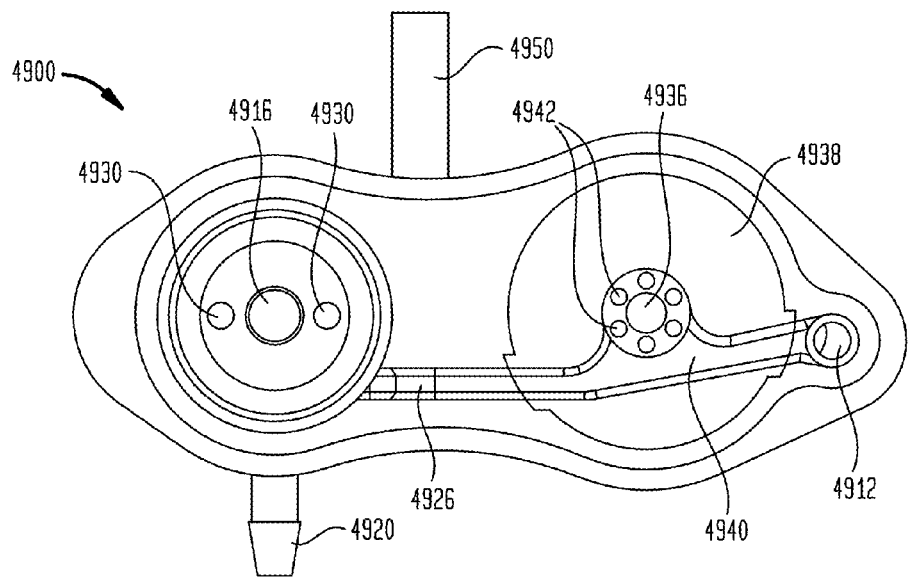
FIG. 49G is a bottom view of the flusher of FIG. 49A with a base plate removed.
Figure 50A:
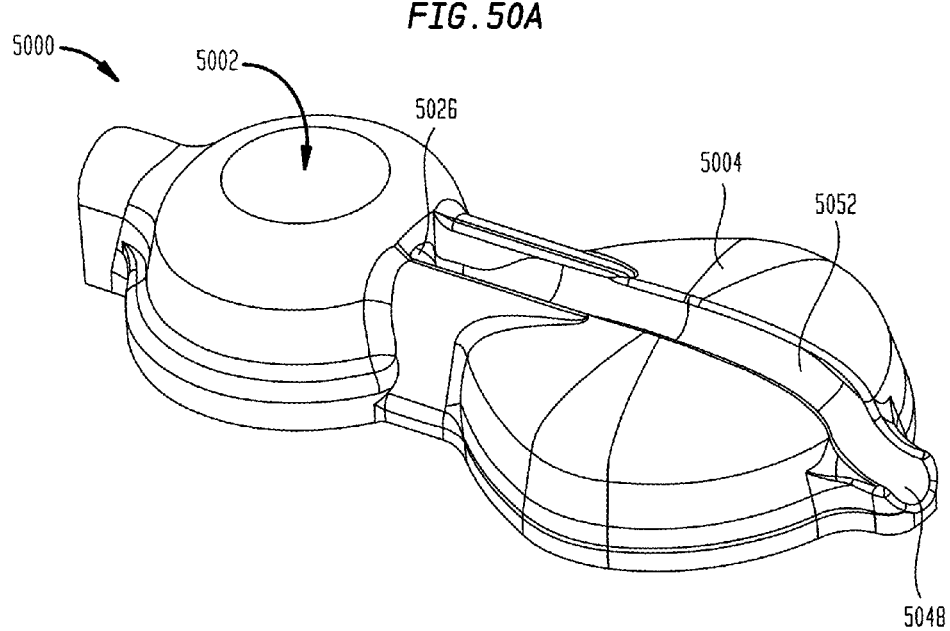
FIG. 50A is a perspective view from above of a flusher with a pinch tube removed.
Figure 50B:
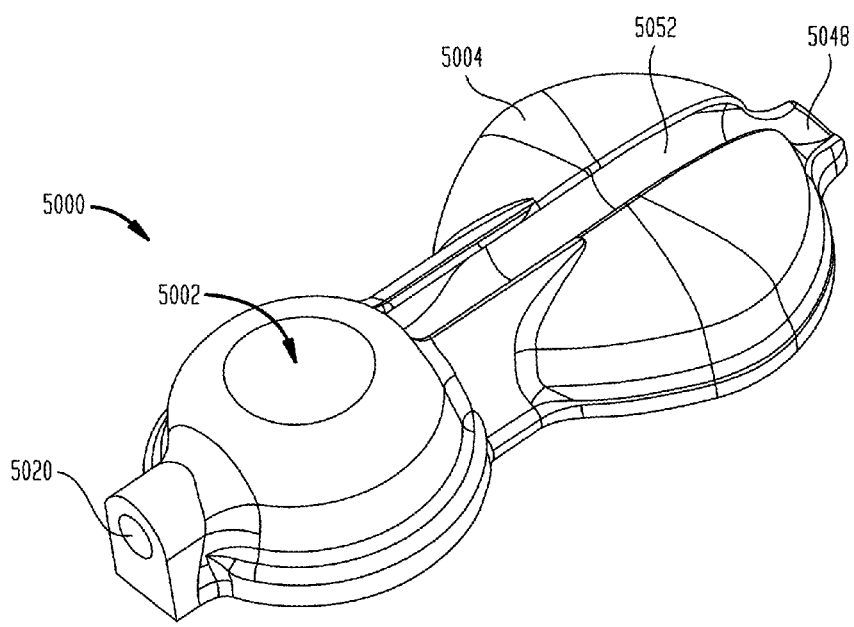
FIG. 50B is another perspective view from above of the flusher of FIG. 50A.
Figure 50C:
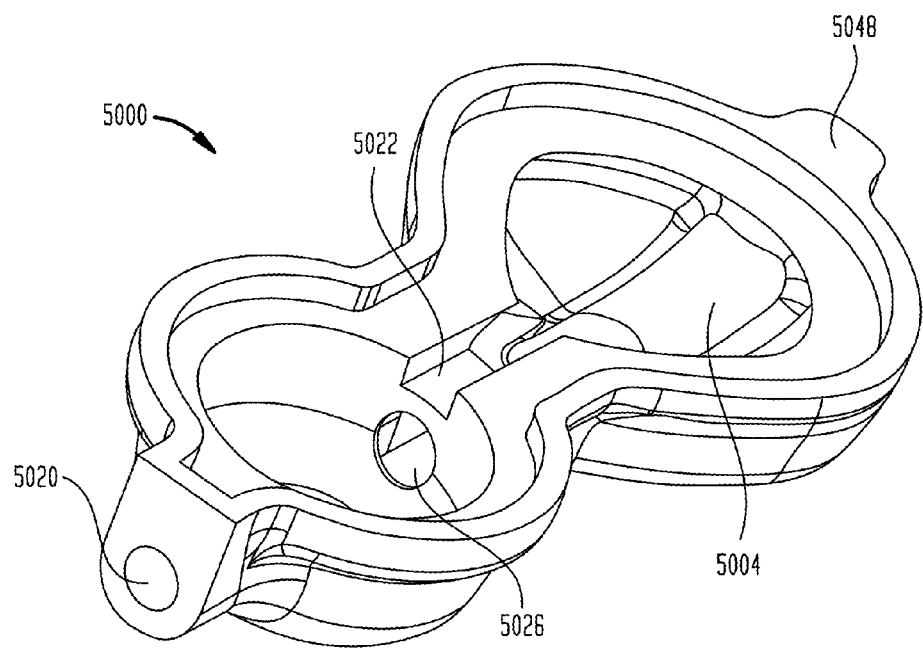
FIG. 50C is a perspective view from below of the body of the flusher of FIG. 50A.
Figure 50D:
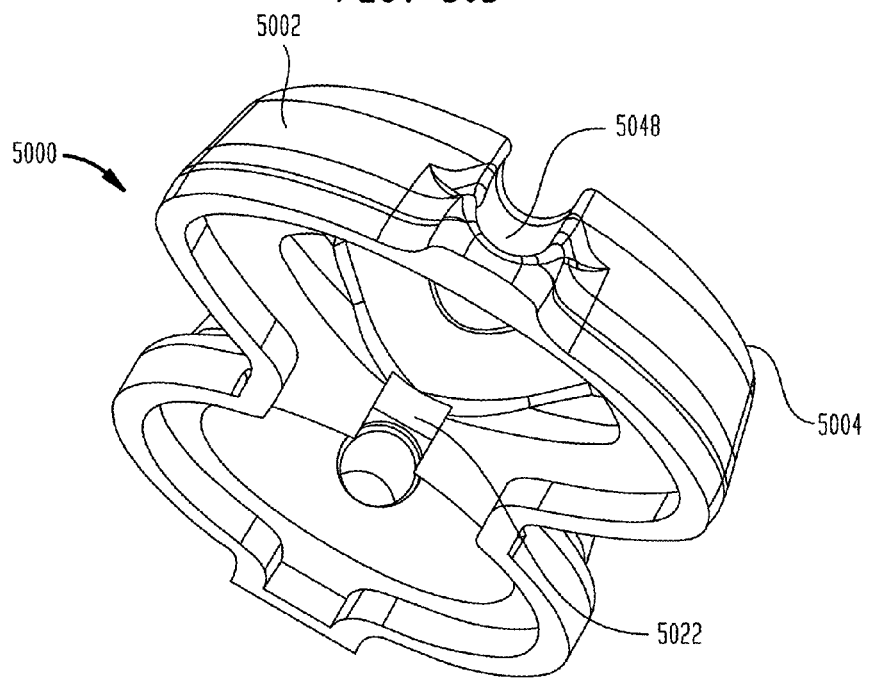
FIG. 50D is another perspective view from below of the body of the flusher of FIG. 50A.
Figure 50E:
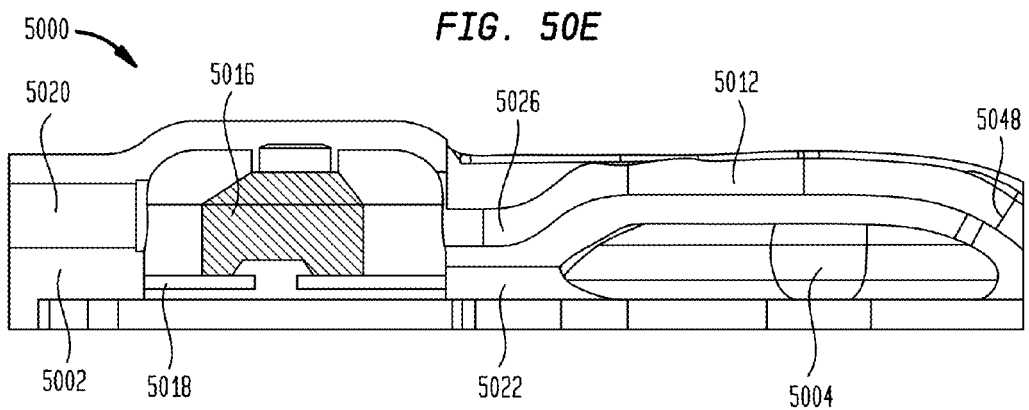
FIG. 50E is a longitudinal sectional view of the flusher of FIG. 50A.
Figure 50F:
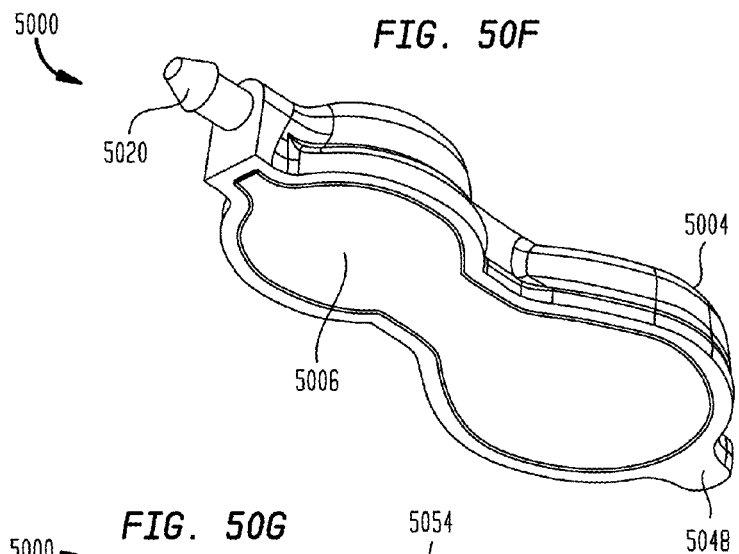
FIG. 50F is a perspective view from below of the flusher of FIG. 50A.
Figure 50G:
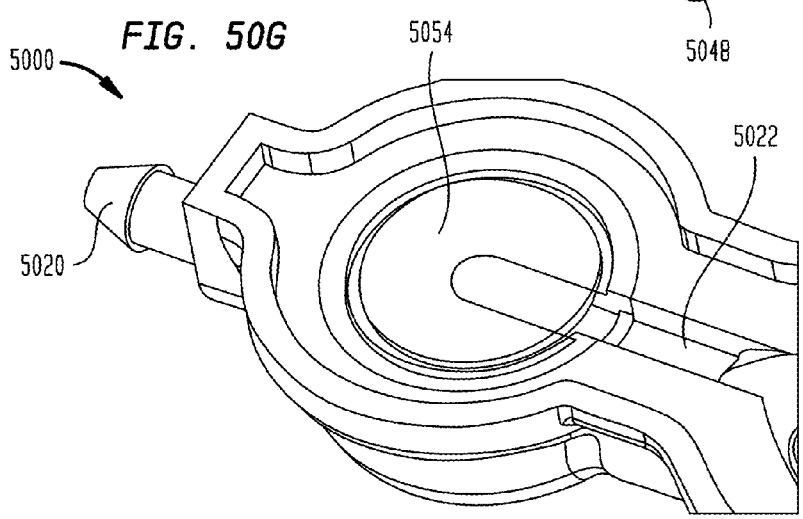
FIG. 50G is a perspective view from below of the flusher of FIG. 50A with a base plate removed.
Figure 50H:
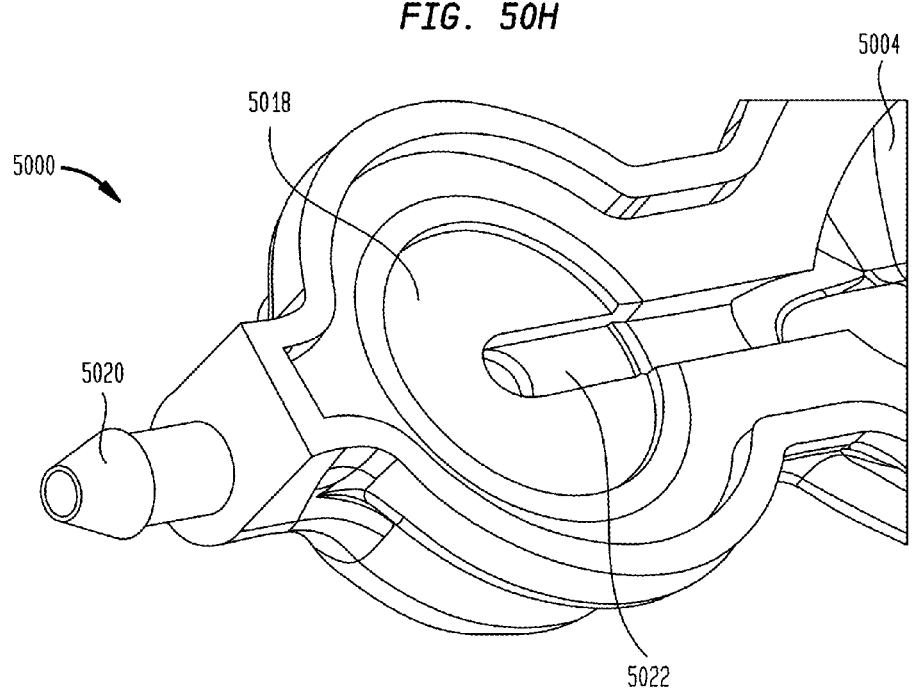
FIG. 50H is a perspective view from below of the flusher of FIG. 50A with a flush channel cover removed.
Figure 50I:
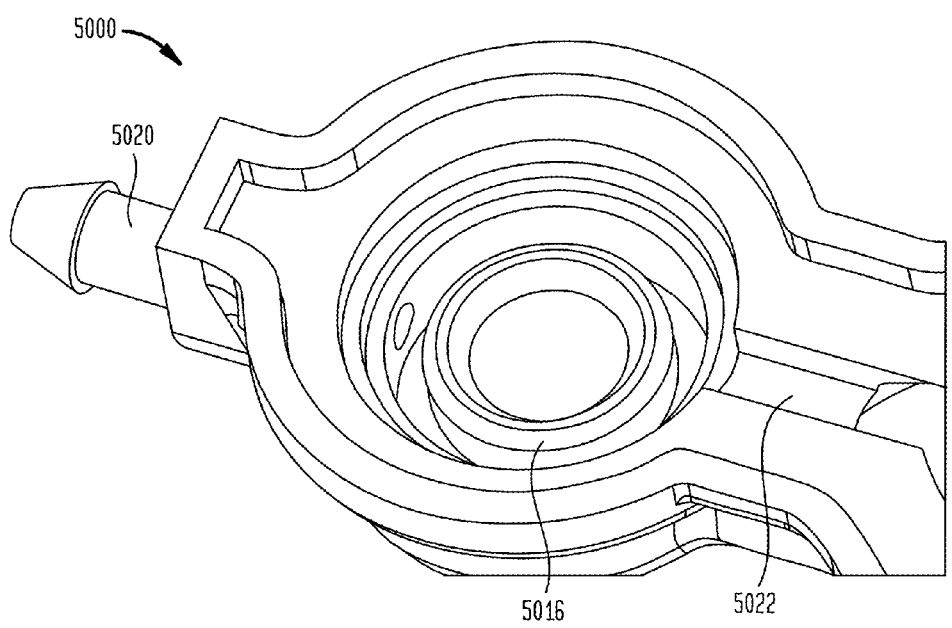
FIG. 50I is a perspective view from below of the flusher of FIG. 50A with a valve seat removed.

As shown in FIGS. 49F and 49G, the flusher 4900 employs a substantially T-shaped configuration in which the longitudinal axis of the flusher body 4902 extends perpendicular to the longitudinal axis of the upstream port 4920 and the longitudinal axis of the drain tube 4950. This can advantageously allow the flusher 4900 to be used with existing shunt systems without increasing the distance between the anchor and the shunt valve. The T-configuration can thus reduce or eliminate the need to add length to the overall shunt system, and allows the flusher 4900 to be positioned more proximate to an incision over the burr hole that is typically used when implanting shunt systems.

The flusher 4900 can be operable in a passive flow mode, a flushing mode, and a refill mode.

During the passive flow mode of operation, the flush valve 4916 and the refill valve 4936 are both closed. Fluid from a ventricular catheter flows into the valve cartridge 4914 via the upstream port 4920. The fluid flows around the closed valve body 4916 and into the passive flow port 4924 of the valve cartridge 4914. From there, the fluid flows through the passive flow channel 4926 of the body 4902 and through the passive flow channel 4940 of the refill plate 4938, past the closed refill valve 4936. The fluid then flows through the pinch tube 4912, into the drain tube 4950, and then into a shunt valve, drain catheter, or other downstream component of the shunt system.

A user can initiate a flushing operation by applying pressure to the top of the flush dome 4904 (e.g., by exerting downward finger pressure on the dome through a patient's skin), to collapse or compress the dome. During the flushing mode of operation, the pinch tube 4912 collapses under the pressure being applied by the user to cut off fluid communication to the drain tube 4950 and the downstream components of the shunt system. As the flush dome 4904 is depressed, the pressure in the flush dome increases, holding the refill valve 4936 in the closed position. The pressure in the flush dome 4904 increases until the threshold pressure of the flush valve 4916 is reached, at which point the flush valve opens releasing a cough or burst of fluid into the valve cartridge 4914. The collapsed pinch tube 4912 prevents the burst of fluid from flowing through the passive flow channels 4926, 4940, and therefore the burst of fluid instead flows through the upstream port 4920. This upstream "cough" or flush of fluid can be effective to clear obstructions from a ventricle catheter or other upstream component of the shunt system, or to open auxiliary flow paths as described further below. Once the burst of fluid is released, the flush valve 4916 returns to the closed position.

When a flushing operation is completed and the flush dome 4904 is released, the pinch tube 4912 opens to reestablish flow to the downstream port 4948 and the flush dome gradually returns to its raised position. During this refill mode of operation, the flush valve 4916 is closed. Expansion of the flush dome 4904 causes the pressure in the flush dome to drop below the pressure in the passive flow channel 4940, which creates a pressure differential that causes the refill valve 4936 to open. Fluid flowing through the passive flow channel 4940 can then flow through the openings 4942 formed in the refill plate 4938 to refill the flush dome 4904. The cross-sectional area of the openings 4942 can be made relatively small to limit the rate at which the flush dome 4904 is refilled and therefore the rate at which the flush dome expands. This can advantageously prevent debris flushed from the shunt system during the flushing operation from being sucked back in as the flush dome 4904 expands. Once the flush dome 4904 is refilled, the flusher 4900 returns to the passive flow mode of operation.

The flusher 4900 thus facilitates generation and application of a high pressure cough of fluid which flushes the ventricle side of the shunt system only. The pinch tube 4912 prevents the cough of fluid from travelling through the drain side of the shunt system. In other embodiments, however, the flusher 4900 can be configured to flush the drain side of the system instead or in addition.

FIGS. 50A-50I illustrate another exemplary embodiment of a flusher 5000. The flusher 5000 includes a flush dome 5004 that has a recess 5052 formed in an outer surface thereof in which a pinch tube 5012 can be disposed. The pinch tube is compressed when the flush dome 5004 is depressed to seal off the drain side of the system and direct the cough of fluid towards the upstream side of the system.

During normal operation, fluid from a ventricular catheter flows into the flusher 5000 via an upstream port 5020. The fluid flows around a closed flush valve 5016, into a passive flow channel of the body 5026, and into a pinch tube 5012 disposed in the recess 5052 of the flush dome 5004. The fluid then flows into a shunt valve, drain catheter, or other downstream component of the shunt system.

A user can initiate a flushing operation by applying pressure to the top of the flush dome 5004 (e.g., by exerting downward finger pressure on the dome through a patient's skin), to collapse or compress the dome. During the flushing mode of operation, the pinch tube 5012 collapses under the pressure being applied by the user to cut off fluid communication to the downstream components of the shunt system. As the flush dome 5004 is depressed, the pressure in the flush dome increases until the threshold pressure of the flush valve 5016 is reached, at which point the flush valve deforms away from a valve seat 5018, opening the valve and releasing a cough or burst of fluid through the upstream port 5020. The cough of fluid flows out of the flush dome 5004, through a flush channel 5022 defined in the body 5002 and between the valve seat 5018 and a flush channel cover 5054, and through the flush valve 5016 to the upstream port 5020. This upstream "cough" or flush of fluid can be effective to clear obstructions from a ventricle catheter or other upstream component of the shunt system, or to open auxiliary flow paths as described further below. Once the burst of fluid is released, the flush valve 5016 returns to the closed position.

When a flushing operation is completed and the flush dome 5004 is released, the pinch tube 5012 opens to reestablish flow to the downstream port 5048 and the flush dome gradually returns to its raised position. During this refill mode of operation, the flush valve 5016 is closed. As the flush dome 5004 expands, it is refilled with fluid from the passive flow channel 5026 via a refill port (not shown). Any of a variety of refill port arrangements can be used, as discussed below. Once the flush dome is refilled, the flusher 5000 returns to the passive flow mode of operation.

Figure 51:
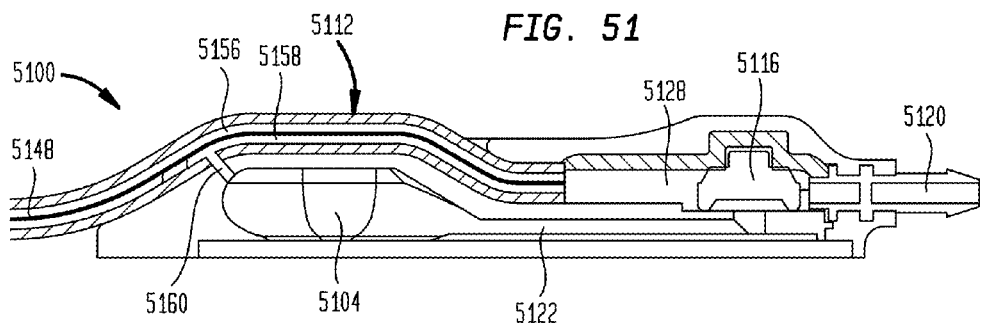
FIG. 51 is a longitudinal sectional view of a flusher.

FIG. 51 illustrates another exemplary embodiment of a flusher 5100. The flusher 5100 includes an upstream port 5120 configured to be coupled to or placed in fluid communication with a ventricular catheter and a downstream port 5148 configured to be coupled to or placed in fluid communication with a drain catheter or other downstream component of a shunt system. The flusher 5100 includes a flush dome 5104 and a flush valve 5116. Like the flusher 5000, the flusher 5100 does not include a dedicated refill valve. A dual lumen tube 5112 extends over the flush dome 5104 from the downstream port 5148 to the chamber 5128 in which the flush valve 5116 is disposed. A drain lumen 5156 of the tube 5112 is open to the downstream port 5148 while a refill lumen 5158 of the tube is closed just downstream of the flush dome 5104 and is in fluid communication with an interior of the flush dome via a refill port 5160. During normal operation, fluid flows from the upstream port 5120, around the flush valve 5116, through the drain lumen 5156 of the tube 5112 and out the downstream port 5148. The fluid also flows through the refill lumen 5158 of the tube 5112 to refill the flush dome 5104 if necessary. When the flush dome 5104 is actuated by a user, the drain and refill lumens 5156, 5158 are pinched off and pressure builds in the flush dome and a flush channel 5122 until the threshold pressure of the flush valve 5116 is reached, causing the flush valve to open and release a cough of fluid through the upstream port 5120.

Figure 52:
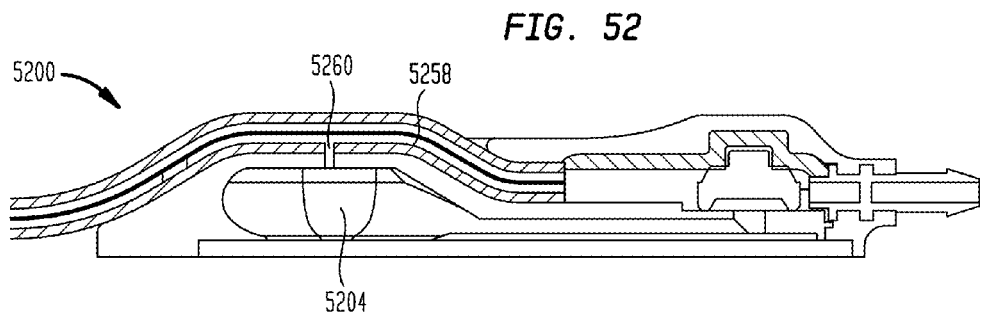
FIG. 52 is a longitudinal sectional view of another flusher.

FIG. 52 illustrates another exemplary embodiment of a flusher 5200. The flusher 5200 is substantially identical to the flusher 5100, except that the connection 5260 between the refill lumen 5258 and the flush dome 5204 is disposed at the apex of the flush dome (e.g., at the center of the upper wall of the flush dome). This can advantageously make it more likely that the refill port 5260 is blocked when the flush dome 5204 is being depressed by a user.

Figure 53:
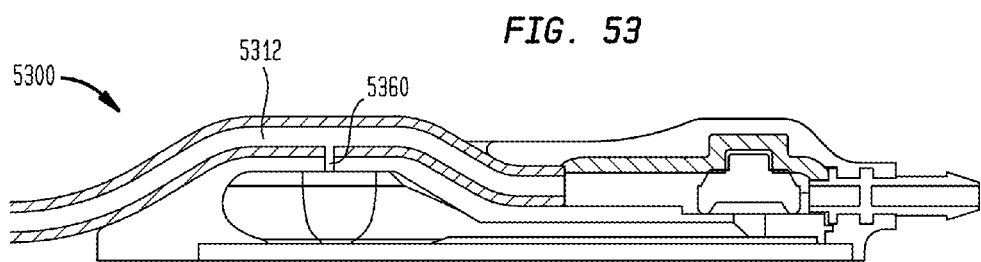
FIG. 53 is a longitudinal sectional view of another flusher.

FIG. 53 illustrates another exemplary embodiment of a flusher 5300. The flusher 5300 is substantially identical to the flusher 5100, except that the dual lumen tube is replaced with a single lumen tube 5312 that acts both as a drain lumen and as a refill lumen.

Figure 54:
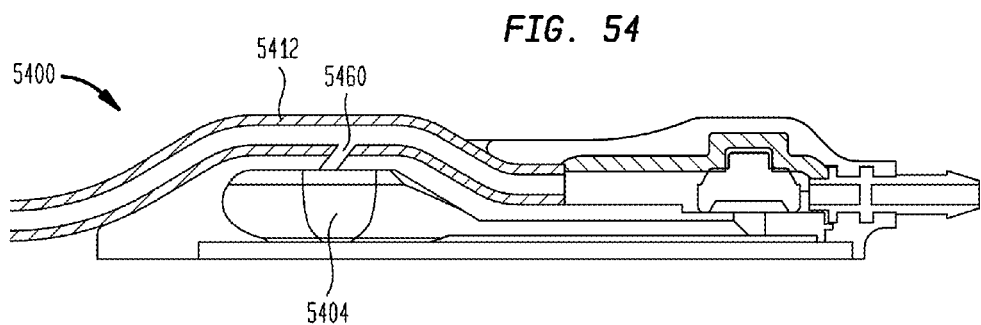
FIG. 54 is a longitudinal sectional view of another flusher.

FIG. 54 illustrates another exemplary embodiment of a flusher 5400. The flusher 5400 is substantially identical to the flusher 5300, except that the refill connection 5460 between the tube 5412 and the flush dome 5404 extends at an oblique angle relative to the central longitudinal axis of the tube. This can advantageously make it more likely that the refill port 5460 is blocked when the flush dome 5404 is depressed by a user, since a force applied away from the center of the flush dome will more easily result in the connection being sealed off.

Figure 55:
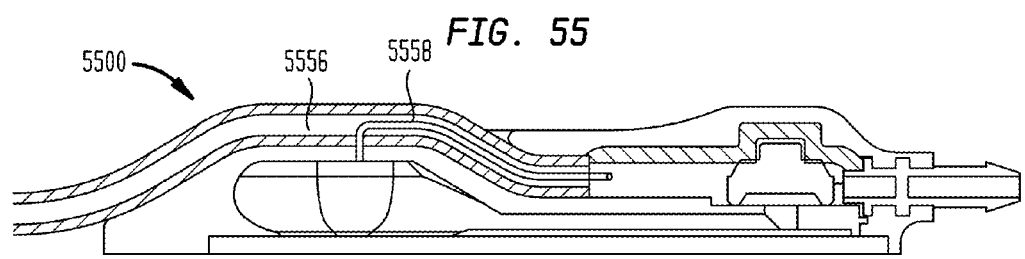
FIG. 55 is a longitudinal sectional view of another flusher.

FIG. 55 illustrates another exemplary embodiment of a flusher 5500. The flusher 5500 is substantially identical to the flusher 5100, except that the dual lumen tube is replaced with a single lumen tube 5556 having an inner tube 5558 nested therein.

Figure 56A:
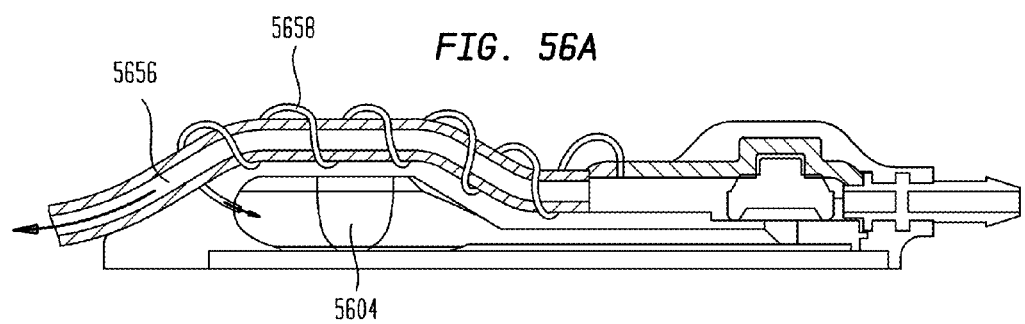
FIG. 56A is a schematic diagram of one exemplary arrangement of refill and drain lumens with respect to a flush dome.
Figure 56B:
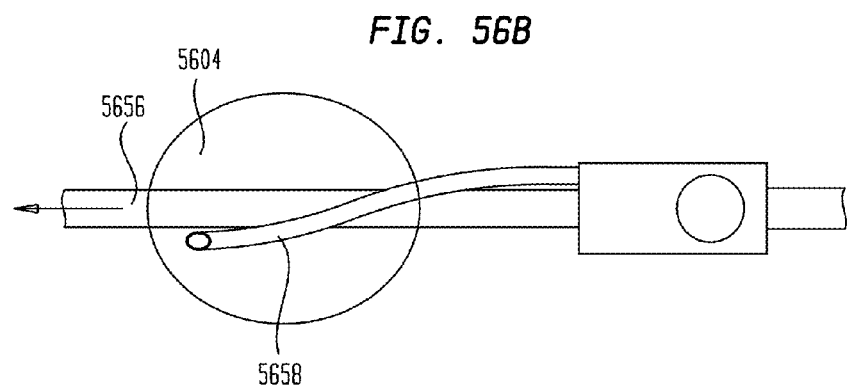
FIG. 56B is a schematic diagram of another exemplary arrangement of refill and drain lumens with respect to a flush dome.
Figure 56C:
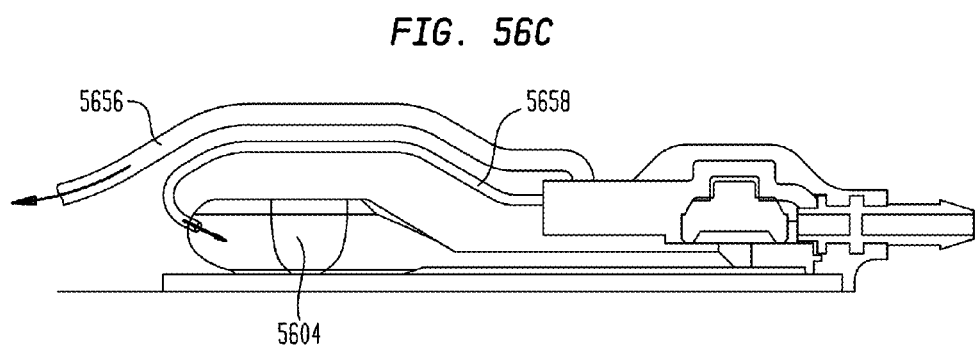
FIG. 56C is a schematic diagram of another exemplary arrangement of refill and drain lumens with respect to a flush dome
Figure 56D:
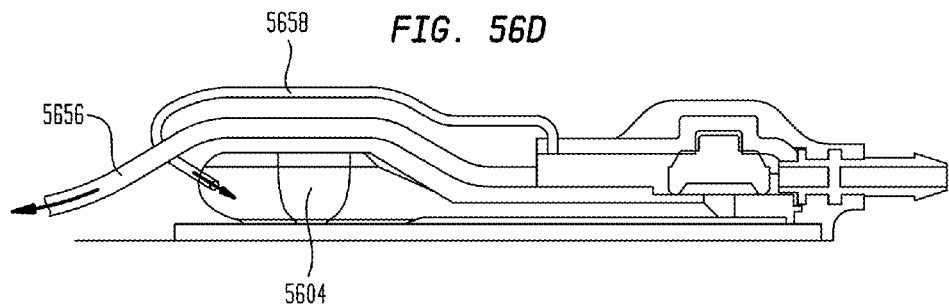
FIG. 56D is a schematic diagram of another exemplary arrangement of refill and drain lumens with respect to a flush dome.
Figure 56E:
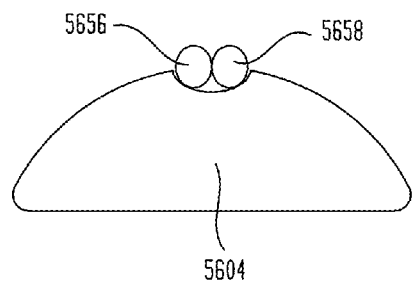
FIG. 56E is a schematic diagram of another exemplary arrangement of refill and drain lumens with respect to a flush dome.

It will be appreciated that various other arrangements can be employed to provide a refill lumen and a drain lumen that are closed off when the flush dome is actuated by a single user motion. For example, as shown in FIG. 56A, the refill lumen 5658 can be coiled around the drain lumen 5656 and the refill and drain lumens can extend over the top of the flush dome 5604 where a user is likely to apply pressure when actuating the dome. As shown in FIG. 56B, the refill lumen 5658 can cross over the drain lumen 5656 at a position that lies over the center of the flush dome 5604 where a user is likely to apply pressure when actuating the dome. As shown in FIG. 56C, the drain lumen 5656 can be stacked on top of the refill lumen 5658 and the refill and drain lumens can extend over the top of the flush dome 5604 where a user is likely to apply pressure when actuating the dome. As shown in FIG. 56D, the refill lumen 5658 can be stacked on top of the drain lumen 5656 and the refill and drain lumens can extend over the top of the flush dome 5604 where a user is likely to apply pressure when actuating the dome. As shown in FIG. 56E, the drain and refill lumens 5656, 5658 can extend side-by-side in a parallel relationship over the top of the flush dome 5604 where a user is likely to apply pressure when actuating the dome.

Figure 56F:
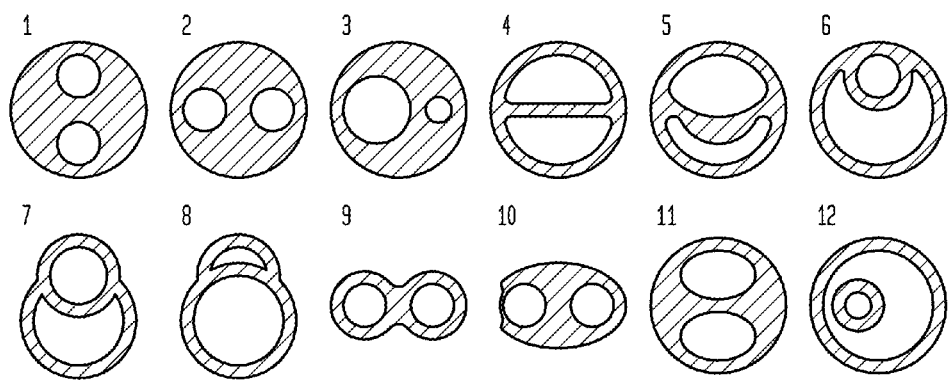
FIG. 56F is a series of sectional views of various pinch tube extrusion profiles.

As shown in FIG. 56F, any of a variety of sectional profiles can be used in the refill/drain tube of a flusher. The illustrated profiles are: 1) vertically-stacked circular cross section lumens of equal size; 2) horizontally-stacked circular cross section lumens of equal size; 3) horizontally-stacked circular cross section lumens of unequal size; 4) vertically stacked lumens having semi-circular cross sections; 5) a first lumen having a circular cross section and a second lumen having a crescent cross section, the circular lumen having a greater area than the crescent lumen; 6) a first lumen having a circular cross section and a second lumen having a crescent cross section, the crescent lumen having a greater area than the circular lumen, the overall cross-section of the tube being circular; 7) a first lumen having a circular cross section and a second lumen having a crescent cross section, the crescent lumen having a greater area than the circular lumen, the overall cross-section of the tube being non-circular; 8) a first lumen having a circular cross section and a second lumen having a crescent cross section, the circular lumen having a greater area than the crescent lumen, the overall cross-section of the tube being non-circular; 9) first and second lumens having circular cross sections, the overall cross-section of the tube being non-circular; 10) first and second lumens having circular cross sections, the overall cross-section of the tube being elliptical; 11) first and second lumens having elliptical cross sections, the overall cross-section of the tube being circular; and 12) first and second coaxial lumens each having a circular cross section.

Figure 56G:
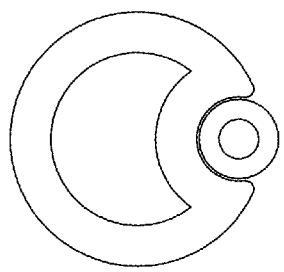
FIG. 56G is a sectional view of a multi-component pinch tube.
Figure 56H:
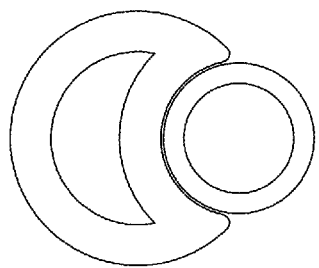
FIG. 56H is a sectional view of another multi-component pinch tube.

The first and second lumens can be coextruded or can be formed from two separate components joined together to form a composite tube. FIG. 56G illustrates a larger crescent shaped tube to which a circular tube is coupled to form a composite tube having a circular overall cross-section. FIG. 56H illustrates a larger crescent shaped tube to which a circular tube is coupled to form a composite tube having a non-circular overall cross-section.

The extrusion cross-section can be selected to control whether the refill and drain functions are closed off simultaneously or sequentially. When the refill and drain functions are to be closed off sequentially, the lumen assigned to the refill function and the lumen assigned to the drain function can be selected to control which function is closed off first when the tube is compressed. For example, in the extrusion profile enumerated above as number 6, the crescent-shaped lumen will close off before the circular-shaped lumen does.

Figure 57:
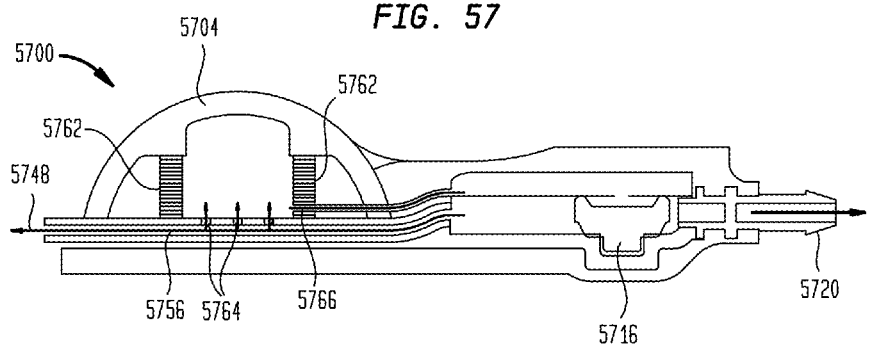
FIG. 57 is a longitudinal sectional view of another flusher.

FIG. 57 illustrates another exemplary embodiment of a flusher 5700. The flusher 5700 includes an upstream port 5720 configured to be coupled to or placed in fluid communication with a ventricular catheter and a downstream port 5748 configured to be coupled to or placed in fluid communication with a drain catheter or other downstream component of a shunt system. The flusher 5700 includes a flush dome 5704 and a flush valve 5716. A ring 5762 is disposed within the flush dome 5704 above the drain lumen 5756. During normal operation, fluid flows from the upstream port 5720, around the flush valve 5716, through the drain lumen 5756 and out the downstream port 5748. The fluid also flows through openings 5764 in the drain lumen 5756 to refill the flush dome 5704 if necessary. When the flush dome 5704 is actuated by a user, the ring 5762 pinches down on the drain lumen 5756 to close off the drain side of the system. Fluid flows through an opening 5766 formed in the ring 5762 against the flush valve 5716 and pressure builds until the threshold pressure of the flush valve is reached, causing the flush valve to open and release a cough of fluid through the upstream port 5720.

It will be appreciated that, in any of the flusher embodiments above, the pinch tube or lumen can be disposed below the flush dome instead of on top of the flush dome as shown.

In any of the flushers disclosed herein, the flush dome can be sized to control the volume of fluid flushed through the shunt system during a flushing operation. In an exemplary embodiment, the flush dome has an interior volume of about 1 mL. In any of the flushers disclosed herein, the flush dome can be configured to rebound or return to its un-collapsed configuration at a slow rate to prevent reflux action from sucking debris back into the shunt system. For example, the dome can be formed from a material having low resiliency properties such as polymeric compositions, silicone, nitrile, polyurethane, and so forth. Alternatively, or in addition, the dome can include ribs or other internal or external features for controlling the rebound rate of the dome. For example, the dome can include one or more ribs that extend from the base of the dome to the center peak of the dome. The ribs can extend along the interior surface of the dome. Alternatively, or in addition, the thickness of the dome can vary between the base and the peak. For example, the dome can be thicker at the base than at the peak. While flushers configured to flush only the upstream or ventricular side of the shunt system are disclosed herein, it will be appreciated that the disclosed flushers can be readily modified to flush only the downstream or drain side of the shunt system and/or to flush both sides of the shunt system.

Auxiliary Flow Features

In the flusher embodiments disclosed herein, a cough or flush of fluid is directed into components of a shunt system disposed upstream from the flusher (e.g., into a ventricular catheter) to clear obstructions from the catheter or to open alternative flow paths through the catheter. A variety of components (e.g., catheters, switches, etc.) are disclosed in the description that follows, any of which can be used with any of the flushers disclosed above in accordance with the teachings herein. In addition, the components disclosed in the description that follows can be used with other flushers or, in some instances, without a flusher. Further still, the components disclosed in the description that follows can be used in the upstream or ventricular side of the shunt system and/or in the downstream or drain side of the shunt system. Any of the features of the catheters 102, 202 disclosed above can be included in any of the catheters disclosed below.

Figure 28A:
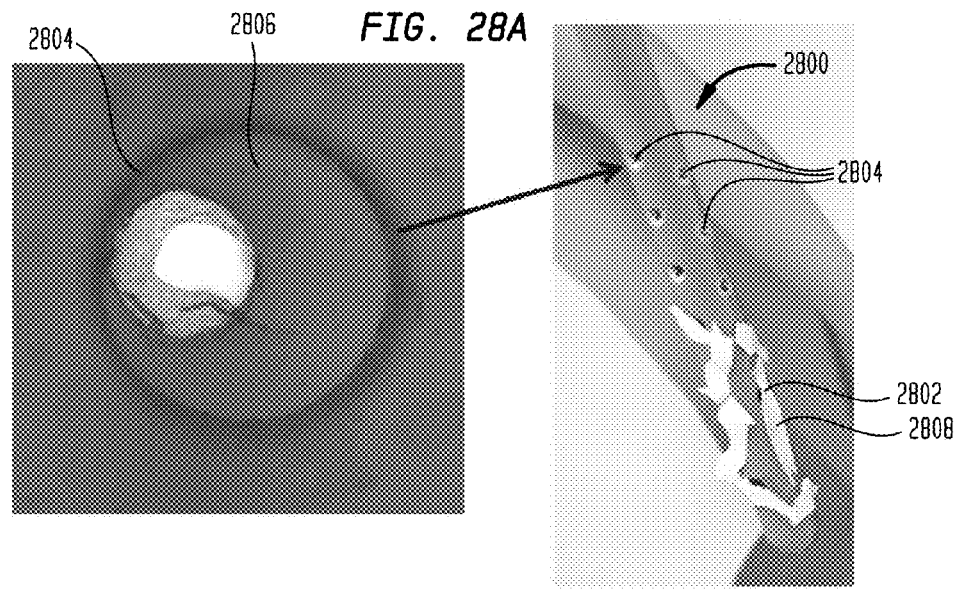
FIG. 28A is a perspective view of a catheter having clogged primary fluid inlet ports with an inset of an auxiliary fluid inlet port after a membrane disposed over the port is ruptured.
Figure 28B:
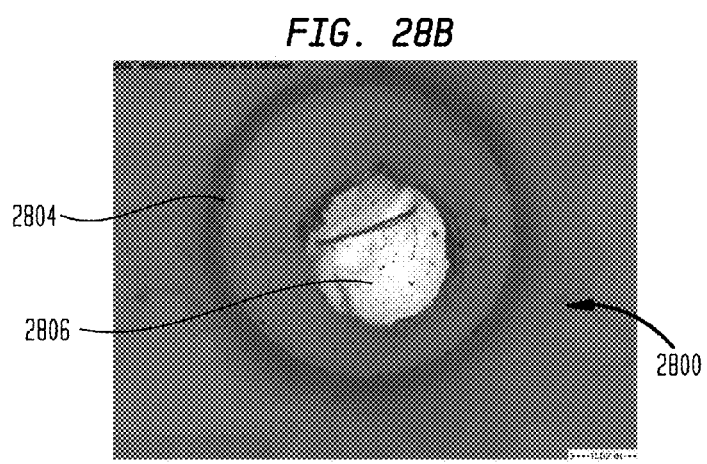
FIG. 28B is a plan view of an auxiliary fluid inlet port of the catheter of FIG. 28A after a non-tensioned membrane disposed over the port is ruptured.
Figure 28C:
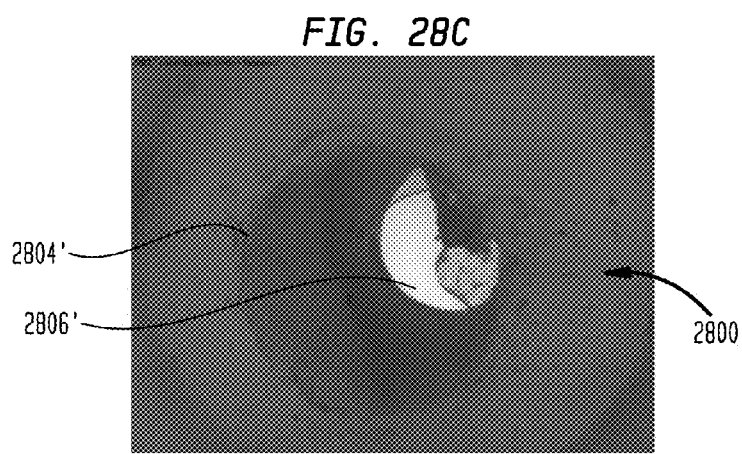
FIG. 28C is a plan view of an auxiliary fluid inlet port of the catheter of FIG. 28A after a tensioned membrane disposed over the port is ruptured.

FIGS. 28A-28C illustrate an exemplary embodiment of a catheter 2800. The catheter 2800 includes a plurality of inlet holes formed at a distal tip end of the catheter configured to be disposed within a patient's ventricle. While a single-lumen, single-tip catheter is shown, it will be appreciated that the catheter can be a multi-lumen catheter and/or a multi-tip catheter. For example, the catheter can be a dual lumen catheter with two independent lumens that extend the full length of the catheter. By way of further example, the catheter can be a split-tip catheter having first and second tips at the distal end that merge into a single lumen that extends through the remainder of the catheter.

The plurality of inlet holes includes one or more primary holes 2802 which form pathways through which fluid external to the catheter 2800 can enter an inner lumen of the catheter. The plurality of inlet holes also includes one or more auxiliary holes 2804 which are initially blocked such that fluid external to the catheter 2800 cannot pass through the auxiliary holes into an inner lumen of the catheter. Rather, fluid can only pass through the auxiliary holes 2804 after they are forced open (e.g., by a flushing operation of one of the flushers disclosed above). The auxiliary holes 2804 are initially blocked by a membrane 2806. In some embodiments, the membrane 2806 can be disposed over the exterior surface of the catheter 2800. The membrane 2806 can be formed from a variety of implantable and biocompatible materials, such as silicone. The membrane 2806 can be stretched across the openings 2804 and attached to the catheter 2800 under tension, such that penetration of the membrane results in a tear in which opposed sides of the tear move out of the way of the underlying hole. The membrane 2806 can be stretched over the auxiliary holes 2804 in a variety of directions or orientations, which can allow for the tear produced when the membrane is ruptured to have some directionality (i.e., to define an opening that faces in a particular direction). The stretched membrane 2806 can be attached to the catheter 2800 in various ways. For example, the membrane 2806 can be thermally welded to the catheter 2800 using a heat punch, mechanically coupled to the catheter using O-rings disposed around the membrane and the catheter, or molded into or onto the catheter. In some embodiments, a plurality of auxiliary holes can be provided, each having a membrane stretched in a different direction. The thickness of the membrane, the degree of tension applied to the membrane, and the material from which the membrane is formed can be selected to control the force required to tear the membrane. In some embodiments, the membrane is formed from silicone and has a thickness of about 0.001 inches.

In use, the catheter 2800 is implanted in a patient with the distal tip of the catheter disposed in the patient's ventricle. Fluid enters the primary holes 2802 of the catheter and flows through the inner lumen of the catheter to a downstream portion of the shunt system (e.g., a flusher, a valve, and/or a drain catheter). When the primary holes 2802 become clogged or obstructed, or at any other time a user so desires, a flusher can be actuated to deliver a pressurized cough of fluid through the inner lumen of the catheter. The cough of fluid can dislodge obstructions 2808 from the clogged primary holes 2802 and/or cause the membrane 2806 covering one or more auxiliary holes 2804 to burst. In other words, flushing the catheter can open the auxiliary inlet ports 2804 to provide a secondary fluid pathway into the catheter, e.g., when the primary fluid pathway becomes clogged or obstructed.

The inset of FIG. 28A shows an auxiliary hole 2804 after the membrane 2806 disposed over the hole has been ruptured. FIG. 28B shows a membrane 2806 disposed over the catheter without stretching after being ruptured and FIG. 28C shows a membrane 2806' disposed over the catheter with stretching after being ruptured. As shown, the stretched membrane provides a larger opening after rupture, since the torn away portion of the pre-tensioned membrane is pulled away from the auxiliary hole 2804'.

Figure 29:
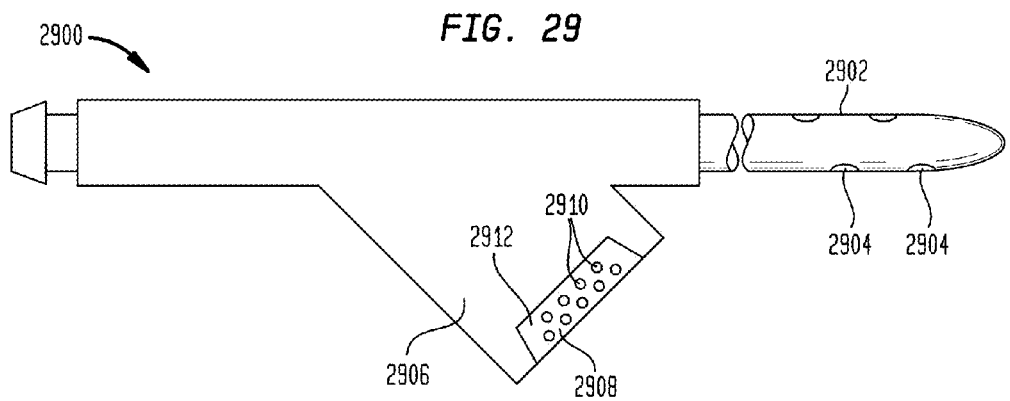
FIG. 29 is a plan view of a catheter having an auxiliary tip with a cylindrical plug.

FIG. 29 illustrates another exemplary embodiment of a catheter 2900. The catheter 2900 includes a primary tip 2902 with one or more inlet holes 2904 through which fluid can pass to enter the inner lumen of the primary tip. The catheter 2900 also includes an auxiliary tip 2906 with a cylindrical plug 2908 mounted therein. The plug 2908 includes one or more auxiliary holes 2910 covered by a membrane 2912 of the type disclosed above which can be ruptured (e.g., by a flushing cough) to open the auxiliary holes. The plug 2908 can be formed from a rigid material. In some embodiments the plug 2908 can be about 3-5 mm in diameter.

Figure 30:
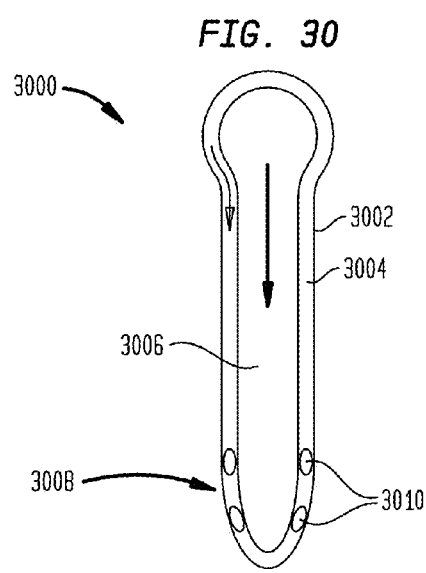
FIG. 30 is a sectional view of a catheter having a stretchable bulb-shaped distal end.

FIG. 30 illustrates another exemplary embodiment of a catheter 3000. The sidewall 3002 of the catheter has a fluid lumen 3004 formed therein, such that fluid can flow through the interior lumen 3006 of the catheter and through the sidewall of the catheter. When a flusher downstream from the catheter 3000 is actuated, the flushing fluid causes the sidewall lumen 3004 to expand, stretching a bulb-shaped terminal distal end 3008 of the catheter like a balloon. As the bulb 3008 is stretched, one or more inlet holes 3010 formed therein are enlarged, which can free any debris that is lodged in the inlet holes. In other words, the flushing operation is effective to stretch open pores 3010 formed in the catheter 3000 to clear obstructions.

Figure 31:
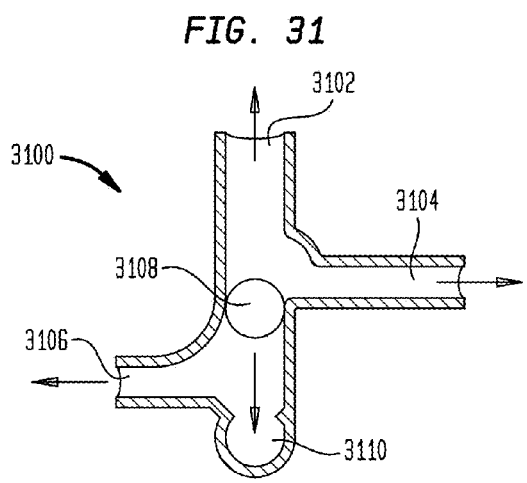
FIG. 31 is a sectional view of a ball and detent bypass switch.

FIG. 31 illustrates an exemplary embodiment of a catheter bypass switch 3100. The bypass switch 3100 can be incorporated into a flusher or into the ventricular catheter itself. The switch 3100 includes a flush channel 3102 which can be coupled to the ventricle port of a flusher. The switch 3100 also includes primary and secondary catheter channels 3104, 3106 which can be coupled to respective independent lumens of a dual-lumen catheter or to two separate catheters. A ball valve 3108 is disposed in the switch above a detent or recess 3110 sized to receive the ball when the ball is forced downward by fluid being flushed through the flush channel 3102. In operation, the switch is initially configured as shown in FIG. 31 such that fluid expelled from the flusher in a flushing operation flows through the primary catheter to clear any blockages or obstructions. If the flush is unable to clear some or all of the obstructions in the primary catheter, the pressure acting on the ball 3108 can increase to a point where the friction between the ball and the sidewall of the switch 3100 is overcome and the ball moves down into the detent 3110. This opens the secondary channel 3106 such that fluid can then flow from the patient's ventricle, through the secondary catheter, and into the flusher and the downstream portion of the shunt system. The opening into the detent 3110 can spring back around the ball 3108 after the ball is forced into the detent, such that the ball remains in the detent (and the secondary channel 3106 remains open) after the flushing force is removed. Because fluid does not flow through the secondary catheter until the switch 3100 is actuated, there is a reduced tendency for debris to flow into and clog the secondary catheter while it is not being used.

Figure 32:
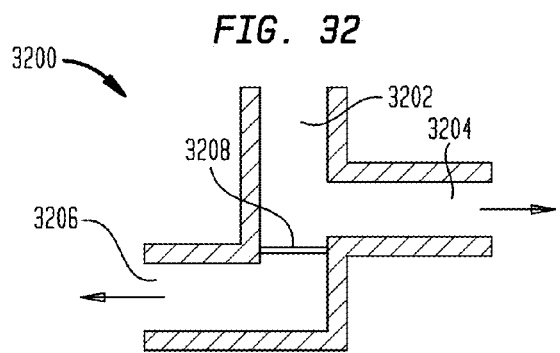
FIG. 32 is a sectional view of a membrane bypass switch.

FIG. 32 illustrates another exemplary embodiment of a catheter bypass switch 3200. The bypass switch 3200 can be incorporated into a flusher or into the ventricular catheter itself. The switch 3200 includes a flush channel 3202 which can be coupled to the ventricle port of a flusher. The switch also includes primary and secondary catheter channels 3204, 3206 which can be coupled to respective independent lumens of a dual-lumen catheter or to two separate catheters. A sealing membrane 3208 is disposed in the switch 3200 across the secondary catheter channel 3206 such that the secondary catheter channel is initially sealed off from the rest of the switch. In operation, the switch 3200 is initially configured as shown in FIG. 32 such that fluid expelled from the flusher in a flushing operation flows through the primary catheter to clear any blockages or obstructions. If the flush is unable to clear some or all of the obstructions in the primary catheter, the pressure acting on the membrane 3208 can increase to a point where the membrane bursts. This opens the secondary channel 3206 such that fluid can then flow from the patient's ventricle, through the secondary catheter, and into the flusher and the downstream portion of the shunt system. The membrane 3208 can be self-sealing and/or resealable, or can be non-resealable such that the secondary channel 3206 is permanently opened, even after the flushing force is removed. Because fluid does not flow through the secondary catheter until the switch 3200 is actuated, there is a reduced tendency for debris to flow into and clog the secondary catheter while it is not being used.

Figure 33:
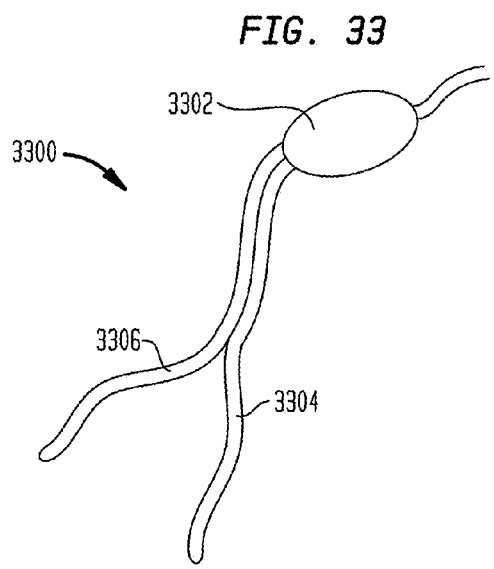
FIG. 33 is a perspective view of a push button bypass switch.

While the switches 3100, 3200 of FIGS. 31 and 32 are actuated by fluid pressure from a flushing operation, the switches can also be actuated mechanically. For example, as shown in FIG. 33, a switch 3300 can include a push button 3302 to which a force can be applied by a user through the patient's skin when a primary catheter 3304 is clogged. The push button 3302 can be coupled to a pointed stem configured to penetrate a membrane within the switch when the push button is depressed to open the membrane and allow fluid flow through a secondary catheter 3306. Alternatively, the push button can be coupled to a stem or lever configured to urge the ball of FIG. 31 into the detent to open the secondary catheter.

Figure 34:
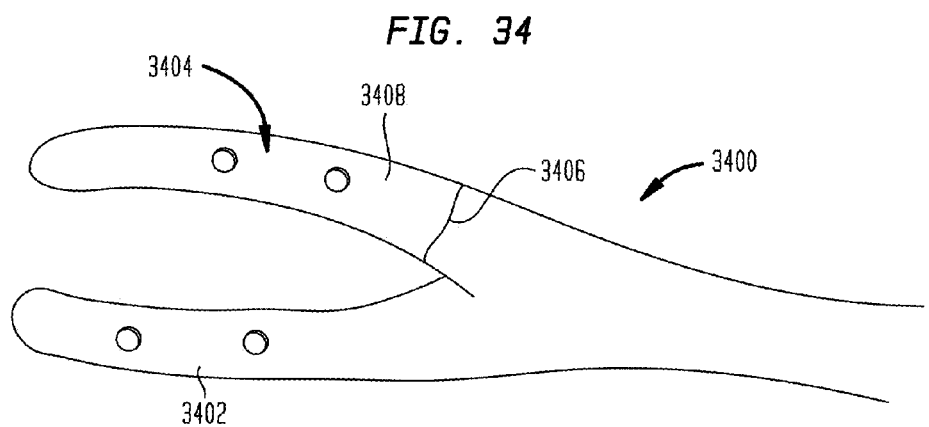
FIG. 34 is a sectional view of a split-tip catheter with an auxiliary tip sealed by a membrane.

FIG. 34 illustrates another exemplary embodiment of a catheter 3400. The catheter 3400 includes a split-tip distal end with a primary tip 3402 and a secondary tip 3404. The secondary tip 3404 is initially closed by a sealing membrane 3406 stretched across the interior lumen 3408 of the secondary tip. In use, the membrane 3406 can be ruptured (e.g., as described in the embodiments above) to open the secondary tip 3404 and allow fluid flow therethrough.

Figure 35A:
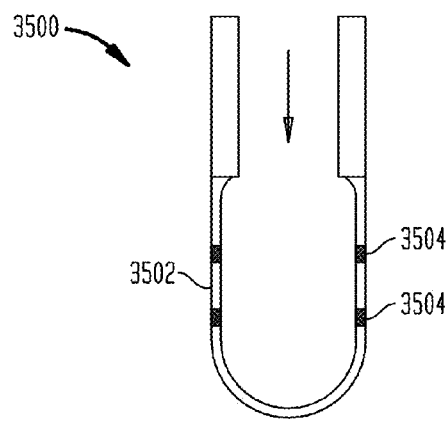
FIG. 35A is a sectional view of a catheter with a stretchable distal tip shown in a non-stretched position.
Figure 35B:
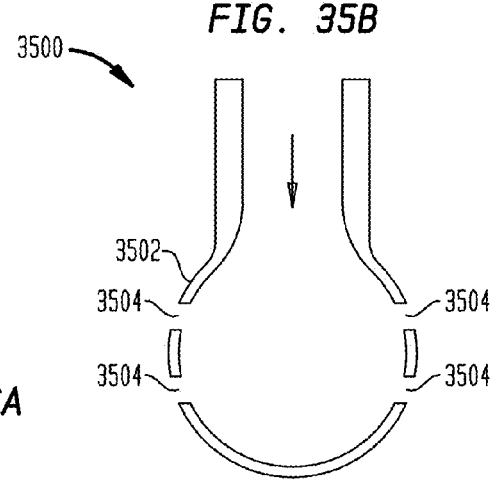
FIG. 35B is a sectional view of a catheter with a stretchable distal tip shown in a stretched position.

FIGS. 35A-35B illustrate another exemplary embodiment of a catheter 3500. The catheter 3500 includes a bulb portion 3502 at its terminal distal end that has a reduced sidewall thickness as compared with the rest of the catheter. One or more inlet ports 3504 are formed in the bulb portion 3502 of the catheter to allow fluid external to the catheter to flow into the inner lumen of the catheter. When the inlet ports 3504 are blocked or obstructed, a flushing operation can performed by a flusher disposed downstream from the catheter. The high pressure flush generated by the flusher causes the bulb 3502 to stretch, as shown in FIG. 35B, expanding the inlet ports 3504 and dislodging any debris or obstructions that may be caught in the inlet ports.

Figure 36A:
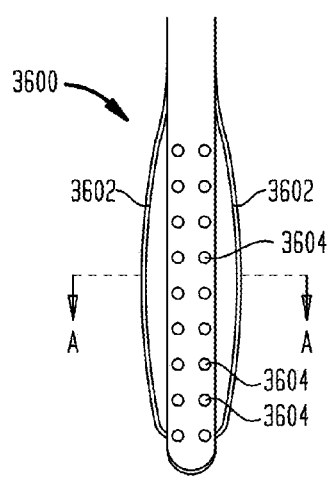
FIG. 36A is a plan view of a catheter with longitudinal stand-off ribs.
Figure 36B:
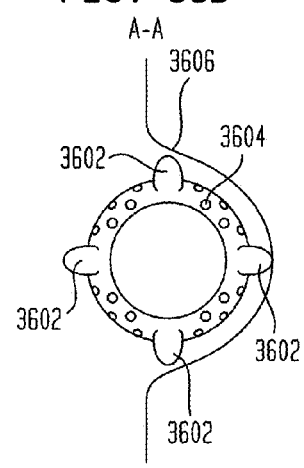
FIG. 36B is a sectional view of the catheter of FIG. 36A.

FIGS. 36A-36B illustrate another exemplary embodiment of a catheter 3600. The catheter 3600 includes one or more longitudinal ribs 3602 formed on an exterior surface thereof. In the illustrated embodiment, the catheter 3600 includes four external ribs 3602 spaced 90 degrees apart from one another about the circumference of the catheter. The ribs 3602 act as standoffs that hold the catheter 3600 and the inlet ports 3604 formed therein away from objects in the vicinity of the catheter (e.g., the wall of the patient's ventricle or other tissue 3606). Accordingly, when the catheter is disposed up against the side of the patient's ventricle or up against other tissue, a path remains open to the inlet ports on the side of the catheter facing the tissue.

Figure 37:
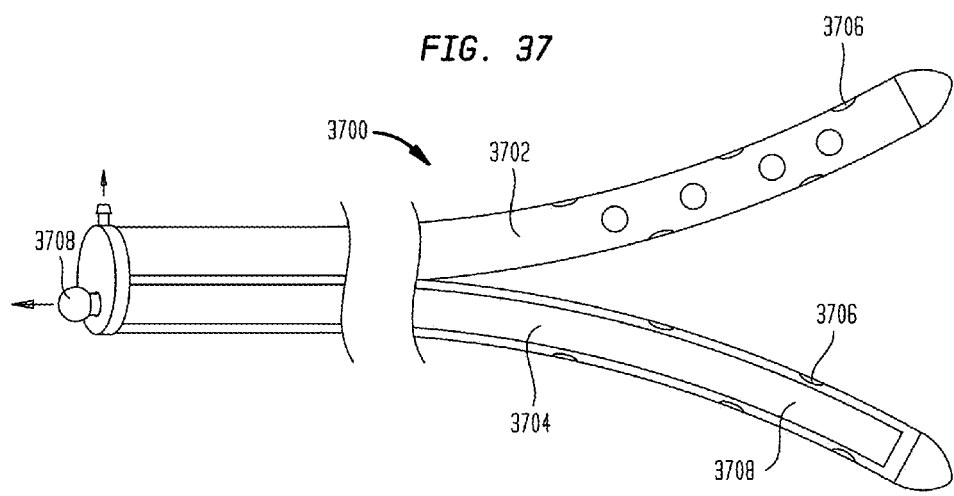
FIG. 37 is a perspective view of a dual lumen catheter with an auxiliary lumen sealed by a removable stylet.

FIG. 37 illustrates another exemplary embodiment of a catheter 3700. The catheter 3700 includes independent primary and secondary lumens 3702, 3704. Each lumen includes one or more inlet ports 3706 formed therein. In addition, a stylet 3708 is disposed in the secondary lumen 3704 to block fluid flow therethrough and through the inlet ports 3706 formed therein. In use, when the primary lumen 3702 becomes blocked or obstructed, the stylet 3708 can be removed to open up flow through the secondary lumen 3704. The stylet 3708 can be removed during a minimally-invasive surgical procedure in which a small incision is formed adjacent to the proximal end of the catheter 3700, the stylet is pulled out of the secondary lumen 3704, and the incision is closed. The catheter of FIG. 37 thus allows a secondary flow channel to be opened up with a minimally-invasive procedure, as compared with traditional ventricular catheters which, when clogged, must be completely removed and replaced with a new catheter as part of a comparatively more-invasive procedure.

Figure 38:
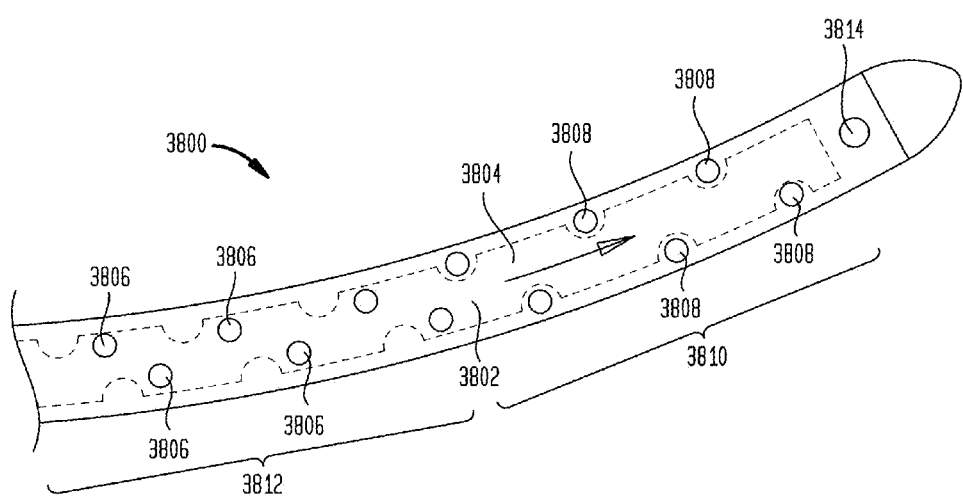
FIG. 38 is a sectional view of a catheter with a longitudinally-translatable inner sheath.

FIG. 38 illustrates another exemplary embodiment of catheter 3800. The catheter 3800 includes a sheath 3802 disposed within the inner lumen 3804 of the catheter and positioned such that the sheath blocks one or more auxiliary fluid inlet ports 3806 while leaving one or more primary fluid inlet ports 3808 open. For example, the sheath 3802 can include a first hole pattern 3810 that is aligned with the primary holes 3808, and a second hole pattern 3812 that is aligned with the auxiliary holes 3806 only when the sheath is translated longitudinally relative to the catheter 3800. When the primary ports 3808 become clogged or obstructed, the sheath 3802 can be advanced or retracted to expose one or more of the auxiliary inlet ports 3806. In the illustrated embodiment, the catheter 3800 includes a bleed hole 3814 adjacent to the distal end of the catheter which allows the sheath 3802 to move when a pressure differential is applied thereto. In particular, the bleed hole 3814 can allow fluid beneath the sheath 3802 to escape to reduce any pressure buildup that might prevent the sheath from advancing. In other embodiments, the sheath 3802 can include one or more protrusions that extend radially inward into the catheter. High pressure fluid flow generated by a flushing operation can exert a force on the protrusions which causes longitudinal translation of the sheath 3802 relative to the catheter 3800 to open up one or more of the auxiliary ports 3806. Alternatively, the sheath 3802 can be translated mechanically, for example by a lever or linkage system actuated by the flusher.

Figure 39A:
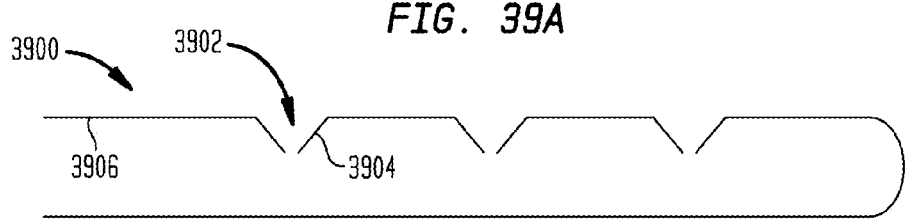
FIG. 39A is a sectional view of a catheter with conical flap inlet ports shown prior to a flushing operation.
Figure 39B:
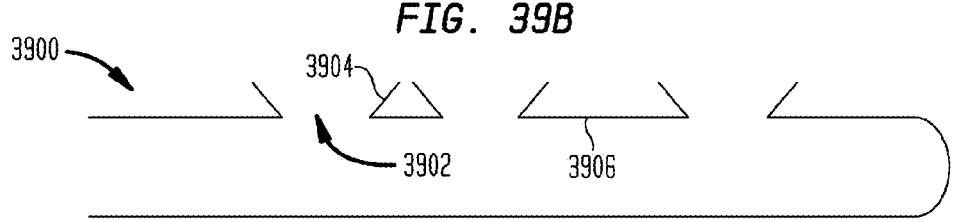
FIG. 39B is a sectional view of the catheter of FIG. 39A after a flushing operation.

FIGS. 39A-39B illustrate another exemplary embodiment of a catheter 3900. The catheter 3900 includes one or more fluid inlet ports 3902 defined by conical flaps 3904 that normally extend radially inward from the sidewall 3906 of the catheter as shown in FIG. 39A. When the inlet ports 3902 become clogged or obstructed, a flushing operation can be performed, which can cause the conical flaps 3904 to become inverted such that they extend radially outward from the exterior sidewall of the catheter, as shown in FIG. 39B. Transitioning the flaps 3904 to the outward position shown in FIG. 39B can be effective to dislodge any debris that may be clogging or obstructing fluid flow through the inlet ports 3902.

Figure 40A:
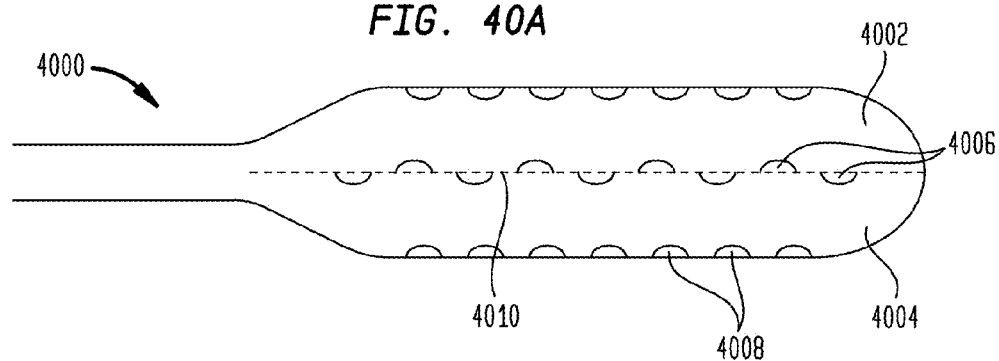
FIG. 40A is a sectional view of a split-tip catheter shown prior to a flushing operation.
Figure 40B:
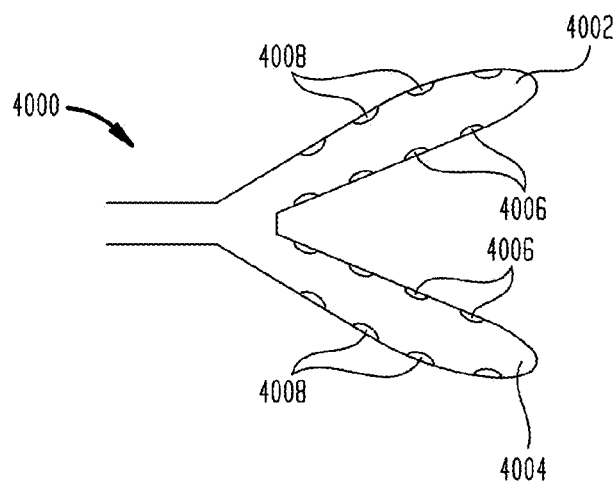
FIG. 40B is a sectional view of the catheter of FIG. 40A shown after a flushing operation.

FIGS. 40A-40B illustrate another exemplary embodiment of a catheter 4000. The catheter 4000 is a split-tip catheter in which the first and second tips 4002, 4004 are initially joined together. One or more fluid inlet ports 4006 are formed in the joined surfaces of the tips 4002, 4004 such that fluid cannot flow through the inlet ports 4006 while the tips are disposed in their initial, joined configuration. When one or more other fluid inlet ports 4008 formed in the tips become clogged or obstructed, a flushing operation can be performed to separate the catheter tips and expose the previously covered inlet ports 4006 to restore fluid flow through the catheter. The tips 4002, 4004 can be joined by an adhesive 4010 configured to release the tips when the pressure applied by a flushing operation exceeds the bond strength of the adhesive. The type and the amount of the adhesive can thus be selected to control the pressure required to separate the tips of the catheter. The tips of the catheter can also be separated along a perforation or frangible seam when the pressure applied by a flushing operation exceeds the tensile strength of the perforation or seam.

Figure 41:
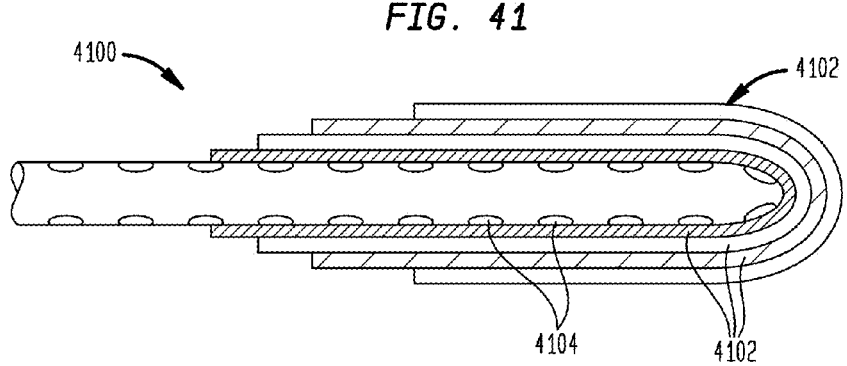
FIG. 41 is a sectional view of a catheter with one or more degradable sheaths.

FIG. 41 illustrates another exemplary embodiment of a catheter 4100. The catheter 4100 includes one or more degradable sheaths 4102 configured to degrade over time with exposure to fluid within a patient's ventricle. As the sheaths 4102 degrade, they expose auxiliary fluid inlet holes 4104 that were previously covered by the sheaths. In the illustrated embodiment, a plurality of staggered sheaths 4102 are provided such that the sheath length gradually decreases from the innermost sheath to the outermost sheath. As a result, degradation of only one sheath thickness is required to expose the proximal-most auxiliary holes, whereas degradation of four sheath thicknesses is required to expose the distal-most auxiliary holes. The illustrated catheter 4100 is thus configured to gradually expose additional fluid inlet holes 4104 as time passes (e.g., in a number of stages equal to the number of staggered sheaths 4102, which stages can be spread over multiple days, weeks, months, etc.). In addition, one or more of the auxiliary holes 4104 can be opened instantly (i.e., without waiting for the sheath 4102 to degrade) by performing a flushing operation. The resulting pressure spike in the catheter 4100 can cause one or more of the sheaths 4102 to rupture (e.g., in a region where only a single ply of the sheath remains) to open the auxiliary holes 4104 disposed underneath.

Figure 42:
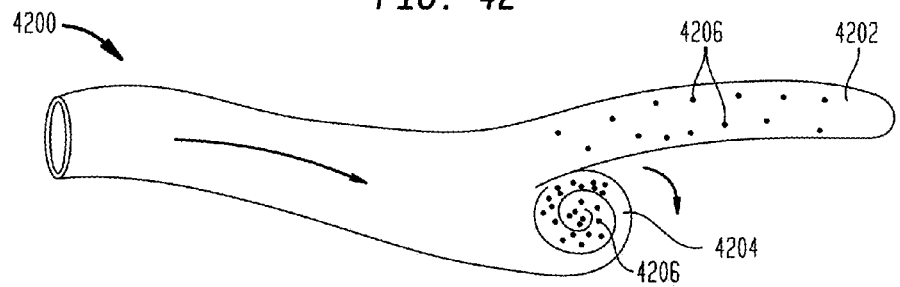
FIG. 42 is a sectional view of a split-tip catheter having a rolled up auxiliary tip.

FIG. 42 illustrates another exemplary embodiment of a catheter 4200. The catheter 4200 is a split-tip catheter having a primary tip 4202 and a secondary tip 4204 which each have one or more fluid inlet holes 4206 formed therein. The secondary tip 4204 is initially rolled up on itself and tacked such that the fluid inlet holes formed in the secondary tip are blocked by the adjacent rolled portions of the secondary tip. When a flushing operation is performed, or when a flushing operation is attempted and is unsuccessful in clearing the primary tip 4202, the fluid pressure in the catheter 4200 can increase until it exceeds the bond strength of the tack, thereby severing the tack and allowing the secondary tip 4204 to unroll. Once unrolled, the fluid inlet ports 4206 of the secondary tip 4204 are exposed and fluid can pass therethrough into the interior of the catheter 4200.

Figure 43A:
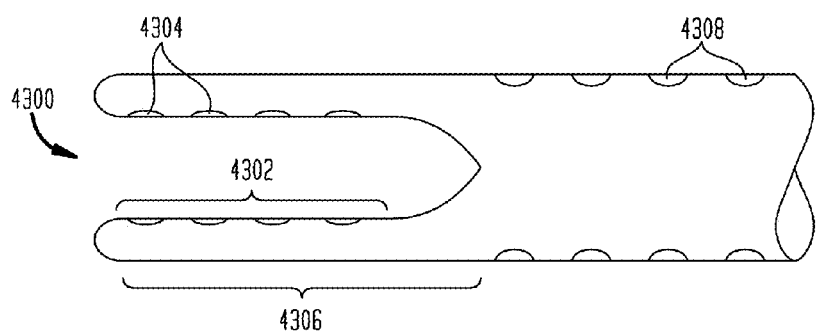
FIG. 43A is a sectional view of a catheter having a folded-in distal end before a flushing operation.
Figure 43B:
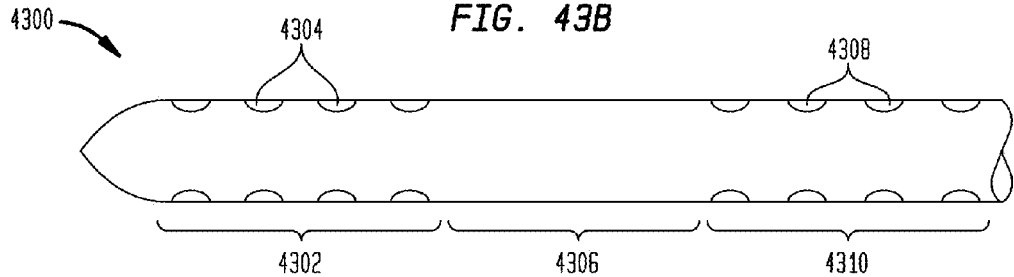
FIG. 43B is a sectional view of the catheter of FIG. 43A after a flushing operation.

FIGS. 43A-43B illustrate another exemplary embodiment of a catheter 4300. A terminal distal tip 4302 of the catheter having one or more auxiliary fluid inlet holes 4304 formed therein is initially folded in on itself and tacked to a more-proximal section 4306 of the catheter, as shown in FIG. 43A. One or more primary fluid inlet ports 4308 formed in a proximal section 4310 of the catheter are open to allow fluid to enter the central lumen of the catheter. When one or more of the primary fluid ports 4308 is blocked or obstructed, a flushing operation can be performed to break the tack holding the folded-in portion 4302 of the catheter and force the folded-in portion to unfold. As shown in FIG. 43B, when the initially folded-in portion 4302 is unfolded, the auxiliary fluid ports 4304 formed therein are opened and fluid is free to flow through the auxiliary fluid ports into the inner lumen of the catheter. In some embodiments, the catheter 4300 can be a split-tip catheter and one or both of the tips can have a folded-in auxiliary portion.

FIGS. 44A-44B illustrate another exemplary embodiment of a catheter 4400. The catheter 4400 includes an accordion or bellows portion 4402 formed adjacent a distal end thereof in which one or more auxiliary fluid inlet ports 4404 are formed. The bellows portion 4402 is initially tacked in a folded position, as shown in FIG. 44A, such that the auxiliary fluid inlet ports 4404 are covered by adjacent folds of the bellows portion. When one or more of primary fluid inlet ports become blocked or obstructed, a flushing operation can be performed to break the tack holding the bellows portion 4402 in the folded position to open up the auxiliary fluid inlet ports 4404 and restore fluid flow through the catheter, as shown in FIG. 44B. In some embodiments, tacks of varying strength can be formed between successive folds of the bellows portion 4402, such that each flushing operation is only effective to break the weakest remaining tack and expose the auxiliary ports formed in the corresponding fold of the bellows portion. In other words, a first flushing operation can break a first tack to expose a first auxiliary port. When the first auxiliary port becomes clogged, a second flushing operation can break a second tack to expose a second auxiliary port. This process can be repeated until all of the tacks are broken. The usable life of the catheter can thus be effectively extended by a factor equal to the number of tacks in the bellows portion. In some embodiments, the catheter can be a split-tip catheter and one or both of the tips can have a bellows portion.

FIG. 45 illustrates another exemplary embodiment of a catheter 4500. The catheter 4500 includes a plurality of primary fluid inlet ports 4502 formed in a distal end thereof. The catheter also includes a plurality of blind bores or non-full thickness penetrations 4504. In use, when the primary fluid inlet ports 4502 are blocked, a pressure spike in the catheter can be produced as the result of a flushing operation to rupture the remaining material in the blind bores 4504, thereby converting the blind bores into auxiliary fluid inlet ports and restoring the flow of fluid through the catheter. The blind bores 4504 can be formed to varying depths such that a tiered opening can be achieved with multiple successive flushes. In other words, the deepest bores can be opened in a first flushing operation. When those bores become clogged, the next-deepest bores can be opened in a second flushing operation. This process can be repeated until all of the bores have been opened.

FIG. 46 illustrates another exemplary embodiment of a catheter 4600. The catheter 4600 includes an arm 4602 that extends longitudinally through the inner lumen of the catheter. A plurality of fingers 4604 extend radially outward from the arm 4602. When any of the fluid inlet ports 4606 formed in the catheter 4600 becomes blocked, a flushing operation can be performed to advance and/or retract the arm 4602 such that the fingers 4604 push any obstructions blocking the inlet ports out of the catheter. In an exemplary embodiment, depressing a dome portion of a flusher acts on a linkage to advance the arm 4602 longitudinally and allowing the dome to return to its un-collapsed configuration pulls the linkage back to retract the arm longitudinally. This process can be performed repeatedly to "brush" the fluid inlet ports 4606 with the fingers 4604, dislodging any debris that is blocking or clogging the inlet ports. The arm 4602 can also be translated hydraulically using fluid pressure supplied to the catheter by a flushing operation.

Figure 47A:
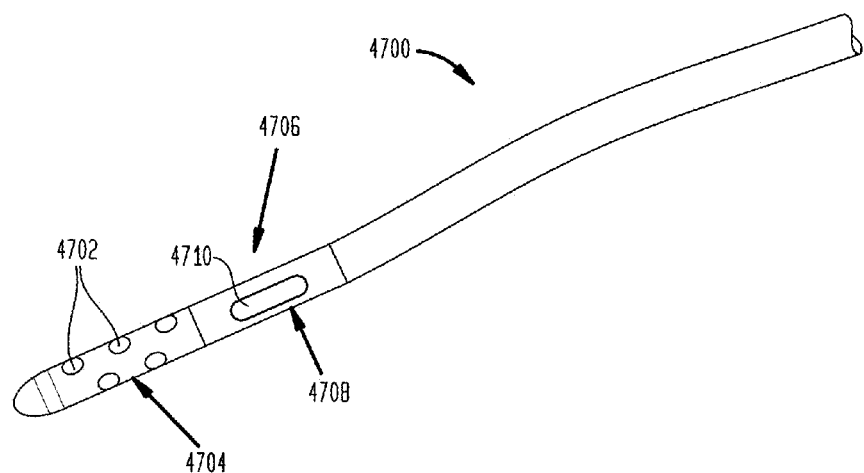
FIG. 47A is a perspective view of a catheter with a slot-shaped auxiliary hole.

FIG. 47A illustrates another exemplary embodiment of a catheter 4700. The catheter 4700 includes a plurality of primary inlet holes 4702 formed at a distal tip end 4704 of the catheter configured to be disposed within a patient's ventricle. While a single-lumen, single-tip catheter is shown, it will be appreciated that the catheter can be a multi-lumen catheter and/or a multi-tip catheter. The primary holes 4702 form pathways through which fluid external to the catheter 4700 can enter an inner lumen of the catheter. The catheter also includes a segment 4706 in which one or more slot-shaped auxiliary holes 4708 are formed. The auxiliary slots 4708 are initially blocked such that fluid external to the catheter 4700 cannot pass through the auxiliary slots into an inner lumen of the catheter. Rather, fluid can only pass through the auxiliary slots 4708 after they are forced open (e.g., by a flushing operation of one of the flushers disclosed above). The auxiliary slots 4708 are initially blocked by a membrane 4710. The membrane 4710 can be formed from a variety of implantable and biocompatible materials, such as silicone or other silastic materials. The catheter 4700 can be manufactured in various ways. For example, the slot(s) 4708 can be formed by making non-full-thickness punches into the side of the catheter tubing. The slots can also be formed by punching all the way through the catheter tubing and then molding the membrane 4710 over or otherwise attaching the membrane to the catheter. By way of further example, the section 4706 of the catheter in which the slot(s) 4708 are formed and the distal portion 4704 of the catheter in which the primary inlet holes 4702 are formed can be molded as a single component. As yet another example, the entire catheter 4700 can be molded as a single component.

Figure 47B:
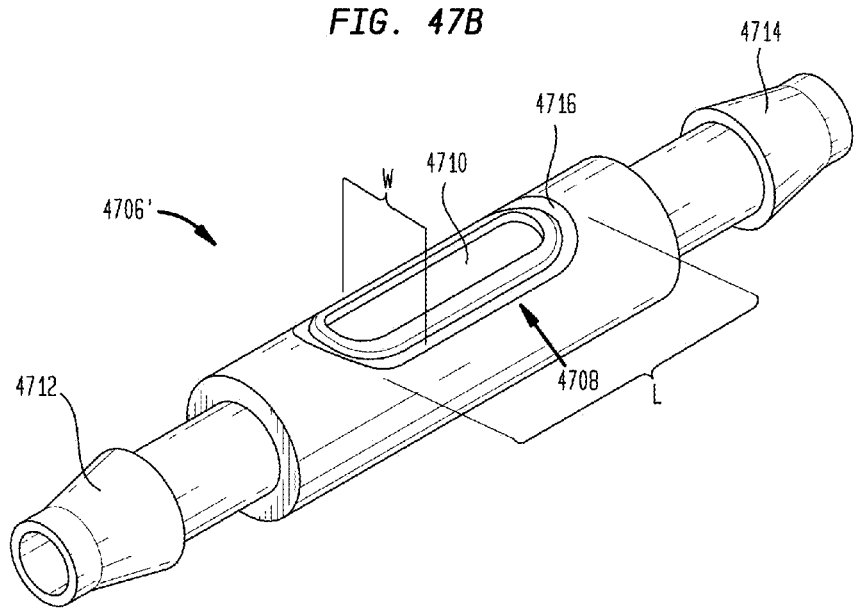
FIG. 47B is a perspective view of an inline catheter component.

As shown in FIG. 47B, the section of the catheter 4700 in which the auxiliary slot or slots 4708 are formed can be a separate molded part 4706' with inlet and outlet barbs 4712, 4714 for coupling the molded part to proximal and distal sections of the catheter 4700. The pop-out auxiliary holes or slots 4708 can thus be provided as an inline component for assembly with other portions of the catheter. In some embodiments, the molded part 4706' can be formed from a different material (e.g., a stiffer or higher-durometer material) than the remainder of the catheter to provide additional support for the membrane 4710. The molded part 4706' can have an overall length of about 0.82 inches and the cylindrical main body portion of the molded part can have a length of about 0.40 inches.

In some embodiments, the catheter tubing can have an inside diameter of about 0.050 inches and a thickness of about 0.030 inches such that the outside diameter of the catheter is about 0.110 inches. In some embodiments, the distal portion of the catheter in which the primary holes are formed can have a length of about 0.394 inches. In some embodiments, the diameter of the primary holes can be about 0.047 inches. In some embodiments, the auxiliary slots can have a length L of between about 0.050 inches to about 0.220 inches. In some embodiments, the auxiliary slots can have a width W of about 0.050 inches. In some embodiments, the membrane can have a thickness between about 0.001 inches and 0.010 inches. The auxiliary slots can have any of a variety of shapes. For example, the slots can be substantially rectangular with rounded corners as shown. Alternatively, the corners of the slot can be sharper to make the corners burst more easily. In some embodiments, the membrane can include scoring 4716 to provide a seam or weakness along which the membrane can tear. The membrane can be formed from any of a variety of materials, including silastic materials such as silicone, polyurethane, and the like. In some embodiments, the membrane can be configured to tear only when a pressure of at least about 10 psi to at least about 25 psi or more is applied thereto.

Figure 48A:
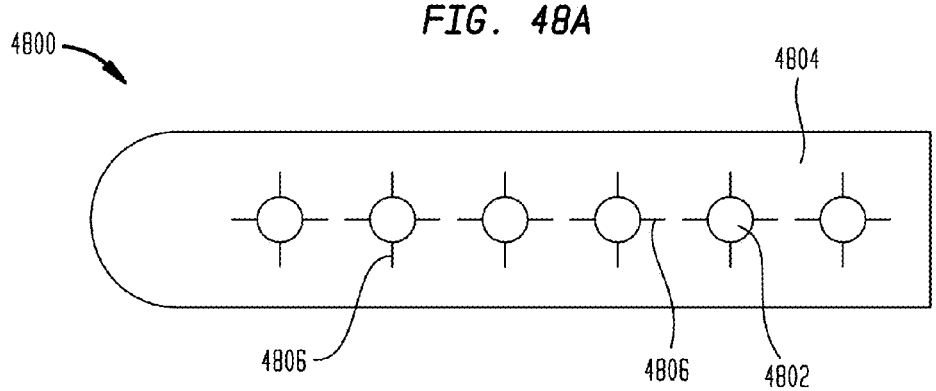
FIG. 48A is a plan view of a catheter with cross-slit inlet holes.
Figure 48B:
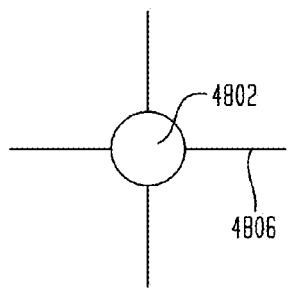
FIG. 48B is a plan view of a cross-slit inlet hole not under pressure.
Figure 48C:
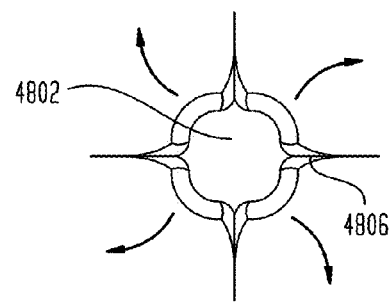
FIG. 48C is a plan view of a cross-slit inlet hole under pressure.
Figure 48D:
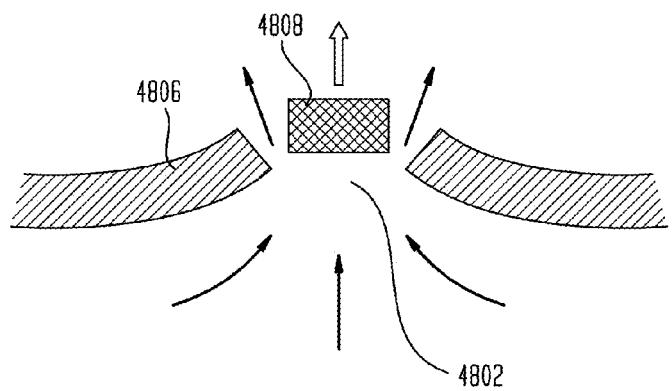
FIG. 48D is a sectional profile view of a cross-slit inlet hole under pressure.

FIGS. 48A-48D illustrate another exemplary embodiment of a catheter 4800. The catheter 4800 includes a plurality of inlet holes 4802 formed at a distal tip end 4804 of the catheter configured to be disposed within a patient's ventricle. While a single-lumen, single-tip catheter is shown, it will be appreciated that the catheter can be a multi-lumen catheter and/or a multi-tip catheter. The inlet holes 4802 form pathways through which fluid external to the catheter 4800 can enter an inner lumen of the catheter. Slits 4806 can be formed in one or more of the inlet holes to allow the hole to deflect and open slightly when flushed, making it easier for any blockage 4808 disposed in the hole to break free and flush out of the catheter. In other words, the periphery of the inlet hole 4802 is configured to deform outwards when the catheter is flushed. FIG. 48B shows a hole 4802 with a cross-shaped slit 4806 under normal operating pressure. As shown in FIGS. 48C-48D, when the pressure increases beneath the hole 4802 during a flushing operation, the hole blossoms outwards along the slits 4806, expanding such that the blockage 4808 can be cleared more easily. The inlet holes 4802 can have slits 4806 oriented at any of a variety of angles. For example, the slits can be horizontal, vertical, or can include perpendicularly-intersecting horizontal and vertical slits as shown.

FIGS. 58A-58B illustrate an exemplary embodiment of a catheter 5800. The catheter 5800 includes a plurality of inlet holes formed at a distal tip end of the catheter configured to be disposed within a patient's ventricle. While a single-lumen, single-tip catheter is shown, it will be appreciated that the catheter can be a multi-lumen catheter and/or a multi-tip catheter. For example, the catheter can be a dual lumen catheter with two independent lumens that extend the full length of the catheter. By way of further example, the catheter can be a split-tip catheter having first and second tips at the distal end that merge into a single lumen that extends through the remainder of the catheter.

The plurality of inlet holes includes one or more primary holes 5802 which form pathways through which fluid external to the catheter 5800 can enter an inner lumen of the catheter. The plurality of inlet holes also includes one or more auxiliary holes 5804 which are initially blocked such that fluid external to the catheter 5800 cannot pass through the auxiliary holes into an inner lumen of the catheter. Rather, fluid can only pass through the auxiliary holes 5804 after they are forced open (e.g., by a flushing operation of one of the flushers disclosed above). The auxiliary holes 5804 are initially blocked by a membrane 5806. In some embodiments, the membrane 5806 can be disposed over the exterior surface of the catheter 5800. The membrane 5806 can be formed from a variety of implantable and biocompatible materials, such as silicone. The membrane 5806 can be stretched across the openings 5804 and attached to the catheter 5800 under tension, such that penetration of the membrane results in a tear in which opposed sides of the tear move out of the way of the underlying hole. The membrane 5806 can be stretched over the auxiliary holes 5804 in a variety of directions or orientations, which can allow for the tear produced when the membrane is ruptured to have some directionality (i.e., to define an opening that faces in a particular direction). The stretched membrane 5806 can be attached to the catheter 5800 in various ways. For example, the membrane 5806 can be thermally welded to the catheter 5800 using a heat punch, mechanically coupled to the catheter using O-rings disposed around the membrane and the catheter, or molded into or onto the catheter. In some embodiments, a plurality of auxiliary holes can be provided, each having a membrane stretched in a different direction. The thickness of the membrane, the degree of tension applied to the membrane, and the material from which the membrane is formed can be selected to control the force required to tear the membrane. In some embodiments, the membrane can be configured to burst at an opening pressure of about 5 psi to about 15 psi. In some embodiments, the membrane is formed from silicone and has a thickness of about 0.001 inches.

The catheter 5800 can include a stiffening sleeve 5801 disposed over the membrane. The stiffening sleeve 5801 can include an opening 5803 that is aligned with the auxiliary hole 5804, and can be positioned in a recessed portion 5805 of the catheter such that the stiffening sleeve and the catheter define a continuous, smooth outer surface. The stiffening sleeve 5801 can advantageously prevent the catheter 5800 from bending or ballooning under the pressure of a flushing cough while at the same time focusing the cough pressure on the membrane 5806. The catheter 5800 can also include a bullet-tip plug 5809 that seals the terminal distal end of the catheter.

In some embodiments, the catheter 5800 can be manufactured by extruding a silicone tube to form a catheter main body 5807 with the desired inside and outside diameters. The tube can then be cut to the desired length. The distal portion 5811 of the catheter, including the recess 5805 for the stiffening sleeve 5801, can then be formed on one end of the tube using a silicone overmolding process. Primary and auxiliary holes 5802, 5804 can be added to this distal portion 5811 later in a separate drilling step. Once the auxiliary hole 5804 is formed, a silicone membrane 5806 can be molded over the opening. Alternatively, the membrane 5806 and the auxiliary hole 5804 defined beneath the membrane 5806 can be formed simultaneously by molding them as one monolithic, continuous part formed from silicone or other materials. In other words, the auxiliary hole 5804 can be initially formed as a non-full-thickness or blind hole, with the remaining thickness defining the membrane 5806. The stiffening sleeve 5801 can be formed from a PEEK extrusion and a laser cutting process can be used to form the window 5803 in the stiffening sleeve. The stiffening sleeve 5801 can be positioned over the membrane 5806 and bonded in place using RTV silicone or the like. The distal plug 5809 can be molded as a separate silicone component and then sealed to the distal end of the catheter using RTV silicone of the like.

Any one or more components of the catheter 5800 can be formed from a radiopaque material or can have a radiopaque material embedded or impregnated therein to facilitate visualization using various imaging techniques. In some embodiments, barium sulfate or other radiopaque materials can be molded into the distal portion 5811 of the catheter, the main body 5807 of the catheter, the stiffening sleeve 5801, the membrane 5806, and/or the distal tip 5809.

Figure 59A:
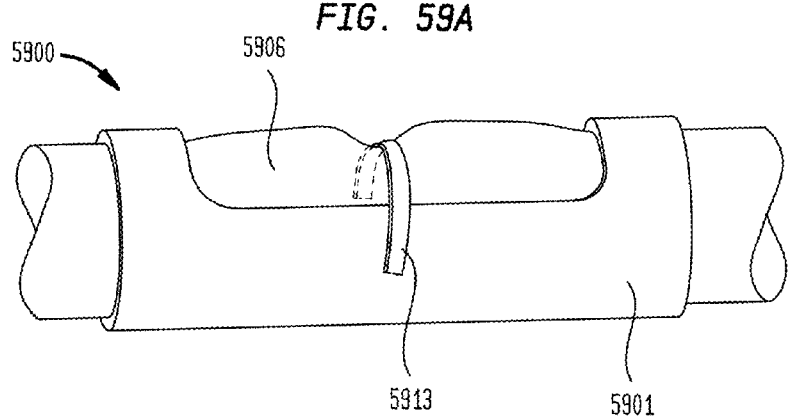
FIG. 59A is a perspective view of a catheter with a radiopaque band disposed over an auxiliary flow membrane.
Figure 59B:
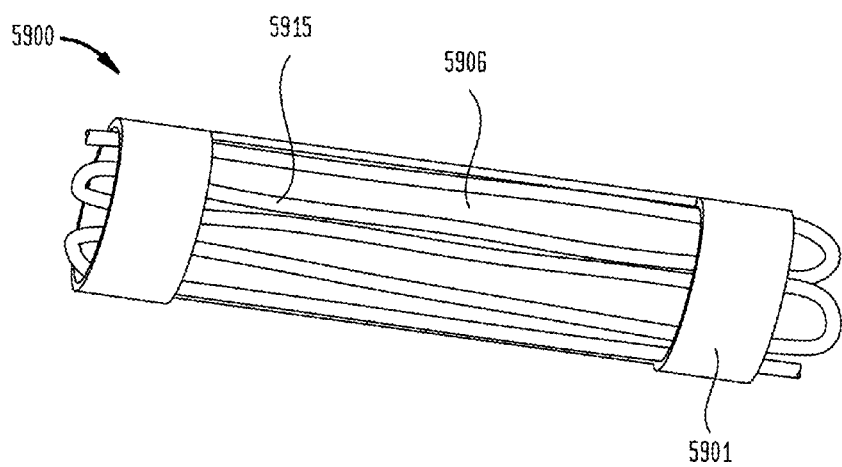
FIG. 59B is a perspective view of a catheter with a radiopaque wire disposed over an auxiliary flow membrane.

The catheter 5800 can include various features for facilitating a determination as to whether the membrane 5806 has been opened using CT, X-ray, or other imaging techniques. For example, a thin ribbon of radiopaque material can be printed on the membrane. When the membrane opens, radiographic images of the implanted catheter can show the ribbon of material being torn away or separated. The ribbon can be deposited or printed on the membrane in an ultra-thin layer using nanotechnology. The ribbon can extend longitudinally, laterally, diagonally, or in any other direction or directions across the auxiliary opening, and can be formed in a matrix or any other pattern. FIG. 59A illustrates a catheter 5900 having a thin ribbon 5913 of metal extending laterally across the membrane 5906 and held in place by the stiffening sleeve 5901. The ribbon can also be deposited as a series of dots or grid lines. As yet another example, the membrane can be initially covered by a radiopaque window that pops out and floats away after the membrane bursts. Presence or absence of the radiopaque window in images of the catheter can be used to determine whether the membrane has burst. By way of further example, a radiopaque wire can be looped back and forth longitudinally across the auxiliary opening such that, when the membrane is opened, the wire stretches out of the opening to provide an indication in radiographic images that the membrane has burst. As shown in FIG. 59B, the wire 5915 can be disposed over the membrane 5906 of the catheter 5900 and under the stiffening sleeve 5901 such that the ends of the wire remain attached to the catheter after the membrane bursts. In a still further example, an antenna that resonates when excited with RF energy can be disposed over the membrane and can be configured to bend, break, or otherwise distort when the membrane bursts. Accordingly, the response received from the antenna can be monitored or measured to detect changes in the response or ceasing of the response as an indication that the membrane has burst.

Figure 60A:
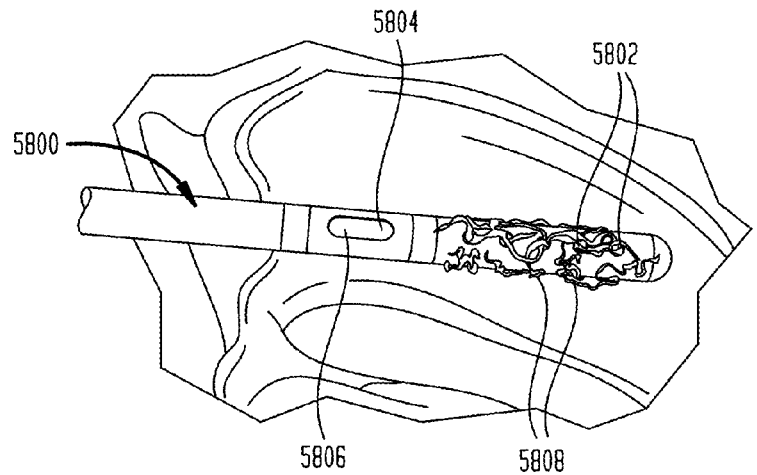
FIG. 60A is a perspective view of an implanted catheter with obstructions blocking primary inlet ports of the catheter.
Figure 60B:
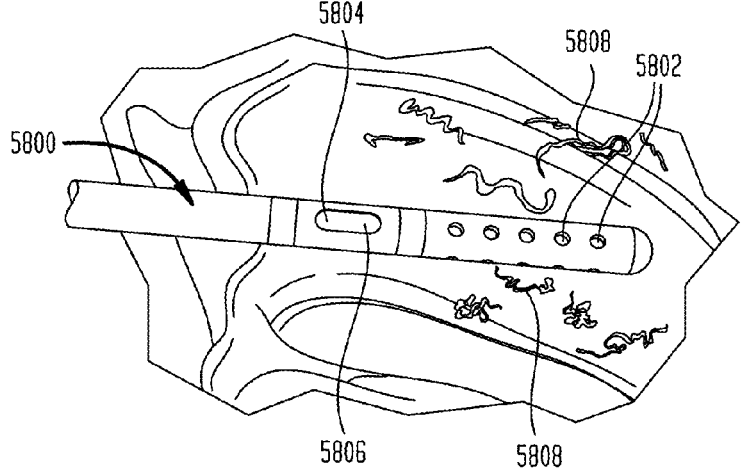
FIG. 60B is a perspective view of the catheter of FIG. 60A with the obstructions cleared by a flushing operation.
Figure 60C:
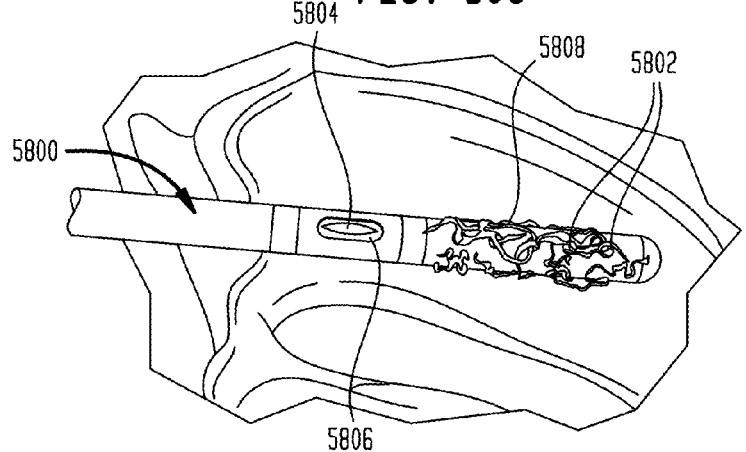
FIG. 60C is a perspective view of the catheter of FIG. 60A with an auxiliary inlet port of the catheter having been opened by a flushing operation.

In use, the catheter 5800 is implanted in a patient with the distal tip of the catheter disposed in the patient's ventricle. Fluid enters the primary holes 5802 of the catheter and flows through the inner lumen of the catheter to a downstream portion of the shunt system (e.g., a flusher, a valve, and/or a drain catheter). When the primary holes 5802 become clogged or obstructed (e.g., as shown in FIG. 60A), or at any other time a user so desires, a flusher can be actuated to deliver a pressurized cough of fluid through the inner lumen of the catheter. The cough of fluid can dislodge obstructions 5808 from the clogged primary holes 5802 (e.g., as shown in FIG. 60B) and/or cause the membrane 5806 covering one or more auxiliary holes 5804 to burst (e.g., as shown in FIG. 60C). In other words, flushing the catheter can open the auxiliary inlet ports 5804 to provide a secondary fluid pathway into the catheter, e.g., when the primary fluid pathway becomes clogged or obstructed.

Figure 61:
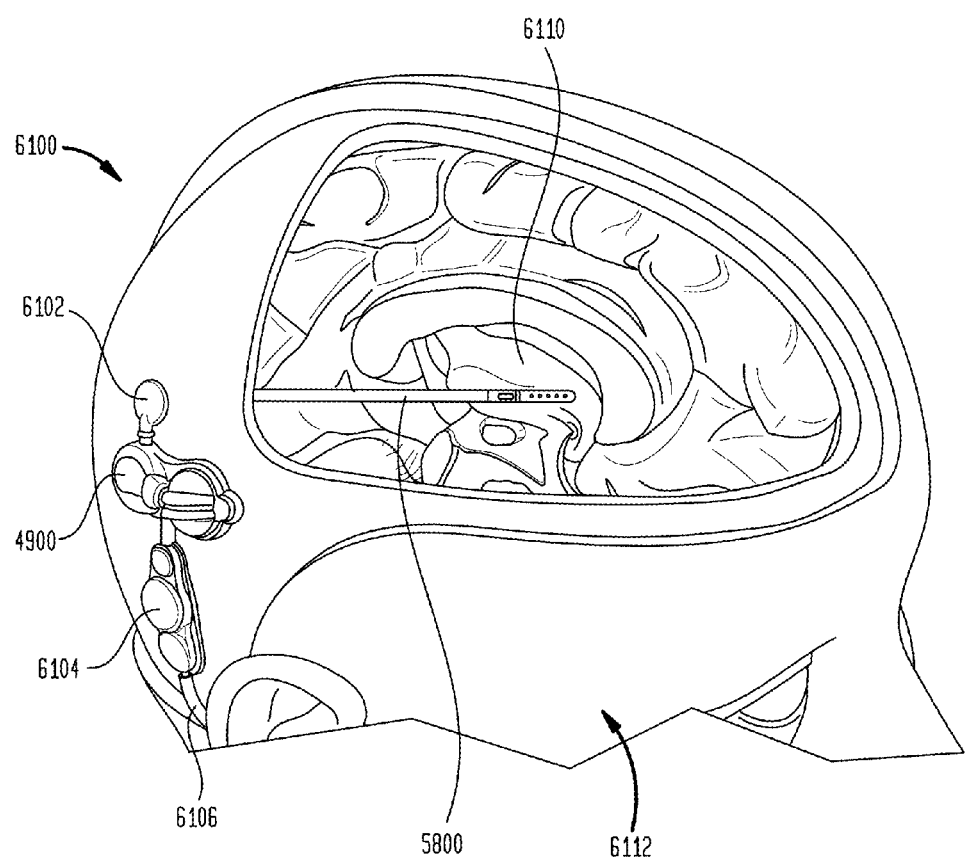
FIG. 61 is a perspective view of a patient with a shunt system implanted therein.

FIG. 61 illustrates one exemplary embodiment of a shunt system 6100 that includes the flusher 4900 of FIGS. 49A-49G and the catheter 5800 of FIGS. 58A-58B. The ventricular catheter 5800 extends from an anchor 6102 which is coupled to the upstream port of the flusher 4900. The downstream port of the flusher is connected to a shunt valve 6104, which is in turn coupled to a drain catheter 6106. In some embodiments, the shunt system 6100 can be used to treat hydrocephalus by implanting the ventricular catheter 5800 such that a distal end of the catheter is disposed within a brain ventricle 6110 of a patient 6112. The anchor 6102 can be mounted to the patient's skull, beneath the skin surface, and the drain catheter 6106 can be implanted such that the proximal end of the drain catheter is disposed within a drain site, such as the abdominal cavity. The valve 6104 can be configured to regulate the flow of fluid from the ventricle 6110 to the drain site. For example, when fluid pressure in the ventricle exceeds the opening pressure of the valve 6104, the valve can be configured to open to allow excess fluid to drain out of the ventricle 6110. When the fluid pressure drops to an acceptable level, the valve 6104 can be configured to close, thereby stopping further draining of fluid. The flusher 4900 can be actuated as described above to clear obstructions from the shunt system (e.g., from the primary openings of the catheter 5800). Alternatively, or in addition, the flusher 4900 can be actuated to open one or more auxiliary flow paths through the shunt system (e.g., by popping open the membrane of the catheter 5800).

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A method of flushing a shunt system, comprising:
   in a single motion, applying a force to a flusher at a single contiguous contact area, the flusher including a flow path that extends between an upstream port and a downstream port, at least a portion of the flow path being defined by a pinch tube that extends across an exterior surface of a flush dome, the force being effective to collapse the pinch tube, thereby closing off a connection to the downstream port, and to collapse the flush dome;
   wherein collapsing the flush dome is effective to release a cough of pressurized fluid through an upstream portion of the shunt system.

2. The method of claim 1, further comprising rotating an adjustment disc of the flusher to adjust the pressure at which a valve of the flusher opens to release the cough of fluid.

3. The method of claim 2, wherein rotating the disc compresses a valve body against a wall of a chamber formed in the flusher.

4. The method of claim 1, further comprising removing the force from the flush dome to allow the flush dome to expand and open a refill valve to refill the flush dome with fluid.

5. The method of claim 4, wherein opening the refill valve allows fluid to flow from a flow channel formed in a refill plate, through a plurality of openings arranged circumferentially around the refill valve, and into the flush dome.

6. The method of claim 1, wherein applying the force exerts pressure on a refill valve disposed in the flush dome to hold the refill valve in a closed position.

7. The method of claim 6, wherein the force is applied along an axis that is substantially parallel to an axis along which the refill valve opens and closes.

8. The method of claim 1, wherein the pinch tube is more easily deformable than the flush dome.

9. The method of claim 1, wherein the force is applied by exerting finger pressure through the skin of a patient in which the flusher is implanted.

10. The method of claim 1, wherein the cough of fluid clears an obstruction from a catheter in fluid communication with the flusher.

11. The method of claim 1, wherein the cough of fluid opens an auxiliary flow path through a catheter in fluid communication with the flusher.

12. The method of claim 1, further comprising removing the force from the flush dome following the cough of fluid such that a refill valve of the flusher opens, thereby fluidly connecting the interior of the flush dome to the flow path and refilling the flush dome.

* * * * *